United States Patent [19]
Magar et al.

[11] Patent Number: 5,847,006
[45] Date of Patent: *Dec. 8, 1998

[54] THERAPEUTIC GUANIDINES

[75] Inventors: Sharad Magar, Somerville; Graham J. Durant, Cambridge; Lain-Yen Hu, Bedford; Stanley M. Goldin, Lexington; N. Laxma Reddy, Malden; James B. Fischer, Cambridge; Subbarao Katragadda, Belmont; Andrew Gannett Knapp, Salem; Lee David Margolin, Belmont, all of Mass.

[73] Assignee: Cambridge NeuroScience, Inc., Cambridge, Mass.

[*] Notice: The term of this patent shall not extend beyond the expiration date of Pat. Nos. 5,614,630 and 5,622,968.

[21] Appl. No.: 454,927

[22] Filed: May 31, 1995

Related U.S. Application Data

[63] Continuation-in-part of Ser. No. 155,930, which is a continuation of PCT/US94/13541 Nov. 22, 1994, abandoned, which is a continuation-in-part of Ser. No. 833,421, Feb. 10, 1992, Pat. No. 5,403,861, which is a continuation-in-part of Ser. No. 652,104, Feb. 8, 1991, abandoned.

[51] Int. Cl.⁶ ............. A01N 37/52; C07C 277/00
[52] U.S. Cl. ............. 514/634; 564/237; 564/238
[58] Field of Search ............. 564/238, 239; 514/634

[56] References Cited

U.S. PATENT DOCUMENTS

| | | | |
|---|---|---|---|
| 1,422,506 | 7/1922 | Weiss | 564/238 |
| 1,597,233 | 8/1926 | Heuser et al. | 564/238 |
| 1,642,180 | 9/1927 | Scott | 564/238 |
| 1,672,431 | 6/1928 | Schotte | 564/238 |
| 1,677,235 | 7/1928 | Heuser . | |
| 1,730,388 | 10/1929 | Brooks . | |
| 1,756,315 | 4/1930 | terHorst | 564/238 |
| 1,795,398 | 3/1931 | Schotte | 564/238 |
| 1,850,682 | 3/1932 | Meiss | 564/238 |
| 1,915,922 | 6/1933 | Christmann et al. | 564/238 |
| 2,145,214 | 1/1939 | Jayne, Jr. | 167/37 |
| 2,254,009 | 8/1941 | Hechenbleikner | 260/564 |
| 2,274,476 | 2/1942 | Hechenbleikner | 167/30 |
| 2,289,541 | 7/1942 | Ericks et al. | 167/22 |
| 2,362,915 | 11/1944 | MacGregor | 3/74 |

(List continued on next page.)

FOREIGN PATENT DOCUMENTS

| | | |
|---|---|---|
| 0001500 | 4/1979 | European Pat. Off. . |
| 0035374 | 9/1981 | European Pat. Off. . |
| A 0179642 | 4/1986 | European Pat. Off. . |
| 514248 | 11/1930 | Germany . |
| 2029707 | 12/1970 | Germany . |
| 2133 056 | 1/1973 | Germany . |
| 2452691 | 5/1975 | Germany . |
| 3108564 | 11/1982 | Germany . |
| 223410 | 10/1924 | United Kingdom . |
| 224376 | 11/1924 | United Kingdom . |
| 258203 | 9/1926 | United Kingdom . |
| 478525 | 1/1938 | United Kingdom . |
| 1208252 | 10/1970 | United Kingdom . |
| WO 87/04433 | 7/1987 | WIPO . |
| WO 88/00583 | 1/1988 | WIPO . |
| WO 90/12575 | 11/1990 | WIPO . |
| WO 90/14067 | 11/1990 | WIPO . |
| WO 91/12797 | 9/1991 | WIPO . |
| WO 91/18868 | 12/1991 | WIPO . |
| WO 92/14697 | 9/1992 | WIPO . |
| WO 95/20950 | 8/1995 | WIPO . |

OTHER PUBLICATIONS

D. Lloyd et al., *Tetrahedron*, 33:1379–1389 (1977).
H. Shimazu et al., *Chemical Abstracts*, 111(2):16337m (1989).
T. Tada et al., *Chemical Abstracts*, 104(24): 208252g (1986).
L. Kiselev et al., *Chemical Abstracts*, 91(21): 175291b (1979).
A. Heesing et al., *Chemical Abstracts*, 64(1): 15776h (1966)
K. Akiba et al., *Bull. Chem. Soc. Jap.*, 47(4):935–937 (1974).
J. Keana et al., *Proc. Natl. Acad. Sci.*, 86:5631–5635 (1989).
S. Siddiqui et al., *Pakistan Journal of Scientific and Industrial Res.*, 30(3): 163–181 (1987).
E. Maida et al., *Wiener Klinische Wochenschrift*, 90(2):43–48 (1978).
C. Chavkin et al., *Advances in the Biosciences*, 75:407–410 (1989).
P.N. Bhargava et al., *Chemical Abstracts*, 86:598, 189787b (1977).
H.W. Geluk et al., *J. Med Chem.*, 12:712–715 (1969).
M.W. Scherz et al., *J. Med. Chem.*, 33:2421–2429 (1990).
A.A. Stolyarchuck et al., *Chemical Abstracts*, 86:522–523, 121071h (1977).
T.J.R. Weakley et al., *Acta. Cryst.*, 46:2234–2236 (1990).
J.T. Adams et al., *Eur. J. Pharm.*, 142:61–71 (1987).
B.G. Campbell et al., *J. Neurosci.*, 9:3380–3391 (1989).
G.J. Durant et al., *J. Med. Chem.*, 28:1414–1422 (1985).
M.P. Kavanaugh et al., *Proc. Natl. Acad. Sci. USA*, 85:2844–2848 (1988).
B. Tester et al., *Society for Neuroscience, 19th Annual Meeting*, 983, 396.17 (1989).

(List continued on next page.)

*Primary Examiner*—José G. Dees
*Assistant Examiner*—Alton Pryor
*Attorney, Agent, or Firm*—David G. Conlin; Peter F. Corless; Dike, Bronstein, Roberts & Cushman, LLP

[57] ABSTRACT

The present invention provides N,N'-diaryl substituted guanidines having therapeutic utility. The compounds of the present invention are represented by the formula:

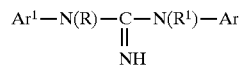

wherein R and R¹ represent hydrogen or other group and Ar and Ar¹ represent selected aryl groups, and at least one being acenaphthyl.

27 Claims, No Drawings

U.S. PATENT DOCUMENTS

| | | | |
|---|---|---|---|
| 2,633,474 | 3/1953 | Beaver | 260/565 |
| 2,704,710 | 3/1955 | Sprung | 95/2 |
| 3,117,994 | 1/1964 | McKay et al. | 260/564 |
| 3,140,231 | 7/1964 | Luskin et al. | 167/65 |
| 3,159,676 | 12/1964 | Spickett et al. | 360/564 |
| 3,168,562 | 2/1965 | Walton et al. | 564/237 |
| 3,228,975 | 1/1966 | Abraham et al. | 260/501 |
| 3,248,426 | 4/1966 | Dvornik | 260/564 |
| 3,252,861 | 5/1966 | Mull | 167/65 |
| 3,270,054 | 8/1966 | Gagneux et al. | 260/564 |
| 3,283,003 | 11/1966 | Jack et al. | 260/564 |
| 3,301,755 | 1/1967 | Mull | 167/65 |
| 3,320,229 | 5/1967 | Szabo et al. | 260/96.5 |
| 3,391,189 | 7/1968 | Mull | 260/564 |
| 3,409,669 | 11/1968 | Dyke | 260/564 |
| 3,479,437 | 11/1969 | Szabo et al. | 424/304 |
| 3,547,951 | 12/1970 | Hardie et al. | 260/340.9 |
| 3,639,477 | 2/1972 | L'Italien | 260/564 A |
| 3,681,459 | 8/1972 | Hughes et al. | 424/326 |
| 3,769,427 | 10/1973 | Hughes et al. | 424/326 |
| 3,784,643 | 1/1974 | Suh et al. | 260/564 A |
| 3,803,324 | 4/1974 | Winter et al. | 424/326 |
| 3,804,898 | 4/1974 | Panneman | 260/564 A |
| 3,908,013 | 9/1975 | Hughes et al. | 424/258 |
| 3,949,089 | 4/1976 | Maxwell et al. | 424/326 |
| 3,968,243 | 7/1976 | Maxwell et al. | 424/326 |
| 3,975,533 | 8/1976 | Gauri | 117/54 |
| 3,976,643 | 8/1976 | Diamond et al. | 260/247.5 R |
| 3,976,787 | 8/1976 | Hughes et al. | 424/326 |
| 4,007,181 | 2/1977 | DuCharme et al. | 260/247.5 R |
| 4,014,934 | 3/1977 | Hughes et al. | 260/565 |
| 4,051,256 | 9/1977 | Swallow | 424/304 |
| 4,052,455 | 10/1977 | Matier et al. | 260/563 R |
| 4,060,640 | 11/1977 | Kodama et al. | 424/326 |
| 4,109,014 | 8/1978 | Liu et al. | 424/326 |
| 4,130,663 | 12/1978 | Matier et al. | 424/326 |
| 4,161,541 | 7/1979 | Rasmussen | 424/326 |
| 4,169,154 | 9/1979 | Cohen et al. | 424/322 |
| 4,393,077 | 7/1983 | Douglas et al. | 564/238 |
| 4,471,137 | 9/1984 | Barton et al. | 564/240 |
| 4,709,094 | 11/1987 | Weber et al. | 564/238 |
| 4,742,054 | 5/1988 | Naftchi | 514/215 |
| 4,837,218 | 6/1989 | Olney | 514/646 |
| 4,891,185 | 1/1990 | Goldin | 422/69 |
| 4,898,978 | 2/1990 | Bergfield et al. | 564/231 |
| 4,906,779 | 3/1990 | Weber et al. | 564/238 |
| 5,093,525 | 3/1992 | Weber et al. | 564/238 |
| 5,190,976 | 3/1993 | Weber et al. | 514/634 |
| 5,262,568 | 11/1993 | Weber et al. | 564/238 |
| 5,298,657 | 3/1994 | Durant | 564/238 |
| 5,308,869 | 5/1994 | Keana et al. | 514/637 |
| 5,312,840 | 5/1994 | Keana et al. | 514/634 |
| 5,336,689 | 8/1994 | Weber et al. | 514/634 |
| 5,385,946 | 1/1995 | Keana et al. | 514/634 |

OTHER PUBLICATIONS

E. Weber et al., *Proc. Natl. Acad. Sci. USA*, 83:8784–8788 (1986).

C.A. Maryanoff et al., *J. Org. Chem.*, 51:1882–1884 (1986).

S.R. Safir et al., *J. Org. Chem.*, 13:924–932 (1948).

F.R. Sharp et al., *Society for Neuroscience Abstr.*, 18, Abstr. No. 482.3 (1992).

B. Clement et al., *Xenobiotica*, 23(2):155–167 (1993).

Kiselev et al., *Chemical Abstracts*, vol. 66 (1967).

B. Bean, *Ann. N.Y. Acad. Sci.*, 560:334–345 (1989).

B. Bean, *Annu. Rev. Physiol.*, 51:367–384 (1989).

Bent et al., *Pesticides*, 74:63479m (1971).

Chernevskaya et al., *Nature*, 349:418–420 (1991).

D. Choi, *Journal of Neuroscience*, 10(8):2493–2501 (1990).

D. Choi, *Cerebrovascular and Brian Metabolism Reviews*, 2:105–147 (1990).

D. Choi. *Neuron*, 1:623–634 (1988).

Dreyer et al., *Science*, 248:364–367 (1990).

Durant et al., *J. Med. Chem.* 9:22–27 (1966).

Fox et al., *J. Physiol.*, 394:149–172 (1987).

Fox et al., *J. Physiol.* 394:173–200 (1987).

Ginsburg et al., *Chemical Abstracts*, 4518 (1962).

Ginsburg et al., *Zhurnal Organicheskoi Khimii*, 7(11):2267–2270, Unverified Translation (1971).

Godfraind et al., *Trends in Pharmacological Sciences*, 10(8):297–301 (1989).

S. Goldin et al., *Synthetic Neuroprotective Glutamate Release Blockers*, Small Business Innovation Research Program Phase I Grant Application, funded Dec. 1991.

L. Heinisch, *Journal f. Prakt. Chemie*, 329:290–300 (1987).

Huisgen et al., *Chem. Ber.*, 98:1476–1486 (1965).

Huisgen et al., *Chem. Abstracts*, 63:2975 (1965).

Kaneko et al., *Arzneim. Forsch./Drug. Res.*, 39(1):445–450 (1989).

Katragadda et al., *Soc. for Neurosci. Abstr.*, 16:64 (1990).

Kreutzberger et al., *Arch. Pharmz. Ber. Deut. Pharm. Ges.*, 305;400–405 (1972).

Kroeger et al., *Chem. Abstr.*, 60:9264 (1964).

Kroger et al., *Ber.*,97:396–404 (1964).

Langlais et al., *J. Neuroscience*, 10(5):1664–1674 (1990).

Lemos et al., *Neuron*, 2:1419–1426 (1989).

Leung et al., *Neuron*, 3:767–772 (1989).

Malgouris et al., *J. Neuroscience*, 9(11):3720–3727 (1989).

B. Meldrum, *Cerebrovascular and Brian Metabolism Reviews*, 2:27–57 (1990).

Miura et al., *Chem. Abstr.*, 109:75455d (1988).

Plaitakis et al., *Science*, 216:193–196 (1982).

Plummer et al., *Neuron*, 2:1453–1463 (1989).

Podrebarac et al., *J. Med. Chem.*, 6:283–288 (1963).

Prasad et al., *Can J. Chem.*, 45:2247–2252 (1967).

Price et al., *Soc. Neuroscience Abstracts*, 16:377 (1990).

Sah et al., *Soc. Neuroscience Abstr.*, 15:823 (1989).

Sasaki et al., *Synthesis Nov.*, (11):718–719 (1975).

Subbarao et al., *soc. for Neurosci. Abstr.*, 15:601 (1989).

Sunderdiek et al., *Chemical Abstracts*, 81:91438k (1974).

J.B. Suszkiw, *NATO ASI Series*, H21:285–291 (1988).

Turner et al., *Soc. Neurosci. Abstr.*, 16:1014 (1990).

Turner et al., *Biochemistry*, 28:586–593 (1989).

Turner et al., *Analytical Biochemistry*, 178:8–16 (1989).

Turner et al., *Journal of Neuroscience*, 5(3):841–849 (1985).

Vasilev et al., *Chemistry Abstract*, 93:1500095u (1980).

Ahmad et al., *Chemical Abstract*, 108:221382 (1988).

THERAPEUTIC GUANIDINES

This is a continuation of International Application PCT/US94/13541, filed Nov. 22, 1994, which is a continuation-in part of U.S. application Ser. No. 08/155,930, filed Nov. 22, 1993, now abandoned, which is a continuation-in-part of U.S application Ser. No. 07/833,421, filed Feb. 10, 1992, now issued as U.S. Pat. No. 5,403,861, which is a continuation-in-part of U.S. application Ser. No. 07/652,104, filed Feb. 8, 1991, now abandoned.

BACKGROUND OF THE INVENTION

1. Field of the Invention

The present invention pertains to certain substituted guanidines, and methods of treatment and pharmaceutical compositions that utilize or comprise one or more such guanidines.

2. Background

Neurons of the mature central nervous system ("CNS") are highly specialized and in general do not replace themselves. Consequently, death or degeneration of cells in the nervous system can have far more serious consequences than cell death or degeneration in other organs. Abnormal neuronal death can be rapid and widespread as in traumatic brain injury, or can occur over many years among very specific populations of neurons as in chronic neurodegenerative diseases.

Substantial evidence now points to pernicious overactivity of normal neurotransmitter systems as a contributory mechanism in many instances of pathological neuronal degeneration. In particular, overstimulation of neuronal receptors for L-glutamate, the brain's most prevalent excitatory amino acid ("EAA") neurotransmitter, has been recognized as a causal or exacerbating factor in several acute neurological disorders, and has been proposed to underlie a number of chronic neurodegenerative diseases as well. Choi, D. W., *Neuron.*, 1:623 (1988); Choi, D. W., *Cerebrov. and Brain Metab. Rev.*, 2:105 (1990); Albers, G. W., et al., *Ann. NeuroL*, 25:398 (1989). Indeed, it is believed that glutamate neurotoxicity is involved in acute injury to the nervous system as observed with seizure, hypoxia, hypoglycemia, and trauma, as well as in chronic degenerative diseases such as Huntington's disease, olivopontocerebellar atrophy associated with glutamate dehydrogenase deficiency and decreased glutamate catabolism, amyotrophic lateral sclerosis/Parkinsonium-dementia, Parkinson's disease, and Alzheimer's disease. Choi, D. W., *Neuron*, 1:623–634 (1988); Choi, D. W., *Cereb. Brain Met., Rev.* 2:105–147 (1990); Courtier et al., *Lancet*, 341:265–268 (1993); Appel, S. H., *Trends Neurosci.*, 16:3–5 (1993).

In the mammalian brain, glutamate interacts with three major classes or receptors, i.e., N-methyl-D-aspartate ("NMDA") receptors, non-NMDA receptors and metabotropic receptors (Watkins, J. D., et al., *Trends Neurosci.*, 10:265 (1987); and Seeburg, *TIPS*, 141:297 (1993)). While triggering distinctive postsynaptic responses, all three classes of glutamate receptors can act to increase the intracellular concentration of free $Ca^{2+}$ in nerve cells (A. B. MacDermott, *Nature* 321:519 (1986)). Thus, binding of glutamate to the NMDA receptor opens a cation-selective channel that is markedly permeable to $Ca^{2+}$, leading to a large and rapid increase in intracellular $Ca^{2+}$. Although non-NMDA receptors are in most instances linked to cation channels that largely exclude calcium, they can indirectly promote $Ca^{2+}$ entry into neurons by depolarizing the cell membrane, which in turn opens voltage-activated $Ca^{2+}$-channels. The so-called "metabotropic receptor", on the other hand, is not associated with an ion channel but can promote the release of $Ca^{2+}$ from intracellular stores via the second-messenger inositol triphosphate.

Irrespective of the triggering mechanism, prolonged elevation of cytosolic $Ca^{2+}$ is believed to be a key event in the initiation of neuronal destruction. Adverse consequences of elevated intracellular $Ca^{2+}$ include derangement of mitochondrial respiration, activation of $Ca^{2+}$-dependent proteases, lipases and endonucleases, free radical formation and lipid peroxidation of the cell membrane.

The NMDA subtype of excitatory amino acid receptors is strongly involved in nerve cell death which occurs following brain or spinal chord ischemia. Upon the occurrence of ischemic brain insults such as stroke, heart attack or traumatic brain injury, an excessive release of endogenous glutamate occurs, resulting in the over-stimulation of NMDA receptors. Associated with the NMDA receptor is an ion channel. The recognition site, i.e., the NMDA receptor, is external to the ion channel. When glutamate interacts with the NMDA receptor, it causes the ion channel to open, thereby permitting a flow of cations across the cell membrane, e.g., $Ca^{2+}$ and $Na^+$ into the cell and $K^+$ out of the cell. It is believed that this flux of ions, especially the influx of $Ca^{2+}$ ions, caused by the interaction of glutamate with the NMDA receptor, plays an important role in nerve cell death. See, e.g., Rothman, S. M. and Olney, J. W., *Trends in Neurosci.*, 10(7):299–302 (1987). Additionally, excessive excitation of neurons occurs in epileptic seizures and it has been shown that over-activation of NMDA receptors contributes to the pathophysiology of epilepsy (Porter, R. J., *Epilepsia*, 30(Suppl. 1):S29–S34 (1989); and Rogawski, M. A., et al., *Pharmacol. Rev.*, 42:224–286 (1990)).

Non-NMDA receptors constitute a broad category of postsynaptic receptor sites which, as is the case for NMDA receptors, are directly linked to ion channels. Specifically, the receptor sites are physically part of specific ion channel proteins. Non-NMDA receptors have been broadly characterized into two major subclasses based on compounds selective therefor: kainate receptors and AMPA/quisqualate receptors. See J. C. Watkins et al., *Trends Neurosci.*, 10:265 (1987). AMPA is an abbreviation for α-amino-3-hydroxyl-5-methyl-4-isoazole propionic acid. These subclasses may be categorized as "non-NMDA" receptors.

Compared to NMDA receptors, non-NMDA receptors have received less pharmacological scrutiny—the existing antagonists are all competitive—and in vivo research in this area has been hampered by the lack of drugs that cross the blood-brain barrier. Nonetheless, in vivo studies have clearly demonstrate that non-NMDA receptor agonists can be as excitotoxic as NMDA agonists, although longer exposures can be required. In addition, evidence from animal studies and from human epidemiological studies suggests that excitotoxicity mediated by non-NMDA receptors may be clinically important in certain pathologies. See M. D. Ginsberg et al., *Stroke*, 20:1627 (1989).

One such disorder is global cerebral ischemia, as occurs following cardiac arrest, drowning, and carbon monoxide poisoning. Transient, severe interruption of the cerebral blood supply in animal causes a syndrome of selective neuronal necrosis, in which degeneration occurs among special populations of vulnerable neurons (including neocortical layers 3, 5 and 6, pyramidal cells in hippocampal zones CA1 and CA3, and small and medium sized striatal neurons). The time course of this degeneration is also regionally variable, and can range from a few hours (striatum) to several days (hippocampus).

NMDA antagonists generally have not proven highly effective in animal models of global ischemia; indeed, it has been suggested that positive results obtained using NMDA antagonists may largely be artifactual. In contrast, the competitive non-NMDA receptor antagonist 2,3-dihydroxy-6-nitro-7-sulfamoyl-benzo(F)quinoxaline ("NBQX") is dramatically effective in preventing delayed neuronal degeneration following transient forebrain ischemia in both gerbils and rats. See, M. J. Sheardown et al., *Science*, 247:571–574 (1990).

At present, there is a critical need for effective treatments which limit the extent of nerve cell death following a stroke or traumatic brain injury. Recent advances in the understanding of the mechanisms underlying this nerve cell death have led to the hope that a drug treatment can be developed. Research and development efforts in this area have focussed on blocking the actions of glutamate that are mediated by the NMDA receptor-channel complex. Two approaches have been developed: competitive NMDA receptor antagonists (Choi D. W., *Cerebrov. Brain Metab., Rev.* 1:165–211 (1990); Watkins, J. C. and Olverman, H. J., *Trends Neurosci.*, 10:265–272 (1987)) and blockers of the ion channel of the NMDA receptor-channel complex (Meldrum, B., *Cerebrovascular Brain Metab., Rev.* 2:27–57 (1987); Choi, D. W., *Cerebrovascular Brain Metab., Rev.* 2:105–147 (1987); and Kemp, J. A. etal., *Trends Neurosci.*, 10:265–272 (1987)). However, some toxicity with certain ion-channel-blockers such as MK-801 (see Merck Index, monograph 3392, 11th ed., 1989) has been reported. Olney, J. W. et al., *Science*, 244:1360–1362 (1989); Koek, W. and Colpaert, J., *J. Pharmacol. Exp. Ther.*, 252:349–357 (1990). NMDA antagonists also have been shown to inhibit memory acquisition. Morris, R. G. M., in *Excitat. A.A. 's in Health and Disease*, D. Lodge (ed.), Wiley, 297–320 (1988).

Blockers of neurotransmitter release have received some attention as potential neuroprotective agents. See Meldrum, B., *Cerebrovascular and Brain Metab., Rev.* 2: 27–57 (1990); Dolphin, A. C. *Nature*, 316:148–150 (1985)); Evans, M. C. et al., *Neurosci. Lett.*, 83:287–292 (1987); Ault, B. and Wang, C. M., *Br. J. Pharmacol.*, 87:695–703 (1986); Kaneko, T., et al., *Arzneim-Forsch./Drug Res.*, 39:445–450 (1989); Malgouris, C., et al., *J. Neurosci.*, 9:3720–3727 (1989); Jimonet, P. et al. *BioOrgan. and Med. Chem. Lett.*, 983–988 (1993); Wahl, F. et al., *Eur. J. Pharmacol.*, 230:209–214 (1993); Koek, J. W. and Colpaert, F. C., *J. PharmacoL Exp. Ther.*, 252:349–357 (1990); Kaneko, T. et al., *Arzneim.-Forsch./Drug Res.*, 39:445–450 (1989). Certain compounds said to inhibit glutamate release also have been reported to show anticonvulsant activity. Malgouris, C., et al., *J. Neurosci*, 9: 3720–3727 (1989); Miller, et al., *New Anticonvulsant Drugs*, Meldrum, B. S. and Porter R. J. (eds), London:John Libbey, 165–177 (1986).

Calcium antagonists such as nimodipine have been reported to act both as cerebral vasodilators (Wong, M. C. W. and Haley, E. C. Jr., *Stroke*, 24:31–36 (1989)), and to block calcium entry into neurons (Scriabine, A., *Adv. Neurosurg.* (1990)). Modest improvement in the outcome of stroke has been observed in clinical trials. Gelmers, H. J. et al., *N. Eng. J. Med.*, 318:203–207 (1988). While there are significant cardiovascular side effects, nimodipine appears less toxic than certain NMDA antagonists.

Antagonists of voltage-gated Na channels can exhibit neuroprotective properties. Graham, S. H., J. Chen, F. H. Sharp, and R. P. Simon, *J. Cereb. Blood Flow and Metab.*, 13:88–97 (1993), Meldrum, B. S., et al., *Brain Res.*, 593:1–6 and Stys, P. K., S. G. Waxman, and B. R. Ransom, *J. Neurosci.*, 12:430–439 (1992). In stroke, sustained hypoxia in the "core region" results from occlusion of the blood supply by a clot. As hypoxia develops, ATP depletion leads to an inability of the Na, K-ATPase to maintain the ion gradients which generate the normal membrane potential of resting nerve cells. As the cell depolarizes and reaches the threshold for action potential firing, Na channels are activated. Stys et al. (Stys, P. K., S. G. Waxman, and B. R. Ransom, *J. Neurosci.*, 12:430–439 (1992)) recently reported the development of Na channel hyperactivity in anoxia of central white matter and demonstrate in vitro the neuroprotective effect of the Na channel blockers tetrodotoxin (TTX) and saxitoxin (STX).

SUMMARY OF THE INVENTION

The present invention provides N,N'-diaryl substituted guanidines of Formula I:

wherein:

R and R$^1$ are each independently selected from the group consisting of hydrogen, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted aminoalkyl having from 1 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted alkylsulfonyl having from 1 to about 20 carbon atoms, substituted or unsubstituted carbocyclic aryl having at least about 5 ring atoms, substituted or unsubstituted aralkyl having at least about 5 ring atoms, or a substituted or unsubstituted heteroaromatic or heteroalicyclic group having from 1 to 3 rings, 3 to 8 ring members in each ring and from 1 to 3 hetero atoms;

Ar and Ar$^1$ are each independently selected from the group consisting of substituted or unsubstituted carbocyclic aryl having at least 5 carbon atoms, and substituted or unsubstituted heteroaromatic group having 1 to 3 rings, 3 to 8 ring members in each ring and from 1 to 3 hetero atoms; and pharmaceutically acceptable salts thereof.

Preferred compounds of the Formula I include those represented by Formula IA:

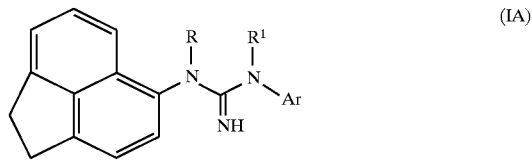

wherein:

R and R$^1$ are each independently hydrogen, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted aminoalkyl having from 1 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted alkylsulfonyl having from 1 to about 20 carbon atoms, substituted or unsubstituted carbocyclic aryl having at least about 5 ring atoms, substituted or unsubstituted aralkyl having at least about 5 ring atoms, or a substituted or unsubstituted heteroaromatic or heteroalicyclic group having from 1 to 3 rings, 3 to 8 ring members in each ring and from 1 to 3 hetero atoms;

Ar is selected from the group consisting of substituted or unsubstituted carbocyclic aryl having at least 5 carbon atoms, and substituted or unsubstituted heteroaromatic group having 1 to 3 rings, 3 to 8 ring members in each ring and from 1 to 3 hetero atoms; and pharmaceutically acceptable salts thereof.

Another group of preferred compounds of the present invention include those represented by Formula IB:

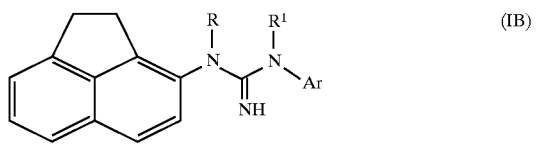

wherein R, R$^1$ and Ar are the same as defined above for Formula IA, and pharmaceutically acceptable salts thereof.

In another aspect, preferred compounds of Formula I include those guanidines having an N- and/or N'-acenaphtyl substituent that comprise one or more ring substituents. In particular, preferred compounds include those of the following Formula IIA:

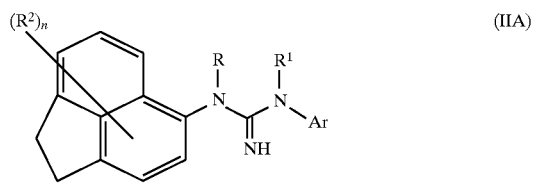

wherein R, R$^1$ and Ar are the same as defined above for Formula IA, each R$^2$ substituent is independently halogen, hydroxyl, cyano, isocyanato, nitro, amino, azido, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having 1 to about 20 carbon atoms, substituted or unsubstituted alkylthio having 1 to about 20 carbon atoms, substituted or unsubstituted alkylsulfinyl having 1 to about 20 carbon atoms, substituted or unsubstituted alkylsulfonyl having from 1 to about 20 carbon atoms, substituted or unsubstituted aminoalkyl having from 1 to about 20 carbon atoms, or substituted or unsubstituted aralkyl having at least about 5 ring atoms;

n is an integer equal to 1–9; and pharmaceutically acceptable salts thereof.

Also preferred are guanidines having a substituted 3-acenapthyl moiety, particularly compounds of the following Formula IIB

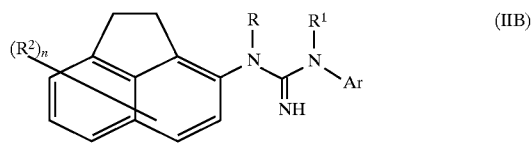

wherein R, R$^1$ and Ar are the same as defined above for Formula IA, each R$^2$ substituent is independently halogen, hydroxyl, cyano, isocyanato, nitro, amino, azido, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having 1 to about 20 carbon atoms, substituted or unsubstituted alkylthio having 1 to about 20 carbon atoms, substituted or unsubstituted alkylsulfinyl having 1 to about 20 carbon atoms, substituted or unsubstituted alkylsulfonyl having from 1 to about 20 carbon atoms, substituted or unsubstituted aminoalkyl having from 1 to about 20 carbon atoms, or substituted or unsubstituted aralkyl having at least about 5 ring atoms;

n is an integer equal to 1–9; and pharmaceutically acceptable salts thereof.

Preferred compounds of Formulas IIA or IIB include those where n is 1, 2 or 3, and more preferably n is 1 or 2. Compounds of Formula IIA or IIB are preferably substituted at the 3, 4, 5, 6, 7 and/or 8 positions of the acenaphthyl group by one or more R$^2$ groups.

Preferred compounds of Formula I, IA, IIB, IIA or IIB include disubstituted guanidines, i.e., where R and R$^1$ are each hydrogen, particularly where the group Ar and/or Ar$^1$ is a heterocyclic group or a substituted or unsubstituted carbocyclic aryl group such as unsubstituted and substituted biphenyl and unsubstituted or substituted phenyl including mono-substituted phenyl, di-substituted phenyl and tri-substituted phenyl. Also preferred are tri-substituted guanidines (i.e., where only one of R and R$^1$ are hydrogen) and tetrasubstituted guanidines (i.e., where both R and R$^1$ are other than hydrogen), particularly where the group Ar and/or Ar$^1$ is a heterocyclic group or a substituted or unsubstituted carbocyclic aryl group such as unsubstituted and substituted biphenyl and unsubstituted and substituted phenyl including mono-substituted phenyl, di-substituted phenyl and tri-substituted phenyl.

Compounds of the invention may exist as any one of a number of tautomeric forms. Each of these tautomeric forms are within the scope of the invention. That is, Formulas I, IA, IB, IIA and IIB include the tautomeric isomers of the specified guanidines.

Preferred compounds of the invention modulate, particularly inhibit, the release of a neurotransmitter, preferably glutamate. More preferably the preferred substituted guanidines modulate, particularly inhibit, neurotransmitter (e.g., glutamate) release from ischemic neuronal cells, especially mammalian cells such as human neuronal cells.

Most of the especially preferred guanidines of Formulas IA, IB, IIA or IIB above will be active in the K-evoked glutamate release assay and veratridine induced glutamate release assay, as discussed more fully infra. As described above, these especially preferred compounds include a 3-acenaphthyl or 5-acenaphthyl group on one guanidine nitrogen and either a substituted or unsubstituted aryl group, particularly a phenyl group, on the second guanidine nitrogen.

The N,N'-diaryl substituted guanidines of the present invention are useful for a number of therapeutic applications, including treatment of those diseases that result from modulation of a particular neurotransmitter system and that can be counteracted by one or more of the substituted guanidines of the invention which act either on the same or another class of neurotransmitters.

The present invention includes methods for treatment and/or prophylaxis of neurological conditions such as epilepsy, neurodegenerative conditions and/or nerve cell death resulting from hypoxia, hypoglycemia, brain or spinal chord ischemia, brain or spinal chord trauma, stroke, heart attack, drowning or carbon monoxide poisoning. Compounds of the invention also are useful to treat and/or prevent various neurodegenerative diseases such as Parkinson's disease, Huntington's disease, Amyotrophic Lateral Sclerosis, Alzheimer's disease, Down's Syndrome, Korsakoff's disease, olivopontocerebellar atrophy, HIV-induced dementia and blindness or multi-infarct dementia. Compounds of the invention also may be used to treat anxiety, e.g. by administration to subjects susceptible to generalized anxiety disorder. Compounds of the invention also will utility for the treatment of epilepsy. Compounds of the invention will have particular utility for treatment of global cerebral ischemia as may occur following cardiac arrest, drowning and carbon monoxide poisoning. The methods of treatment (which include prophylactic therapy) of the invention generally comprise administration of a therapeutically effective amount of one or more compounds of Formula I, IA, IB, IIA or IIB to an animal, including a mammal, particularly a human.

The invention also provides pharmaceutical compositions that comprise one or more compounds of Formula I and a suitable carrier.

DETAILED DESCRIPTION OF THE INVENTION

It has been found that compounds of the invention have the ability to modulate, i.e. inhibit or potentiate the release of neurotransmitter(s), or decrease or preferably lengthen the time course of action of neurotransmitter(s), from neuronal tissue. It has thus been found that the compounds will have utility to treat or prevent those pathophysiologic conditions which result from excessive or inadequate release of neurotransmitters. It is thought that substituted guanidines of the invention mediate the inhibition of neurotransmitter release by blocking presynaptic calcium channels and/or sodium channels. Accordingly, the invention provides methods for blockage of voltage sensitive calcium channels and sodium channels of neuronal cells, particularly mammalian cells such as human neuronal cells, comprising the administration to the cells an effective amount of a compound(s) of Formula I, IA, IB, IIA or IIB particularly such administration to a mammal in need of such treatment. By such blockage of calcium channels of neuronal cells, conditions associated with excessive endogenous neurotransmitter release can be treated.

More particularly, some disorders such as neuronal damage in stroke may be alleviated by inhibiting the release of excitatory amino acids such as glutamate. Some disorders such as depression may be alleviated by inhibiting the release of inhibitory neurotransmitters such as gamma-aminobutyric acid. Further and without wishing to be bound by theory, inhibiting the release of an excitatory neurotransmitter such as glutamate by administration of a compound of the invention may indirectly potentiate the release or subsequent actions of an inhibitory transmitter such as gamma-aminobutyric acid, and thus the compound of the invention may treat disorders known to be alleviated by more direct potentiation of inhibitory neurotransmission, e.g., anxiety or insomnia.

Compounds of the invention may be considered effective inhibitors of neurotransmitter release if the compound causes at least about a 50% inhibition of neurotransmitter, such as glutamate, at a concentration of about 100 $\mu$M according to the protocol disclosed in Example 64 below. More preferably the compound will cause at least about a 50% inhibition of neurotransmitter, such as glutamate, at a concentration of about 30 $\mu$M according to the protocol disclosed in Example 64 below.

Compounds of the invention may modulate release of neurotransmitters that include glutamate, dopamine, norepinephrine, glycine, aspartate and serotonin, particularly glutamate.

It has also been found that compounds of the invention, while effective modulators of neurotransmitter release as demonstrated e.g. in Example 64 which follows, exhibit relatively low affinity to the PCP and/or sigma receptors in typical PCP and sigma receptor binding assays. This suggests that compounds of the invention have a clearly distinct therapeutic mechanism of action relative to neuroprotective agents that exhibit high affinity for the PCP or sigma receptors.

Suitable halogen groups of compounds of the invention (including compounds of Formulas I, IA, IB, IIA or IIB) are F, Cl, Br and 1. Preferred alkyl groups include having 1 to about 12-carbon atoms, more preferably 1 to about 6 carbon atoms, such as methyl, ethyl, n-propyl, iso-propyl, n-butyl, t-butyl, iso-butyl, sec-butyl, pentyl and hexyl groups. Preferred alkenyl and alkynyl groups include those groups having one or more unsaturated linkages, preferably one or two unsaturated linkages and from 2 to about 12 carbon atoms, more preferably 2 to about 6 carbon atoms, still more preferably 2 to about 3 or 4 carbon atoms. Each of the terms alkyl, alkenyl and alkynyl as used herein refer to both cyclic and noncyclic groups, although typically straight or branched chain noncyclic groups are generally more preferred. Preferred alkoxy groups of compounds of the invention include groups having one or more oxygen linkages and from 1 to about 12 carbon atoms, more preferably 1 to about 8 carbon atoms, still more preferably 1 to about 6 carbons. Preferred thioalkyl groups include groups having one or more thioether linkages and from 1 to about 12 carbon atoms, more preferably 1 to about 8 carbon atoms, still more preferably 1 to about 6 carbons. Preferred aminoalkyl groups include those groups having one or more primary, secondary and/or tertiary amine groups, and from 1 to about 1-2 carbon atoms, more preferably 1 to about 8 carbon atoms, still more preferably 1 to about 6 carbons, and even more preferably 1–3 carbon atoms. Secondary and tertiary amine groups are generally more preferred than primary amine moieties. Preferred alkylsulfinyl groups have one or more sulfinyl (SO) groups, more typically one sulfinyl group, and from 1 to about 12 carbon atoms, more preferably 1 to about 6 carbons, and even more preferably 1–3 carbon atoms. Preferred alkylsulfonyl groups have one or more sulfono ($SO_2$) groups, more typically one sulfono group, and from 1 to about 12 carbon atoms, more preferably 1 to about 6 carbons, and even more preferably 1–3 carbon atoms. Suitable heteroaromatic or heteroaryl and heteroalicyclic groups of compounds of the invention contain 1–3 separate or fused rings and one or more N, O or S atoms and include, e.g., quinolinyl including 8-quinolinyl, indolinyl including 5-indolinyl, furyl, thienyl, pyrrolyl, thiazolyl, pyridyl, pyrimidinyl, pyridazinyl, oxazolyl and phthalimido groups all of which may be optionally independently substituted at one or more available positions including fused to a further cyclic group (e.g. fused to a benzene ring); and substituted or unsubstituted tetrahydrofuranyl, tetrahydropyranyl, piperidinyl, piperazinyl, morpholino, pyrrolidinyl groups, pyrazinyl, coumarinyl, tetrahydroquinolinyl, tetrahydroisoquinolinyl, benzothiazolyl, benzotriazolyl, and benzimidazolyl. Preferred aryl groups, including carbocyclic aryl groups, include those having about 5 to about 20 carbons, more preferably about 1 to 3 separate or fused rings and from 6 to about 18 carbon atoms, such as phenyl, naphthyl, acenaphthyl, phenanthryl, anthracyl and fluorene groups.

Said substituted moieties of compounds of the invention may be substituted at one or more available positions by one or more suitable groups such as, e.g., halogen such as F, Cl, Br, or l; cyano; hydroxyl; nitro; azido; carboxy; carbocyclic aryl; alkyl groups including alkyl groups having from 1 to about 12 carbon atoms or from 1 to about 6 carbon atoms; alkenyl and alkynyl groups including groups having one or more unsaturated linkages and from 2 to about 12 carbon atoms or from 2 to about 6 carbon atoms; alkoxy groups such as those groups having one or more oxygen linkages and from 1 to about 12 carbon atoms or from 1 to about 6 carbon atoms; thioalkyl groups such as those groups having one or more thioether linkages and from 1 to about 12 carbon atoms or from 1 to about 6 carbon atoms; aminoalkyl groups such as groups having one or more N atoms and from 1 to about 12 or 1 to about 6 carbon atoms; aminoalkylenearyl groups such as groups having one or more N atoms, such N atoms(s) by substitued by one or more alkylenearyl groups such as benzyl and the like with dibenzylamino being a particularly preferred substituent such as of phenyl or other aryl group; alkylsulfinyl such as those groups having one or more sulfinyl groups and from 1 to about 12 carbon atoms or from 1 to about 6 carbon atoms; alkylsulfonyl such as those groups having one or more sulfono groups and from 1 to about 12 carbon atoms or from 1 to about 6 carbon atoms. Further suitable and preferred substituted moieties of compounds are disclosed herein.

Specifically preferred substituted groups include carboxylic acyl or alkanoyl groups, preferably having from 1 to about 1 2 or 1 to about 6 carbon atoms such as acetyl, propanoyl, iso-propanoyl, butanoyl, sec-butanoyl, pentanoyl and hexanoyl groups. Also preferred substituted moieties are alkaryl groups which include single and multiple ring compounds, including multiple ring compounds that contain separate and/or fused aryl groups, e.g., above-mentioned aryl groups substituted by one or more $C_1$–$C_{12}$, $C_1$–$C_6$ or $C_1$–$C_4$ alkyl groups such as phenylethyl, phenylpropyl, phenylbutyl, phenylpentyl and phenylhexyl groups as well as the branched chain isomers thereof. aloalkyl are also preferred, particularly fluoroalkyl such as trifluoromethyl. Aroyl groups are also preferred substituted groups such as carbonyl substituted by phenyl, naphthyl, acenaphthyl, phenanthryl, and anthracyl groups and carboxylic acyl groups substituted by one or more aryl groups, e.g., diphenylacetoxy and fluorenecarboxy groups. Aralkanoyl groups are also preferred and include carbonyl substituted by the aralkyl groups described above. Aralkoxy groups are also preferred substituted groups and include alkoxy groups substituted by phenyl, naphthyl, acenaphthyl, phenanthryl, and anthracyl groups. Preferred substituted aryl groups include the above described aryl groups, particularly phenyl, substituted by halo, hydroxy, alkoxy, amino, and the like.

Particularly preferred substituent groups of compounds of the invention include halogen, hydroxy, $CF_3$, $C^1$–$C^6$ acyl, $C_1$–$C_6$ alkyl, $C_2$–$C_6$ alkenyl, $C_2$-$C_6$ alkynyl, $C_1$–$C_6$ alkoxy, $C_6$–$C_{18}$ aryl, $C_2$–$C_6$ dialkoxymethyl, cyano, $C_3$–$C_6$ cycloalkyl, $C_3$–$C_6$ heterocycloalkyl, $C_3$–$C_{15}$ dialkylaminoalkyl, carboxy, $C_2$–$C_6$ carboxylic acid, carboxamido, $C^1$–$C_6$ haloalkyl, $C^1$–$C_6$ haloalkylthio, allyl, $C_7$–$C_{20}$ aralkyl, a $C_3$–$C_6$ heterocycloalkyl ring fused to a benzene ring, $C^1$–$C_6$ alkylthio, arylthio, $C^1$–$C_6$ haloalkoxy, amino, $C^1$–$C_6$ alkylamino, $C_2$–$C_{15}$ dialkylamino, carbamoyl, $C^1$–$C_6$ N-alkylcarbamoyl, $C_2$–$C_{15}$ N,N-dialkylcarbamoyl, nitro, $C_2$–$C_{15}$ dialkylsulfamoyl, and the like.

Particularly preferred R and $R^1$ groups of compounds of the invention include hydrogen and substituted and unsubstituted alkyl, particularly methyl, ethyl, propyl and butyl. Hydrogen and methyl and ethyl are especially preferred R and $R^1$ groups.

Preferred $R^2$ groups of compounds of the invention include halo, substituted or unsubstituted alkyl, substituted or unsubstituted minoalkyl, substituted or unsubstituted alkoxy, substituted or unsubstituted alkylthio, and substituted or unsubstituted alkylsulfinyl. Preferred substituted alkyl $R^2$ groups include haloalkyl including fluoroalkyl such as fluoromethyl or fluoroethyl, particularly trifluoromethyl.

Typically preferred Ar substituents of compounds of Formula I, IA, IB, IIA or IIB are substituted and unsubstituted carboxylic groups, especially substituted and unsubstituted phenyl groups. Phenyl groups having from 1 to 5 ring substitutents are particularly preferred including phenyl groups having a single ring substituent e.g. at the 3 or 4 position; disubstituted phenyl groups including a 2,3-substituted phenyl group, 2,4-substituted phenyl group, 2,5-substituted phenyl group, 2,6-substituted phenyl group, a 3,4-substituted phenyl group or a 3,5-substituted phenyl group; and trisubstituted phenyl groups including a 2,3,4-substituted phenyl group, a 2,3,5-substituted phenyl group, a 2,3,6-substituted phenyl group and a 3,4,5-substituted phenyl group; and tetrasubstituted phenyl groups including a 2,3,4,5-substituted phenyl group, a 2,3,4,6-substituted pheny group and a 2,3,5,6-substituted phenyl group. Preferred ring substituents of such substituted phenyl Ar groups include halogen, nitro, alkyl including alkyl having 1 to about 8 carbon atoms such as methyl, ethyl, propyl, butyl, pentyl, hexyl, etc., alkoxy including alkoxy having 1 to about 8 carbon atoms such as methoxy, ethoxy, propoxy, butoxy, etc., alkylthio such as methylthio and ethylthio, haloalkyl such as fluoroalkyl including trifluromethyl, chloroalkyl and bromoalkyl, haloalkoxy including fluoroalkoxy such as trifluoromethoxy, and carobocyclic aryl, particularly substituted or unsubstituted phenyl.

Specifically preferred Ar and/or $Ar^1$ groups for Formula I, IA, IB, IIA, or IIB include the following: halophenyl such as fluorophenyl, chlorophenyl, bromophenyl and iodophenyl including 2,5-dibromophenyl, 4-chlorophenyl, 2,3-dichlorophenyl, 3,4-dichlorophenyl, 2,3,4-trichlorophenyl, 3,4,5-trichlorophenyl, 2,3,4,5-tetrachlorophenyl, 2,3,5,6-tetrachlorophenyl, 3-iodophenyl, and the like; alkylphenyl such as 2,3-dimethylphenyl, 3-isopropylphenyl, tert-butylphenyl including 3-tert-butylphenyl, 4-tert-butylphenyl, cyclohexylphenyl including 4-cyclohexylphenyl, sec-butylphenyl including 4-sec-butylphenyl, adamantylphenyl including 3-adamantylphenyl and 4-adamantylphenyl, and the like; haloalkylphenyl including fluoro, bromo, and chloroalkylphenyl such as trifluoromethylphenyl, particularly 4-trifluoromethylphenyl; alkoxyphenyl including 4-methoxyphenyl, 3,4-dimethoxyphenyl, 4-n-butoxyphenyl and the like; nitrophenyl such as 3-nitrophenyl, 4-nitrophenyl and the like; substituted and unsubstituted bi-phenyl such as 2-bi-phenyl, 3-bi-phenyl, 4-bi-phenyl and the like; substituted and unsubstituted aralkylphenyl including aralkylphenyl having 1 to about 10 about carbon atoms and preferably an aryl substituent of phenyl such as e.g. (1'-methyl-2'-phenylethyl)phenyl (i.e., $C_6H_5$-$CH_2CH(CH_3)$ $C_6H_5$—) such as 3-(1'-methyl-2'-phenylethyl)phenyl and 4-(1'-methyl-2'-phenylethyl)phenyl, phenethylphenyl (i.e. $C_6H_5CH_2CH_2C_6H_5$—) such as 3-phenethylphenyl and 4-phenethylphenyl and the like; substituted and unsubstituted aralkylaminophenyl such as e.g. (mono-phenyl$C_{1-6}$alkylene)aminophenyl or (di-phenyl$C_{1-6}$alkylene)aminophenyl such as (N,N-dibenzyl)aminophenyl, (N,N-diphenethylene)aminophenyl, N-methyl-N-benzylaminophenyl, and the like; substituted and unsubstituted aryloxyphenyl and aralkyloxyphenyl including substituted and unsubstituted phenoxyphenyl and benzyloxyphenyl such as e.g. 4-benzyloxyphenyl, 3-benzyloxyphenyl, dibenzyloxyphenyl such as 3-dibenzyloxyphenyl and 4-dibenzyloxyphenyl, and the like; substituted and unsubstituted (alkyleneoxyaryl)phenyl such as ($C_{1-6}$alkyleneoxyaryl)phenyl, particularly substituted and unsubstituted ($C_{1-6}$alkyleneoxyphenyl)phenyl such as substituted or unsubstituted benzyloxymethylenephenyl including such groups having one or more $C_{1-6}$alkyl, halo-$C_{1-6}$alkylhalo, alkoxy, alkylthio or nitro benzyl ring substituents; substituted and unsubstituted heterocyclic-substituted phenyl, particularly heteroaromatic-substituted phenyl such as e.g. phenyl substituted by indole such as 3-(2'-indole)phenyl and 4-(2'-indole)phenyl, phenyl substituted by benzothiazole such as 3-(2'-benzothiazole)phenyl, 4-(2-benzothiazole)phenyl, 3-(2'-benzothiazole-6'-methyl)phenyl, 4-(2-benzothiazole-6'-methyl)phenyl, and phenyl substituted by one or more indolinyl including 5-indolinyl, furyl, thienyl, pyrrolyl, thiazolyl, pyridyl, pyrimidinyl, pyridazinyl, oxazolyl and phthalimido groups (all of which may be optionally independently substituted at one or more available positions including fused to a further cyclic group (e.g. fused to a benzene ring)), as well as phenyl substituted by one or more substituted or unsubstituted tetrahydrofuranyl, tetrahydropyranyl, piperidinyl, piperazinyl, morpholino, pyrrolidinyl groups, pyrazinyl, coumarinyl, tetrahydroquinolinyl, tetrahydroisoquinolinyl, benzothiazolyl, and benzimidazolyl. Typically preferred heteroaromatic-substituted phenyl substituents include those phenyl substituents independently substituted at one or more ring positions, more typically one or two phenyl ring positions, by heteroaromatic group(s) that each contains 1-3 rings, 3 to 8 ring members in each ring and 1–3 N, O or S atoms.

Suitable Ar and/or $Ar^1$ groups of Formula I, IA, IB, IIA, or IIB also include substituted and unsubstituted naphthyl; and substituted and unsubstituted acenaphthyl including 3-acenaphthyl and 5-acenaphthyl.

Specifically preferred compounds of the invention include:
N-(5-acenaphthyl)-N'-(2,3,4-trichlorophenyl)guanidine;
N-(5-acenaphthyl)-N'-(2,3,4-trichlorophenyl)-N-methylguanidine;
N-(5-acenaphthyl)-N'-(2,3,4-trichlorophenyl)-N'-methylguanidine;
N-(5-acenaphthyl)-N'-(2,3,4-trichlorophenyl)-N,N'-bis-metyhylguanidine;
N,N'-bis(5-acenaphthyl)-N-methylguanidine;
N,N'-bis(5-acenaphthyl)-N,N'-bis-methylguanidine;
N-(5-acenaphthyl)-N'-(1-anthracenyl)guanidine;
N-(5-acenaphthyl)-N'-(1-anthracenyl)-N-methylguanidine;
N-(5-acenaphthyl)-N'-(1-anthracenyl)-N'-methylguanidine;
N-(5-acenaphthyl)-N'-(1-anthracenyl)-N,N'-bis-methylguanidine;
N-(5-acenaphthyl)-N'-(4-tert-butylphenyl)guanidine;
N-(5-acenaphthyl)-N'-(4-tert-butylphenyl)-N-methylguanidine;
N-(5-acenaphthyl)-N'-(4-tert-butylphenyl)-N'-methylguanidine;
N-(5-acenaphthyl)-N'-(4-tert-butylphenyl)-N,N'-bis-methylguanidine;
N-(5-acenaphthyl)-N'-(4-cyclohexylphenyl)guanidine;
N-(5-acenaphthyl)-N'-(4-cyclohexylphenyl)-N-methylguanidine;
N-(5-acenaphthyl)-N'-(4-cyclohexylphenyl)-N'-methylguanidine;
N-(5-acenaphthyl)-N'-(4-cyclohexylphenyl)-N,N'-bis-methylguanidine;
N-(5-acenaphthyl)-N'-(4-sec-butylphenyl)guanidine;
N-(5-acenaphthyl)-N'-(4-sec-butylphenyl)-N-methylguanidine;
N-(5-acenaphthyl)-N'-(4-sec-butylphenyl)-N'-methylguanidine;
N-(5-acenaphthyl)-N'-(4-sec-butylphenyl)-N,N'-bis-methylguanidine;
N-(5-acenaphthyl)-N'-(4-methoxyphenyl)guanidine;
N-(5-acenaphthyl)-N'-(4-methoxyphenyl)-N-methylguanidine;
N-(5-acenaphthyl)-N'-(4-methoxyphenyl)-N'-methylguanidine;
N-(5-acenaphthyl)-N'-(4-methoxyphenyl)-N,N'-bis-methylguanidine;
N-(5-acenaphthyl)-N'-(2,3-dichlorophenyl)guanidine;
N-(5-acenaphthyl)-N'-(2,3-dichlorophenyl)-N-methylguanidine;
N-(5-acenaphthyl)-N'-(2,3-dichlorophenyl)-N'-methylguanidine;
N-(5-acenaphthyl)-N'-(2,3-dichlorophenyl)-N,N'-bis-methylguanidine;
N-(5-acenaphthyl)-N'-(4-methoxy-2-naphthyl)guanidine;
N-(5-acenaphthyl)-N'-(4-methoxy-2-naphthyl)-N-methylguanidine;
N-(5-acenaphthyl)-N'-(4-methoxy-2-naphthyl)-N'-methylguanidine;
N-(5-acenaphthyl)-N'-(4-methoxy-2-naphthyl)-N,N'-bis-methylguanidine;
N-(5-acenaphthyl)-N'-(3,4-dichlorophenyl)guanidine;
N-(5-acenaphthyl)-N'-(3,4-dichlorophenyl)-N-methylguanidine;
N-(5-acenaphthyl)-N'-(3,4-dichlorophenyl)-N'-methylguanidine;
N-(5-acenaphthyl)-N'-(3,4-dichlorophenyl)-N,N'-bis-methylguanidine;
N-(5-acenaphthyl)-N'-(4-chlorophenyl)guanidine;
N-(5-acenaphthyl)-N'-(4-chlorophenyl)-N-methylguanidine;
N-(5-acenaphthyl)-N'-(4-chlorophenyl)-N'-methylguanidine;
N-(5-acenaphthyl)-N'-(4-chlorophenyl)-N,N'-bis-methylguanidine;
N-(5-acenaphthyl)-N'-(2-naphthyl)guanidine;
N-(5-acenaphthyl)-N'-(2-naphthyl)-N-methylguanidine;
N-(5-acenaphthyl)-N'-(2-naphthyl)-N'-methylguanidine;
N-(5-acenaphthyl)-N'-(2-naphthyl)-N,N'-bis-methylguanidine;
N-(5-acenaphthyl)-N'-(6-quinolinyl)guanidine;
N-(5-acenaphthyl)-N'-(6-quinolinyl)-N-methylguanidine;

N-(5-acenaphthyl)-N'-(6-quinolinyl)-N'-methylguanidine;
N-(5-acenaphthyl)-N'-(6-quinolinyl)-N,N'-bis-methylguanidine;
N-(5-acenaphthyl)-N'-(4-nitrophenyl) guanidine;
N-(5-acenaphthyl)-N'-(4-nitrophenyl)-N-methylguanidine;
N-(5-acenaphthyl)-N'-(4-nitrophenyl)-N'-methylguanidine;
N-(5-acenaphthyl)-N'-(4-nitrophenyl)-N,N'-bis-methylguanidine;
N-(5-acenaphthyl-N'-(3-bi-phenyl)guanidine;
N-(5-acenaphthyl-N'-(3-bi-phenyl)-N-methylguanidine;
N-(5-acenaphthyl-N'-(3-bi-phenyl)-N'-methylguanidine;
N-(5-acenaphthyl-N'-(3-bi-phenyl)-N,N'-bis-methylguanidine;
N-(5-acenaphthyl)-N'-(2,3-dimethylphenyl)guanidine;
N-(5-acenaphthyl)-N'-(2,3-dimethylphenyl)-N-methylguanidine;
N-(5-acenaphthyl)-N'-(2,3-dimethylphenyl)-N'-methylguanidine;
N-(5-acenaphthyl)-N'-(2,3-dimethylphenyl)-N,N'-bis-methylguanidine;
N-(5-acenaphthyl)-N'-(2-bi-phenyl)guanidine;
N-(5-acenaphthyl)-N'-(2-bi-phenyl)-N-methylguanidine;
N-(5-acenaphthyl)-N'-(2-bi-phenyl)-N'-methylguanidine;
N-(5-acenaphthyl)-N'-(2-bi-phenyl)-N,N'-bis-methylguanidine;
N-(5-acenaphthyl)-N'-(2,5-dibromophenyl)guanidine;
N-(5-acenaphthyl)-N'-(2,5-dibromophenyl)-N-methylguanidine;
N-(5-acenaphthyl)-N'-(2,5-d ibromophenyl)-N'-methylguanidine;
N-(5-acenaphthyl)-N'-(2,5-dibromophenyl)-N,N'-bis-methylguanidine;
N-(5-acenaphthyl)-N'-(3,4-dimethoxyphenyl)guanidine;
N-(5-acenaphthyl)-N'-(3,4-dimethoxyphenyl)-N-methylguanidine;
N-(5-acenaphthyl)-N'-(3,4-dimethoxyphenyl)-N'-methylguanidine;
N-(5-acenaphthyl)-N'-(3,4-dimethoxyphenyl)-N,N'-bis-methylguanidine;
N-(5-acenaphthyl)-N'-(4-methoxy-1-naphthyl)-N-methylguanidine;
N-(5-acenaphthyl)-N'-(4-methoxy-1-naphthyl)-N'-methylguanidine;
N-(5-acenaphthyl)-N'-(4-methoxy-1-naphthyl)-N,N'-dimethylguanidine;
N-(5-acenaphthyl)-N'-(4-chloro-1-naphthyl)guanidine;
N-(5-acenaphthyl)-N'-(4-chloro-1-naphthyl)-N-methylguanidine;
N-(5-acenaphthyl)-N'-(4-chloro-1-naphthyl)-N'-methylguanidine;
N-(5-acenaphthyl)-N'-(4-chloro-1-naphthyl)-N,N'-bis-methylguanidine;
N-(5-acenaphthyl)-N'-(3,4,5-trichlorophenyl)guanidine;
N-(5-acenaphthyl)-N'-(3,4,5-trichlorophenyl)-N-methylguanidine;
N-(5-acenaphthyl)-N'-(3,4,5-trichlorophenyl)-N'-methylguanidine;
N-(5-acenaphthyl)-N'-(3,4,5-trichlorophenyl)-N,N'-bis-methylguanidine;
N-(5-acenaphthyl)-N'-(4-bi-phenyl)guanidine;
N-(5-acenaphthyl)-N'-(4-bi-phenyl)-N-methylguanidine;
N-(5-acenaphthyl)-N'-(4-bi-phenyl)-N'-methylguanidine;
N-(5-acenaphthyl)-N'-(4-bi-phenyl)-N,N'-bis-methylguanidine;
N-(5-acenaphthyl)-N'-(2,3,4,5-tetrachlorophenyl)guanidine;
N-(5-acenaphthyl)-N'-(2,3,4,5-tetrachlorophenyl)-N-methylguanidine;
N-(5-acenaphthyl)-N'-(2,3,4,5-tetrachlorophenyl)-N'-methylguanidine;
N-(5-acenaphthyl)-N'-(2,3,4,5-tetrachlorophenyl)-N,N'-bis-methylguanidine;
N-(5-acenaphthyl)-N'-(3-isopropylphenyl)guanidine;
N-(5-acenaphthyl)-N'-(3-isopropylphenyl)-N-methylguanidine;
N-(5-acenaphthyl)-N'-(3-isopropylphenyl)-N'-methylguanidine;
N-(5-acenaphthyl)-N'-(3-isopropylphenyl)-N,N'-bis-methylguanidine;
N-(5-acenaphthyl)-N'-(3-tert-butylphenyl)guanidine;
N-(5-acenaphthyl)-N'-(3-tert-butylphenyl)-N-methylguanidine;
N-(5-acenaphthyl)-N'-(3-tert-butylphenyl)-N'-methylguanidine;
N-(5-acenaphthyl)-N'-(3-tert-butylphenyl)-N,N'-bis-methylguanidine;
N-(5-acenaphthyl)-N'-(2,3,5,6-tetrachlorophenyl)guanidine;
N-(5-acenaphthyl)-N'-(2,3,5,6-tetrachlorophenyl)-N-methylguanidine;
N-(5-acenaphthyl)-N'-(2,3,5,6-tetrachlorophenyl)-N'-methylguanidine;
N-(5-acenaphthyl)-N'-(2,3,5,6-tetrachlorophenyl)-N,N'-bis-methylguanidine;
N-(5-acenaphthyl)-N'-(3-iodophenyl)guanidine;
N-(5-acenaphthyl)-N'-(3-iodophenyl)-N-methylguanidine;
N-(5-acenaphthyl)-N'-(3-iodophenyl)-N'-methylguanidine;
N-(5-acenaphthyl)-N'-(3-iodophenyl)-N,N'-bis-methylguanidine;
N-(5-acenaphthyl)-N'-(3-nitrophenyl)guanidine;
N-(5-acenaphthyl)-N'-(3-nitrophenyl)-N-methylguanidine;
N-(5-acenaphthyl)-N'-(3-nitrophenyl)-N'-methylguanidine;
N-(5-acenaphthyl)-N'-(3-nitrophenyl)-N,N'-bis-methylguanidine;
N-(5-acenaphthyl)-N'-(5-indolinyl)guanidine;
N-(5-acenaphthyl)-N'-(5-indolinyl)-N-methylguanidine;
N-(5-acenaphthyl)-N'-(5-indolinyl)-N'-methylguanidine;
N-(5-acenaphthyl)-N'-(5-indolinyl)-N,N'-bis-methylguanidine;
N-(5-acenaphthyl)-N'-(3-acenaphthyl)guanidine;
N-(5-acenaphthyl)-N'-(3-acenaphthyl)-N-methylguanidine;
N-(5-acenaphthyl)-N'-(3-acenaphthyl)-N'-methylguanidine;
N-(5-acenaphthyl)-N'-(3-acenaphthyl)-N,N'-bis-methylguanidine;
N-(5-acenaphthy)-N'-(2-fluorenyl)guanidine;
N-(5-acenaphthy)-N'-(2-fluorenyl)-N-methyfguanidine;
N-(5-acenaphthy)-N'-(2-fluorenyl)-N'-methylguanidine;
N-(5-acenaphthy)-N'-(2-fluorenyl)-N,N'-bis-methylguanidine;
N-(5-acenaphthyl)-N'-(4-n-butoxyphenyl)guanidine;
N-(5-acenaphthyl)-N'-(4-n-butoxyphenyl)-N-methylguanidine;
N-(5-acenaphthyl)-N'-(4-n-butoxyphenyl)-N'-methylguanidine;
N-(5-acenaphthyl)-N'-(4-n-butoxyphenyl)-N,N'-bis-methylguanidine;
N-(5-acenaphthyl)-N'-(3-(2-methoxy)dibenzofuranyl) guanidine;
N-(5-acenaphthyl)-N'-(3-(2-methoxy)dibenzofuranyl)-N-methylguanidine;
N-(5-acenaphthyl)-N'-(3-(2-methoxy)dibenzofuranyl)-N'-methylguanidine;
N-(5-acenaphthyl)-N'-(3-(2-methoxy)dibenzofuranyl)-N,N'-bis-methylguanidine;
N-(5-acenaphthyl)-N'-(9-hydroxy-2-fluorenyl)guanidine;
N-(5-acenaphthyl)-N'-(9-hydroxy-2-fluorenyl)-N-methylguanidine;

N-(5-acenaphthyl)-N'-(9-hydroxy-2-fluorenyl)-N'-methylguanidine;
N-(5-acenaphthyl)-N'-(9-hydroxy-2-fluorenyl)-N,N'-bis-methylguanidine;
N-(5-acenaphthyl)-N'-(4-trifluoromethylphenyl)guanidine;
N-(5-acenaphthyl)-N'-(4-trifluoromethylphenyl)-N-methylguanidine;
N-(5-acenaphthyl)-N'-(4-trifluoromethylphenyl)-N'-methylguanidine;
N-(5-acenaphthyl)-N'-(4-trifluoromethylphenyl)-N,N'-bis-methylguanidine; N-(5-acenaphthyl)-N'-(4-methylthiophenyl)guanidine;
N-(5-acenaphthyl)-N'-(4-methylthiophenyl)-N-methylguanidine;
N-(5-acenaphthyl)-N'-(4-methylthiophenyl)-N'-methylguanidine;
N-(5-acenaphthyl)-N'-(4-methylthiophenyl)-N,N'-bis-methylguanidine;
N-(5-acenaphthyl)-N'-(3-sec-butylphenyl)guanidine;
N-(5-acenaphthyl)-N'-(3-sec-butylphenyl)-N-methylguanidine;
N-(5-acenaphthyl)-N'-(3-sec-butylphenyl)-N'-methylguanidine;
N-(5-acenaphthyl)-N'-(3-sec-butylphenyl)-N,N'-bis-methylguanidine;
N-(3-acenaphthyl)-N'-(2,3,4-trichlorophenyl)guanidine;
N-(3-acenaphthyl)-N'-(2,3,4-trichlorophenyl)-N-methylguanidine;
N-(3-acenaphthyl)-N'-(2,3,4-trichlorophenyl)-N'-methylguanidine;
N-(3-acenaphthyl)-N'-(2,3,4-trichlorophenyl)-N,N'-bis-methylguanidine;
N,N'-bis(3-acenaphthyl)-N-methylguanidine;
N,N'-bis(3-acenaphthyl)-N,N'-bis-methylguanidine;
N-(3-acenaphthyl)-N'-(1-anthracenyl)guanidine;
N-(3-acenaphthyl)-N'-(1-anthracenyl)-N-methylguanidine;
N-(3-acenaphthyl)-N'-(1-anthracenyl)-N'-methylguanidine;
N-(3-acenaphthyl)-N'-(1-anthracenyl)-N,N'-bis-methylguanidine;
N-(3-acenaphthyl)-N'-(4-tert-butylphenyl)guanidine;
N-(3-acenaphthyl)-N'-(4-tert-butylphenyl)-N-methylguanidine;
N-(3-acenaphthyl)-N'-(4-tert-butylphenyl)-N'-methylguanidine;
N-(3-acenaphthyl)-N'-(4-tert-butylphenyl)-N,N'-bis-methylguanidine;
N-(3-acenaphthyl)-N'-(4-cyclohexylphenyl)guanidine;
N-(3-acenaphthyl)-N'-(4-cyclohexylphenyl)-N-methylguanidine;
N-(3-acenaphthyl)-N'-(4-cyclohexylphenyl)-N'-methylguanidine;
N-(3-acenaphthyl)-N'-(4-cyclohexylphenyl)-N,N'-bis-methylguanidine;
N-(3-acenaphthyl)-N'-(4-sec-butylphenyl)guanidine;
N-(3-acenaphthyl)-N'-(4-sec-butylphenyl)-N-methylguanidine;
N-(3-acenaphthyl)-N'-(4-sec-butylphenyl)-N'-methylguanidine;
N-(3-acenaphthyl)-N'-(4-sec-butylphenyl)-N,N'-bis-methylguanidine;
N-(3-acenaphthyl)-N'-(4-methoxyphenyl)guanidine;
N-(3-acenaphthyl)-N'-(4-methoxyphenyl)-N-methylguanidine;
N-(3-acenaphthyl)-N'-(4-methoxyphenyl)-N'-methylguanidine;
N-(3-acenaphthyl)-N'-(4-methoxyphenyl)-N,N'-bis-methylguanidine;
N-(3-acenaphthyl)-N'-(2,3-dichlorophenyl)guanidine;
N-(3-acenaphthyl)-N'-(2,3-dichlorophenyl)-N-methylguanidine;
N-(3-acenaphthyl)-N'-(2,3-dichlorophenyl)-N'-methylguanidine;
N-(3-acenaphthyl)-N'-(2,3-dichlorophenyl)-N,N'-bis-methylguanidine;
N-(3-acenaphthyl)-N'-(4-methoxy-2-naphthyl)guanidine;
N-(3-acenaphthyl)-N'-(4-methoxy-2-naphthyl)-N-methylguanidine;
N-(3-acenaphthyl)-N'-(4-methoxy-2-naphthyl)-N'-methylguanidine;
N-(3-acenaphthyl)-N'-(4-methoxy-2-naphthyl)-N,N'-bis-methylguanidine;
N-(3-acenaphthyl)-N'-(3,4-dichlorophenyl)guanidine;
N-(3-acenaphthyl)-N'-(3,4-dichlorophenyl)-N-methylguanidine;
N-(3-acenaphthyl)-N'-(3,4-dichlorophenyl)-N'-methylguanidine;
N-(3-acenaphthyl)-N'-(3,4-dichlorophenyl)-N,N'-bis-methylguanidine;
N-(3-acenaphthyl)-N'-(4-chlorophenyl)guanidine;
N-(3-acenaphthyi)-N'-(4-chlorophenyl)-N-methylguanidine;
N-(3-acenaphthyl)-N'-(4-chlorophenyl)-N'-methylguanidine;
N-(3-acenaphthyl)-N'-(4-chlorophenyl)-N,N'-bis-methylguanidine;
N-(3-acenaphthyl)-N'-(2-naphthyl)guanidine;
N-(3-acenaphthyl)-N'-(2-naphthyl)-N-methylguanidine;
N-(3-acenaphthyl)-N'-(2-naphthyl)-N'-methylguanidine;
N-(3-acenaphthyl)-N'-(2-naphthyl)-N,N'-bis-methylguanidine;
N-(3-acenaphthyl)-N'-(6-quinolinyl)guanidine;
N-(3-acenaphthyl)-N'-(6-quinolinyl)-N-methylguanidine;
N-(3-acenaphthyl)-N'-(6-quinolinyl)-N'-methylguanidine;
N-(3-acenaphthyl)-N'-(6-quinolinyl)-N,N'-bis-methylguanidine;
N-(3-acenaphthyl)-N'-(4-nitrophenyl)guanidine;
N-(3-acenaphthyl)-N'-(4-nitrophenyl)-N-methylguanidine;
N-(3-acenaphthyl)-N'-(4-nitrophenyl)-N'-methylguanidine;
N-(3-acenaphthyl)-N'-(4-nitrophenyl)-N,N'-bis-methylguanidine;
N-(3-acenaphthyl-N'-(3-bi-phenyl)guanidine;
N-(3-acenaphthyl-N'-(3-bi-phenyl)-N-methylguanidine;
N-(3-acenaphthyl-N'-(3-bi-phenyl)-N'-methylguanidine;
N-(3-acenaphthyl-N'-(3-bi-phenyl)-N,N'-bis-methylguanidine;
N-(3-acenaphthyl)-N'-(2,3-dimethylphenyl)guanidine;
N-(3-acenaphthyl)-N'-(2,3-dimethylphenyl)-N-methylguanidine;
N-(3-acenaphthyl)-N'-(2,3-dimethylphenyl)-N'-methylguanidine;
N-(3-acenaphthyl)-N'-(2,3-dimethylphenyl)-N,N'-bis-methylguanidine;
N-(3-acenaphthyl)-N'-(2-bi-phenyl)guanidine;
N-(3-acenaphthyl)-N'-(2-bi-phenyl)-N-methylguanidine;
N-(3-acenaphthyl)-N'-(2-bi-phenyl)-N'-methylguanidine;
N-(3-acenaphthyl)-N'-(2-bi-phenyl)-N,N'-bis-methylguanidine;
N-(3-acenaphthyl)-N'-(2,5-dibromophenyl)guanidine;
N-(3-acenaphthyl)-N'-(2,5-dibromophenyl)-N-methylguanidine;
N-(3-acenaphthyl)-N'-(2,5-dibromophenyl)-N'-methylguanidine;
N-(3-acenaphthyl)-N'-(2,5-dibromophenyl)-N,N'-bis-methylguanidine;

N-(3-acenaphthyl )-N'-(3,4-dimethoxyphenyl)guanidine;
N-(3-acenaphthyl)-N'-(3,4-dimethoxyphenyl)-N-methylguanidine;
N-(3-acenaphthyl)-N'-(3,4-dimethoxyphenyl)-N'-methylguanidine;
N-(3-acenaphthyl)-N'-(3,4-dimethoxyphenyl)-N,N'-bis-methylguanidine;
N-(3-acenaphthyl)-N'-(4-methoxy-1-naphthyl)-N-methylguanidine;
N-(3-acenaphthyl)-N'-(4-methoxy-1-naphthyl)-N'-methylguanidine;
N-(3-acenaphthyl)-N'-(4-methoxy-1-naphthyl)-N,N'-dimethylguanidine;
N-(3-acenaphthyl)-N'-(4-chloro-1-naphthyl)guanidine;
N-(3-acenaphthyl)-N'-(4-chloro-1-naphthyl)-N-methylguanidine;
N-(3-acenaphthyl)-N'-(4-chloro-1-naphthyl)-N'-methylguanidine;
N-(3-acenaphthyl)-N'-(4-chloro-1-naphthyl)-N,N'-bis-methylguanidine;
N-(3-acenaphthyl)-N'-(3,4,5-trichlorophenyl)guanidine;
N-(3-acenaphthyl)-N'-(3,4,5-trichlorophenyl)-N-methylguanidine;
N-(3-acenaphthyl)-N'-(3,4,5-trichlorophenyl)-N'-methylguanidine;
N-(3-acenaphthyl)-N'-(3,4,5-trichlorophenyl)-N,N'-bis-methylguanidine;
N-(3-acenaphthyl)-N'-(4-bi-phenyl)guanidine;
N-(3-acenaphthyl)-N'-(4-bi-phenyl)-N-methylguanidine;
N-(3-acenaphthyl)-N'-(4-bi-phenyl)-N'-methylguanidine;
N-(3-acenaphthyl)-N'-(4-bi-phenyl)-N,N'-bis-methylguanidine;
N-(3-acenaphthyl)-N'-(2,3,4,5-tetrachlorophenyl)guanidine;
N-(3-acenaphthyl)-N'-(2,3,4,5-tetrachlorophenyl)-N-methylguanidine;
N-(3-acenaphthyl)-N'-(2,3,4,5-tetrachlorophenyl)-N'-methylguanidine;
N-(3-acenaphthyl)-N'-(2,3,4,5-tetrachlorophenyl)-N,N'-bis-methylguanidine;
N-(3-acenaphthyl)-N'-(3-isopropylphenyl)guanidine;
N-(3-acenaphthyl)-N'-(3-isopropylphenyl)-N-methylguanidine;
N-(3-acenaphthyl)-N'-(3-isopropylphenyl)-N'-methylguanidine;
N-(3-acenaphthyl)-N'-(3-isopropylphenyl)-N,N'-bis-methylguanidine;
N-(3-acenaphthyl)-N'-(3-tert-butylphenyl)guanidine;
N-(3-acenaphthyl)-N'-(3-tert-butylphenyl)-N-methylguanidine;
N-(3-acenaphthyl)-N'-(3-tert-butylphenyl)-N'-methylguanidine;
N-(3-acenaphthyl)-N'-(3-tert-butylphenyl)-N,N'-bis-methylguanidine;
N-(3-acenaphthyl)-N'-(2,3,5,6-tetrachlorophenyl)guanidine;
N-(3-acenaphthyl)-N'-(2,3,5,6-tetrachlorophenyl)-N-methylguanidine;
N-(3-acenaphthyl)-N'-(2,3,5,6-tetrachlorophenyl)-N'-methylguanidine;
N-(3-acenaphthyl)-N'-(2,3,5,6-tetrachlorophenyl)-N,N'-bis-methylguanidine;
N-(3-acenaphthyl)-N'-(3-iodophenyl)guanidine;
N-(3-acenaphthyl)-N'-(3-iodophenyl)-N-methylguanidine;
N-(3-acenaphthyl)-N'-(3-iodophenyl)-N'-methylguanidine;
N-(3-acenaphthyl)-N'-(3-iodophenyl)-N,N'-bis-methylguanidine;
N-(3-acenaphthyl)-N'-(3-nitrophenyl)guanidine;
N-(3-acenaphthyl)-N'-(3-nitrophenyl)-N-methylguanidine;
N-(3-acenaphthyl)-N'-(3-nitrophenyl)-N'-methylguanidine;
N-(3-acenaphthyl)-N'-(3-nitrophenyl)-N,N'-bis-methylguanidine;
N-(3-acenaphthyl)-N'-(5-indolinyl)guanidine;
N-(3-acenaphthyl)-N'-(5-indolinyl)-N-methylguanidine;
N-(3-acenaphthyl)-N'-(5-indolinyl)-N'-methylguanidine;
N-(3-acenaphthyl)-N'-(5-indolinyl)-N,N'-bis-methylguanidine;
N-(3-acenaphthy)-N'-(2-fluorenyl)guanidine;
N-(3-acenaphthy)-N'-(2-fluorenyl)-N-methylguanidine;
N-(3-acenaphthy)-N'-(2-fluorenyl)-N'-methylguanidine;
N-(3-acenaphthy)-N'-(2-fluorenyl)-N,N'-bis-methylguanidine;
N-(3-acenaphthyl)-N'-(4-n-butoxyphenyl)guanidine;
N-(3-acenaphthyl)-N'-(4-n-butoxyphenyl)-N-methylguanidine;
N-(3-acenaphthyl)-N'-(4-n-butoxyphenyl)-N'-methylguanidine;
N-(3-acenaphthyl)-N'-(4-n-butoxyphenyl)-N,N'-bis-methylguanidine;
N-(3-acenaphthyl)-N'-(3-(2-methoxy)dibenzofuranyl)guanidine;
N-(3-acenaphthyl)-N'-(3-(2-methoxy)dibenzofuranyl)-N-methylguanidine;
N-(3-acenaphthyl)-N'-(3-(2-methoxy)dibenzofuranyl)-N'-methylguanidine;
N-(3-acenaphthyl)-N'-(3-(2-methoxy)dibenzofuranyl)-N,N'-bis-methylguanidine;
N-(3-acenaphthyl)-N'-(9-hydroxy-2-fluorenyl)guanidine;
N-(3-acenaphthyl)-N'-(9-hydroxy-2-fluorenyl)-N-methylguanidine;
N-(3-acenaphthyl)-N'-(9-hydroxy-2-fluorenyl)-N'-methylguanidine;
N-(3-acenaphthyl)-N'-(9-hydroxy-2-fluorenyl)-N,N'-bis-methylguanidine;
N-(3-acenaphthyl)-N'-(4-trifluoromethylphenyl)guanidine;
N-(3-acenaphthyl)-N'-(4-trifluoromethylphenyl)-N-methylguanidine;
N-(3-acenaphthyl)-N'-(4-trifluoromethylphenyl)-N'-methylguanidine;
N-(3-acenaphthyl)-N'-(4-trifluoromethylphenyl)-N,N'-bis-methylguanidine; N-(3-acenaphthyl)-N'-(4-methylthiophenyl)guanidine;
N-(3-acenaphthyl)-N'-(4-methylthiophenyl)-N-methylguanidine;
N-(3-acenaphthyl)-N'-(4-methylthiophenyl)-N'-methylguanidine;
N-(3-acenaphthyl)-N'-(4-methylthiophenyl)-N,N'-bis-methylguanidine;
N-(3-acenaphthyl)-N'-(3-sec-butylphenyl)guanidine;
N-(3-acenaphthyl)-N'-(3-sec-butylphenyl)-N-methylguanidine;
N-(3-acenaphthyl)-N'-(3-sec-butylphenyl)-N'-methylguanidine;
N-(3-acenaphthyl)-N'-(3-sec-butylphenyl)-N,N'-bis-methylguanidine;
N-(5-acenaphthyl)-N'-(4-benzyloxyphenyl)guanidine;
N-(5-acenaphthyl)-N'-(3-benzyloxyphenyl)guanidine;
N-(5-acenaphthyl)-N'-(3-sec-butylphenyl)guanidine;
N-(5-acenaphthyl)-N'-(2-anthracenyl)guanidine;
N-(5-acenaphthyl)-N'-(3-phenethylphenyl)guanidine;
N-(5-acenaphthyl)-N'-(4-adamantylphenyl)guanidine;
N-(5-acenaphthyl)-N'-(3-benzyloxyphenyl)-N'-methylguanidine;
N-(5-acenaphthyl)-N'-(4-benzyloxyphenyl)-N'-methylguanidine;
N-(5-acenaphthyl)-N'-(3-biphenyl)-N'-methylguanidine;

N-(5-acenaphthyl)-N'-(3-(1'-methyl-2'-phenylethyl)phenyl)
  guanidine;
N-(5-acenaphthyl)-N'-(3,4-tetralinylphenyl)guanidine;
N-(5-acenaphthyl)-N'-(7-benzyltetralinylphenyl)guanidine;
N-(5-acenaphthyl)-N'-(3,4-dibenzyl oxyphenyl)guanidine;
N-(5-acenaphthyl)-N'-(3-1-(4-ethoxy)phenyl)propanyl)
  phenyl)guanidine;
N-(5-acenaphthyl)-N'-(3-(N",N"-dibenzyl)aminophenyl)
  guanidine;
N-(5-acenaphthyl)-N'-(3-(1'-benzylbutyl)phenyl)guanidine;
N-(5-acenaphthyl)-N'-3-(4-tert-butylbenzoxymethyl)
  phenylguanidine;
N-(5-acenaphthyl)-N'-(2-(2-indolyl)phenyl)guanidine;
N-(5-acenaphthyl-N'-(3-bromophenyl)guanidine;
N-(5-acenaphyl)-N'-(2,3,4-trichlorophenyl)-N,N'-
  dimethylguanidine;
N-(5-acenaphthyl)-N'-(2,3,4-trichloro-phenyl)-N'-
  methylguanidine;
N-(5-acenaphthyl)-N'-(4-(2'-benzothiazole-6'-methyl)
  phenyl)guanidine;
N-(3-acenaphthyl)-N'-(4-benzoyloxyphenyl)guanidine;
N-(3-acenaphthyl)-N'-(3-benzoyloxyphenyl)guanidine;
N-(3-acenaphthyl)-N'-(3-sec-butylphenyl)guanidine;
N-(3-acenaphthyl)-N'-(2-anthracenyl)guanidine;
N-(3-acenaphthyl)-N'-(3-phenethylphenyl)guanidine;
N-(3-acenaphthyl)-N'-(4-adamantylphenyl)guanidine;
N-(3-acenaphthyl)-N'-(3-benzyloxyphenyl)-N'-
  methylguanidine;
N-(3-acenaphthyl)-N'-(4-benzyloxyphenyl)-N'-
  methylguanidine;
N-(3-acenaphthyl)-N'-(3-biphenyl)-N'-methylguanidine;
N-(3-acenaphthyl)-N'-(3-(1'-methyl-2'-phenylethyl)phenyl)
  guanidine;
N-(3-acenaphthyl)-N'-(3,4-tetralinylphenyl)guanidine;
N-(3-acenaphthyl)-N'-(7-benzyltetralinylphenyl)guanidine;
N-(3-acenaphthyl)-N'-(3–1-(4-ethoxy)phenyl)propanyl)
  phenyl)guanidine;
N-(3-acenaphthyl)-N'-(3-(N",N"-dibenzyl)aminophenyl)
  guanidine;
N-(3-acenaphthyl)-N'-(3-(1'-benzylbutyl)phenyl)guanidine;
N-(3-acenaphthyl)-N'-3-(4-tert-butylbenzoxymethyl)
  phenylguanidine;
N-(3-acenaphthyl)-N'-(2-(2-indolyl)phenyl)guanidine;
N-(3-acenaphthyl-N'-(3-bromophenyl)guanidine;
N-(3-acenaphthyl)-N'-(3,4-dibenzyl oxyphenyl)guanidine;
N-(3-acenapthyl)-N'-(2,3,4-trichlorophenyl)-N,N'-dimethyl
  guanidine;
N-(3-acenaphthyl)-N'-(2,3,4-trichlorophenyl)-N'-
  methylguanidine;
N-(3-acenaphthyl)-N-(4-(2'-benzothiazole-6'-
  methylphenyl)guanidine; and pharmaceutically accept-
  able salts of said compounds.

Additional preferred compounds include those named above with one or more ring substituents on the acenaphthyl group thereof, particularly those $R^2$ groups defined above for Formulas IIA and IIB.

Specifically preferred pharmaceutically acceptable salts of said compounds include those compounds identified in the examples which follow, and 3-acenaphthyl derivatives of those exemplified compounds, i.e. compounds that contain 3-acenaphthyl group(s) in place of 5-acenaphthyl group(s).

Compounds of the invention can be prepared by reaction of an amine, typically an amine salt such as an amine hydrochloride, with a preformed substituted cyanamide. See S. R. Safer, et al., *J. Org. Chem.*, 13:924 (1948); G. J. Durant, et al., *J. Med. Chem.*, 28:1414 (1985); C. A. Maryanoff, et al., *J. Org. Chem.*, 51:1882 (1986); M. P. Kavanaugh, et al., *Proc. Natl. Acad. Sci. USA*, 85:2844–2848 (1988); E. Weber, et al., *Proc. Natl. Acad. Sci. USA*, 83:8784–8788 (1986); H. W. J. Cressman, Org. Syn. Coll., 3:608–609 (1955); International Applications WO 91/12797 and PCT/US92/01050.

More particularly, the synthesis of the diary substituted guanidines of the invention is typically achieved by condensing a salt of an arylamine with a substituted aryl cyanamide such as 3-acenaphthyl or 5-acenaphthyl cyanamide in a suitable solvent, e.g. refluxing chlorobenzene or toluene, as shown in the Scheme-1 where Ar is as defined above. The cyanamide can be suitably prepared by reduction of the corresponding nitro-substituted aryl to an amine, followed by treatment with cyanogen bromide as shown in the following Scheme.

SCHEME-1:
PREPARATION OF N,N'-DI-ARYLGUANIDINES

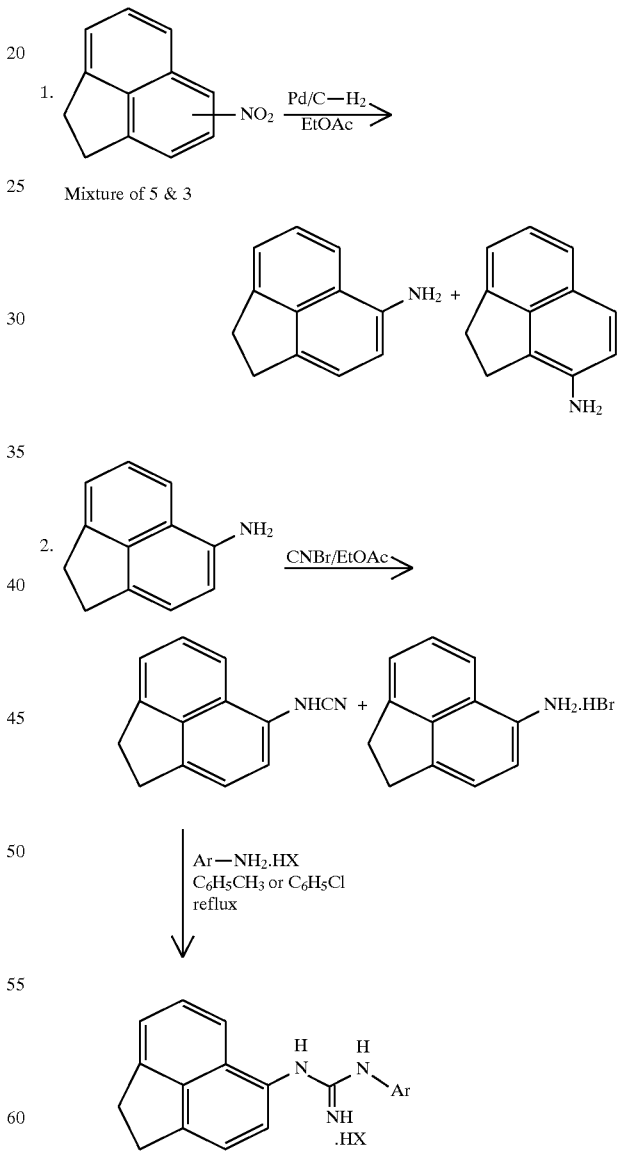

In step 1 of the above Scheme, a mixture of 5- and 3-nitro-acenaphthene is reduced with Pd/C in suitable solvent such as ethyl acetate under $H_2$ and suitable pressure such as 40 psi and the resulting amines are separated such as by recrystallization. In step 2, the desired amino acenaphthene is treated with cyanogen bromide in suitable solvent such as ethyl acetate to give N-acenaphthyl cyanamide and acenaphthyl amine hydrobromide salt. This cyanamide is subsequently reacted with substituted arylamine salts in a suitable solvent with heat such as refluxing chlorobenzene or toluene to give the final product.

SCHEME-1:
PREPARATION OF N-ALKYL AND N,N'-DIALKYL N,N'-DI-ARYL GUANIDINES

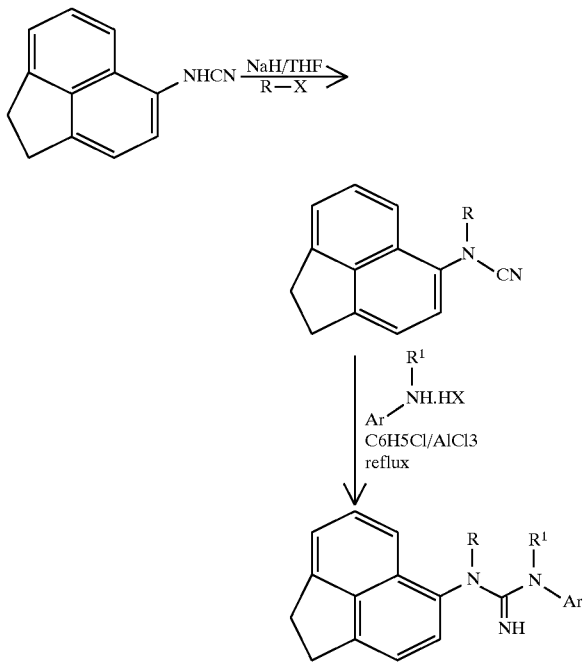

Tri and tetra-substituted guanidines of the invention may be prepared as outlined in Scheme-2 above. As shown in the Scheme, an arylcyanamide such as N-5-acenaphthyl-N-alkyl cyanamide or N-3-acenaphthyl-N-alkyl cyanamide (suitably prepared as discussed above) is treated with a salt of an aryl amine (for synthesis of tri-substituted guanidine) or salt of N-alkyl aryl amine (for synthesis of tetra-substituted guanidine) in a suitable solvent such as chlorobenzene in the presence of AlCl$_3$ catalyst. The products can be purified by conventional means such as silica gel chromatography.

While in the above Schemes reaction of an unsubstituted acenaphthyl cyanamide is depicted, an acenapthyl cyanamide having one or more ring substituents can be reacted with a salt of an aryl amine by the same procedures of Schemes-1 and 2 as described above to provide compounds of the invention having a substituted acenaphthyl moiety, including compounds of Formula IIA or IIB.

Such substituted cyanamide reagents can be readily prepared. For example, a substituted acenaphthyl derivative can be nitrated (e.g., treatment with HNO$_3$/H2SO$_4$) to provide a 3-nitroacephthyl or 5-nitroacephthyl having one or more additional ring substituents. See the procedure of M. D. Vareny, et al., *J. Med. Chem.*, 35: 671 (1992). The reaction products can be separated by recrystallization or chromatography if more than one isomer is generated from the nitration. Such a substituted nitro derivative can then be reduced to the amine by hydrogenation, the amine then reacted with cyanogen bromide and then an arylamine salt as described above to provide a compound of Formula IIA or IIB. Suitable substituted acenaphthyl derivatives that can be nitrated and further reacted in such manner include, e.g., haloacenaphthalene such as 3-fluoroacenaphthalene, 3-chloroacenaphthalene, 3-bromoacenaphthalene, 4-fluoroacenaphthalene, 4-chloroacenaphthalene, 4-bromoacenaphthalene, 4-fluoroacenaphthalene, 4-chloroacenaphthalene, and 4-bromoacenaphthalene; alkanoylacenaphthalene such as 4-acetylacenaphthalene; alkoxynaphthalene such as 4-methoxyacenaphthalene; acenaphthalene, 3-acid; 5-acenaphthalene, ethanol; 5-acenaphthalene, methanol; alkenylacenaphthalene such as 3-(1-methylpropenyl)acenaphthalene; 5-acenaphthalenecarboxanilide; and the like.

If the ring substitutent of the acenaphthyl derivative includes a potentially reactive functionality (e.g. an unsaturated carbon-carbon bond that could be reduced during hydrogenation of the nitro group), a suitable protecting group can be employed that is later removed as will be known to those skilled in the synthesis art.

In addition to nitration of a substituted acephthyl derivative, compounds of the invention having a substituted acenaphthyl moiety, including compounds of Formulas IIA or IIB, can be prepared by a number of other routes. Specifically, for preparation of other acenaphthyl derivatives having an amine or amine-precursor group and one or more additional ring substituents, see V. N. Komissarov, *Zh. Org. Khim.*, 26(5): 1106–10 (1990); L. Skulski, et al., *Pol. J. Chem.*, 55(9): 1809–24 (1981); A. F. Pozharskii, *Isobret. Prom. Obraztsy, Tovarnye Znaki*, (3), 96–7 (1982); J. P. Li, et al., US 78–10 890736 (1978); N. S. Vorozhtsov, *Zh. Org. Khim.*, 8(2): 353–7 (1972); J. Wolinski et al., *Rocz. Chem.*, 44(9): 1721–31 (1970); A. P. Karishin, et al., *Zh. Obshch. Khim.*, 39(9): 2098–101 (1969); and V. V. Mezheritskii, et al., *Zh. Org. Khim.*, 27(10), 2198–204 (1991). Compounds prepared by such methods can be converted to an amine, if necessary, and then reacted with CNBr and an aryl amine as described above to provide guanidine derivatives having a substituted acenaphthyl moiety.

As discussed above, the N,N'-diaryl substituted guanidines of the invention are useful for a number of therapeutic applications, including treatment of those diseases that result from modulation of a particular neurotransmitter system that can be counteracted by one or more of the substituted guanidines of the invention. As mentioned above, modulation of neurotransmitter release involves either the inhibition of neurotransmitter release, the potentiation of neurotransmitter release, or the increase or decrease of the time course of action of neurotransmitter release from neuronal tissue. Neurotransmitters which may be modulated by compounds of the invention include, but are not limited to, glutamate, dopamine, norepinephrine, glycine, aspartate and serotonin. One of ordinary skilled in the art can select those compounds which are effective or particularly effective modulators of neurotransmitter release using the procedures disclosed herein or in PCT/US92/01050 with no more than routine experimentation. For example, compounds for the prevention of neuronal death can be evaluated in vivo in one or more variations of the rat middle cerebral artery occlusion model. Such models are generally considered to be particularly predictive of neuroprotective efficacy in stroke. See Ginsburg, et al., *Stroke*, 20:1627–1642 (1989). Efficacy of lead compounds also may be assessed in the 4-vessel occlusion model of global ischemia. See Pulsinelli, et al., *Stroke*: 19:913–941 (1988) and PCT/US92/01050.

In particular, the invention provides methods for treatment and/or prophylaxis of neurological conditions such as epilepsy, neurodegenerative conditions and/or nerve cell death resulting from e.g. hypoxia, hypoglycemia, brain or spinal chord ischemia, brain or spinal chord trauma, stroke, heart attack, drowning or carbon monoxide poisoning. Typical candidates for treatment include heart attack, stroke, brain or spinal cord injury patients, patients undergoing major surgery where brain ischemia is a potential complication and patients such as divers suffering from decompression sickness due to gas emboli in the blood stream.

The invention also provides methods to treat and/or prevent various neurodegenerative diseases of a subject such as an animal, particularly a human, by administering a therapeutically effective amount of one or more compounds of the invention. Typical neurodegenerative diseases that can be treated and/or prevented include Parkinson's disease, Huntington's disease, Amyotrophic Lateral Sclerosis, Alzheimer's disease, Down's Syndrome, Korsakoff's disease, olivopontocerebellar atrophy, HIV-induced dementia and blindness or multi-infarct dementia. As disclosed by Dreyer et al., Science, 248:364–367 (1990), gp120 neurotoxicity is associated with increased levels of $Ca^{2+}$ which are apparently mediated by excitatory amino acids binding at the NMDA receptor site. Though again not wishing to be bound by theory, compounds of the invention should have utility in treating HIV-induced dementia and blindness by means of preventing the release of excessive glutamate.

As noted above the invention provides methods of treating Korsakoff's disease, a chronic alcoholism-induced condition, comprising administering to a subject including a mammal, particularly a human, one or more compounds of the invention in an amount effective to treat the disease. Pretreatment of animals with the NMDA antagonist MK-801 (Merck Index, monograph 3392, 11th ed., 1989) markedly attenuates the extent of cell loss, hemorrhages and amino acid changes in a rat model of Korsakoff's disease. See P. J. Langlais, et al., *Soc. Neurosci. Abstr.*, 14:774 (1988). Therefore, compounds of the invention have utility for the attenuation of cell loss, hemorrhages and amino acid changes associated with Korsakoff's disease.

At least some compounds of the invention will have utility in treating or preventing conditions treatable by the blockage of voltage-activated sodium channels as demonstrated by the results disclosed in Example 66 which follows. Accordingly, the invention provides methods for blockage of voltage sensitive sodium channels of neuronal cells, particularly mammalian cells such as human neuronal cells, comprising the administration to the cells of an effective amount of a compound of the invention, particularly by such administration to a mammal in need of such treatment. Conditions that can be treated by blockage of sodium channels will include, e.g., epilepsy. Moreover, some compounds of the invention will block sodium channels in addition to presynaptic calcium channels. This dual action potentially may be particularly desirable for neuroprotective therapies.

It has been reported that NMDA antagonists which do not cross the blood/brain barrier may be used to alleviate certain undesirable side effects of cancer chemotherapy, e.g. nausea and emesis (A. Fink-Jensen et al., *Neurosci. Lett.*, 137(2) :173 (1992)).

See also Price, M. T., et al., *Soc. Neurosci. Abstr.*, 16:377, abstr. 161.16 (1990). Compounds of the invention, particularly those compounds that are charged such as in the form of a pharmaceutically acceptable salt, and those compounds that otherwise are hydrophilic such as compounds that comprise one or more polar functionalities e.g. carboxy, amino, hydroxy and the like, may have comparatively limited ability to cross the blood brain barrier. It is thus believed that compounds of the invention, especially charged or otherwise hydrophilic compounds of the invention with limited blood brain barrier permeability, will be clinically useful to ameliorate the side effects associated with chemotherapy, particularly cancer thermotherapy, that may be experienced by a mammal, particularly a human receiving such chemotherapy. The compound of the invention would be typically administered to the subject in coordination with the chemotherapy regime.

Compounds of the invention may be used in therapy in conjunction with other medicaments. For example, for treatment of a stroke victim, one or more compounds of the invention may be suitably administered together with a pharmaceutical targeted for interaction in the blood clotting mechanism such as streptokinase, TPA and urokinase.

The compounds of this invention can be administered intranasally, orally or by injection, e.g., intramuscular, intraperitoneal, subcutaneous or intravenous injection, or by transdermal, intraocular or enteral means. The optimal dose can be determined by conventional means including the assays of Examples 64–65 which follow. Guanidines of the present invention are suitably administered to a subject in the protonated and water-soluble form, e.g., as a pharmaceutically acceptable salt of an organic or inorganic acid, e.g., hydrochloride, hydrobromide, sulfate, hemi-sulfate, mesylate, gluconate, phosphate, nitrate, acetate, oxalate, citrate, maleate, etc., prepared by procedures such as those disclosed in the examples which follow.

The compounds of this invention can be employed, either alone or in combination with one or more other therapeutic agents as discussed above, as a pharmaceutical composition in mixture with conventional excipient, i.e., pharmaceutically acceptable organic or inorganic carrier substances suitable for parenteral, enteral or intranasal application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampoules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Intravenous or parenteral administration, e.g., subcutaneous, intraperitoneal or intramuscular administration are generally preferred.

It will be appreciated that the actual preferred amounts of active compounds used in a given therapy will vary according to the specific compound being utilized, the particular compositions formulated, the mode of application, the particular site of administration, the subject's weight, age and general health, etc. Optimal administration rates for a given protocol of administration can be readily ascertained by those skilled in the art using conventional dosage determination tests conducted with regard to the foregoing guidelines. In general, a suitable effective dose of one or more compounds of Formula I, Formula IA, Formula IB, Formula IIA or Formula IIB, particularly when using the more potent compound(s) of Formula I, Formula IA, Formula IB, Formula IIA or Formula IIB will be in the range of from 0.5 to 50 milligrams per kilogram bodyweight of recipient per day, preferably in the range of 1 to 10 milligrams per kilogram bodyweight of recipient per day. The desired dose is suitably administered once daily, or several sub-doses, e.g., 2 to 4 sub-doses, are administered at appropriate intervals through the day, or other appropriate schedule. Such sub-doses may be administered as unit dosage forms, e.g., containing from 0.25 to 25 milligrams of compound(s) of Formula I, Formula IA, Formula IB, Formula IIA or Formula IIB per unit dosage, preferably from 0.5 to 5 milligrams per unit dosage.

As with prior guanidines such as those reported in U.S. Pat. No. 1,411,713, the guanidines of the present invention should have utility as rubber accelerators.

All documents mentioned herein are incorporated herein by reference in their entirety.

The present invention will be further illustrated with reference to the following examples which aid in the understanding of the present invention, but which are not to be construed as limitations thereof.

GENERAL COMMENTS

In the following examples, all percentages reported herein, unless otherwise specified, are percent by weight. All temperatures are expressed in degrees Celsius.

Melting points were determined in open capillary tubes on a Thomas-Hoover apparatus and are uncorrected. Thin-layer chromatography was performed on Merck silica gel 60 $F_{254}$ (0.2 mm) or Baker-flex 1B2-F silica gel plates. Guanidines were visualized on TLC with 254-nM UV light or as a blue spot with bromcresol spray reagent (Sigma Chemical Co.). Preparative TLC was performed on Analtech GF precoated silica gel (1000 $\mu$m) glass-backed plates (20×20 cm). The IR, $^1$H and $^{13}$C NMR spectra of all compounds were consistent with their assigned structures. NMR spectra were recorded on a General Electric QE-300 or Varian Gemini 300 and the chemical shifts were reported in ppm ($\delta$) relative to the residual signal of the deuterated solvent (CHCl$_3$ $\delta$ 7.26; CHD$_2$OD, $\delta$ 3.30). Infrared spectra were recorded in CHCl$_3$ (unless otherwise noted) on a Nicolet 5DXB FT-IR or Perkin-Elmer model 1420. All new compounds were analyzed either for C, H, and N elemental analyses or for exact mass. Compounds analyzed for exact mass were further analyzed by HPLC and/or 300 MHz NMR spectrometer ($^1$H) for their purity. Elemental analyses were performed by Desert Analytics (Tucson, Ariz.) or Galbraith Laboratories (Knoxville, Tenn.). High Resolution Mass spectra (HRMS) were recorded on a Finnegan MAT 90. HPLC were performed on a C18 reverse phase column using 50:50 water:acetonitrile with 0.1% TFA as the mobile phase. BrCN was obtained from Aldrich Chemical Co., and was used as received. All starting amines were obtained from commercial sources and were purified by standard procedures before use, or they were prepared, where noted, by published procedures. Chlorobenzene was freshly distilled from CaH$_2$ or anhydrous quality solvent (Sure Seal) supplied by Aldrich wa used. Ether (Et$_2$O) and tetrahydrofuran (THF) were refluxed over sodium/benzophenone ketyl and freshly distilled under N$_2$ before their use or anhydrous quality solvents (Sure Seal) supplied by Aldrich were used. All other solvents were reagent grade. Alkyl- and arylcyanamides were prepared as described above and according to published procedures (e.g., PCT/US92/01050) by reaction of the amines with BrCN in ether.

EXAMPLE 1

Preparation of N-(5-acenaphthyl)-N'-(2,3,4-trichlorophenyl)guanidine•HCl (METHOD-A (Scheme-1))

Step 1. 5-Acenarhthyl cyanamide

5-Aminoacenaphthene (7.0 g, 41.4 mmol) was dissolved in a mixture of ether (100 Ml) and ethyl acetate (25 Ml). To this solution was added 5.2 mL of a 5M solution of cyanogen bromide in M acetonitrile (25.6 mmol of cyanogen bromide). The solution was stirred overnight, with the gradual appearance of gray precipitate. The solid was removed by filtration (the hydrobromide of 5-aminoacenaphthene) and the resulting filtrate concentrated in vacuo to afford a semi-solid residue. Ether (60 mL) was added to the residue and the mixture was stirred overnight. The solid was removed (more hydrobromide of 5-aminoacenaphthene) and the filtrate concentrated to approximately 20 mL and then diluted with warm cyclohexane (15 mL). Upon standing at room temperature, off white crystals were deposited. They were collected, washed with cyclohexane-ether (1:1) and dried in vacuo to give 1.5 g of pure product, mp 163°–65° C.

Step 2. Preparation of N-(5-acenaohthyl)-N'-(2,3,4-trichlorophenvl)guanidine•HCl A mixture of 5-acenaphthyl cyanamide (0.194 g, 1 mmol) and 2,3,4-trichloroaniline hydrochloride (0.221 g, 0.95 mmol; prepared from 2,3,4-trichloroaniline and 1. ON HCl-ether) were heated at reflux in 5 mL of chlorobenzene. Shortly after reflux temperature was reached all the solids had dissolved to give a clear solution. After a total of 2 hour reflux, the mixture was cooled to 20° C. and allowed to stand for 24 hours. The solid was collected by filtration and washed with excess of methylene chloride and dried in vacuo at 40° C. to give product (0.293 g, 68%) as an off white solid, mp: 208°–10° C.; $^1$H NMR (CD$_3$OD): $\delta$ 7.70–7.58 (m, 3H, Ar—H), 7.48 (d, 2H, J=7.5Hz, Ar—H), 3.47–3.41 (m, 4H, 2×CH$_2$); HRMS 389.0220 (389.0253 calcd. for C$_{19}$H$_{14}$N$_3$Cl$_3$); Anal Calcd. for C$_{19}$H$_{15}$N$_3$Cl$_4$ (427.15): C, 53.42; H, 3.54; N, 9.84; Cl, 33.2; Found: C, 53.25: H, 3.57; N, 9.67; Cl, 33.75.

EXAMPLE 2

Preparation of N,N'-bis(5-acenaphthyl)-N-methyl guanidine•HCl (METHOD B (Scheme-2))

Part 1. Preoaration of N-methvl-N-5-acenaphthyl cyanamide

A solution of 5-acenaphthyl cyanamide (1.5 g, 7.73 mmol) in THF (22 mL) was slowly added to a stirred suspension of sodium hydride (0.6 g, 15.1 mmol) in THF (8 mL) at room temperature. After 3 hour reflux, the reaction mixture was cooled to 20° C., methyl iodide (2.64 g, 18.6 mmol) wa added and stirred the contents at 20° C. After 16 hours, the reaction was quenched by careful addition of methanol (15 mL) followed by water (35 mL). Extracted by methylene chloride (3×30 mL), dried over MgSO$_4$ and the solvent was evaporated. The residue was purified on flash chromatography to yield the product (0.8 g, 50%) as a tan solid. TLC (CHCl$_3$:CH$_3$OH; 10:1): R$_f$=0.72.

Part 2. Preparation of N,N'-bis(5-acenaphthyl)-N-methyl guanidine•HCl

Aluminum chloride (0.28 g, 2.11 mmol) was added to a stirred solution of N-5-acenaphthyl-N-methyl cyanamide (0.4 g, 1.92 mmol) in chlorobenzene (5.8 mL) at 145° C. After 10 minutes 5-acenaphthene amine hydrochloride (0.39 g, 1.29 mmol, prepared from 5-acenaphthene and 1.0M HCl-ether) was added and continued reflux. After 20 hours, the reaction mixture was evaporated and the product was purified by flash chromatography to afford the title compound (0.41 g, 55%) as orange tint white solid; mp: 236° C.; TLC (CH$_2$Cl$_2$:CH$_3$OH; 9:1); R$_f$=0.19; $^1$H NMR (CDCl$_3$+ CD$_3$OD): δ 7.61–7.04 (m, 10H, Ar—H), 3.84–3.81 (m, 2H, CH$_2$), 3.43–3.27 (m, 9H, 3×CH$_2$ and CH$_3$); HRMS: 377.1897 (377.1892 calcd. for C$_{26}$H$_{23}$N$_3$).

EXAMPLE 3

Preparation of N,N'-bis(5-acenaphthyl)-N,N'-bis-methyl guanidine•HCl (METHOD C (Scheme-2))

Part 1. Preparation of N-methyl-N-5-acenaphthyl cyanamide

Prepared as per part 1 in Method B of Example 2.

Part 2. Preraration of N-methyl-N-5-acenaphthyl amine

5-Acenaphthene amine (5.8 g, 34.3 mmol) was dissolved in warm formic acid (97%, 25 mL) and refluxed. After 7 hours, the reaction mixture was cooled to 25° C. and then let is stand in refrigerator for 12 hours. The solid was filtered and washed with acetonitrile and then air-dried to afford the formamide (6.65 g), which was used in the next step without further purification.

BH$_3$-THF solution (50 mL) was added dropwise to a stirred suspension of above formamide (6.07 g, 30.4 mmol) in THF (100 mL) at ice-bath temperature. After stirring the contents at 25° C. for 18 hours, the reaction mixture was concentrated to a volume of ca. 35 mL and the ethyl acetate (10 mL) was added at 10° C. The mixture was quenched with 3N HCl solution and then basified with NaOH solution. It was extracted with methylene chloride (2×75 mL), dried (Na$_2$SO$_4$) and evaporated to give a tan colored solid (5.45 g). It was recrystallized from methanol to afford the title compound (2.85 g) as tan colored crystals; mp 102°–03° C.

Part 3. Preparation of N,N'-bis(5-acenaphthyl)-N,N'-bis-methyl guanidine•HCl

Aluminum chloride (0.21 g, 1.58 mmol) was added to a stirred solution of N-5-acenaphthyl-N-methyl cyanamide (0.3 g, 1.44 mmol) in chlorobenzene (7 mL) at 145° C. After 10 minutes 5-acenaphthene-N-methyl amine hydrochloride (0.29 g, 1.3 mmol; prepared from 5-acenaphthene-N-methyl amine and 1.0M HCl-ether) was added and continued reflux. After 4 hours, the reaction mixture was evaporated on rotavap and the product was purified by flash chromatography to afford the title compound (0.25 g, 45%) as yellow solid; mp: 272° C.; TLC (CHCl$_3$:CH$_3$OH; 10:1): R$_f$=0.17; $^1$H NMR (CD$_3$OD): δ 7.18 (bs, 5H, Ar—H), 6.78–6.73 (m, 5H, Ar—H), 3.47 (s, 6H, 2×CH$_3$), 3.24–3.19 (m, 4H, 2×CH$_2$), 3.04 (bs, 4H, 2×CH$_2$); HRMS: 391.2051 (391.2048 calcd. for C$_{27}$H$_{25}$N$_3$).

EXAMPLES 4–63

By methods indicated above, including by the specified Methods A–C of Examples 1–3 respectively and using appropriately substituted reagents, the following named compounds were prepared having the indicated physical characteristics.

EXAMPLE 4

N-(5-acenaphthyl)-N'-(1-anthracenyl)guanidine•mesylate

Preparation: As per Method A of Example 1. White solid; mp: 243°–45° C.; $^1$H NMR (CD$_3$OD): δ 8.65–7.25 (m, 14H, Ar—H), 3.33–3.20 (m, 4H, 2×CH$_2$), 2.25 (s, 3H, —CH$_3$); Anal. Calcd. for C$_{28}$H$_{25}$N$_3$·CH$_3$SO$_3$H: C, 69.54; H, 5.21; N, 8.69; Found: C, 69.33; H, 5.23; N, 8.55.

EXAMPLE 5

N-(5-acenaphthyl)-N'-(4-tertbutylphenyl)guanidine•HCl

Preparation: As per Method A of Example 1. White solid; TLC (CH$_2$Cl$_2$:CH$_3$OH; 9:1): R$_f$=0.5; $^1$H NMR (CD$_3$OD): δ 7.65–7.20 (m, 9H, Ar—H), 3.30 (m, 4H 2×CH$_2$), 1.22 (s, 9H, 3×CH$_3$); HRMS: 343.2043 (343.2048 calcd. for C$_{23}$H$_{25}$N$_3$).

EXAMPLE 6

N-(5-acenaphthyl)-N'-(4-cyclohexylphenyl)guanidine•HCl

Preparation: As per Method A of Example 1, except that 4-cyclohexylphenyl cyanamide was reacted with 5-acenaphthyl-1-amine hydrochloride. White solid; mp: 232°–34° C.; $^1$H NMR (DMSO): δ 7.8–8.2 (m, 13H, Ar—H), 3.4–3.3 (m, 5H, 2×CH$_2$ and CH), 1.8–1.15 (m, 10H, 5×CH$_2$); Anal. Calcd. for C$_{25}$H$_{28}$ClN$_3$ (405.95): C, 73.96; H, 6.95; N, 10.35; Cl, 8.73; Found: C, 73.91; H, 6.96; N, 10.12; Cl, 8.56.

EXAMPLE 7

N-(5-acenaphthyl)-N'-(4-secbutylphenyl)guanidine•HCl

Preparation: As per Method A of Example 1. White solid; TLC (CH$_2$Cl$_2$:CH$_3$OH; 9:1): R$_f$=0.7; $^1$H NMR (CD$_3$OD): δ 7.60–7.15 (m, 9H, Ar—H), 3.30 (m, 4H, 2×CH$_2$), 2.52 (q, 1H, —CH), 1.50 (m, 2H, CH$_2$), 1.11 (d, 3H, CH$_3$), 0.71 (t, 3H, CH$_3$); HRMS: 343.2051 (343.2049 calcd. for C$_{23}$H$_{25}$N$_3$).

EXAMPLE 8

N-(5-acenaphthyl)-N'-(4-methoxyphenyl)guanidine•HBr

Preparation: As per Method A of Example 1. Fluffy cream solid; mp: 187°–200° C.; TLC (CHCl$_3$:CH$_3$OH; 10:1); R$_f$=0.31; $^1$H NMR (CDCl$_3$): δ 7.45–7.10 (m, 7H, Ar—H), 6.80 (d, 2H, J=8 Hz, Ar—H), 3.68 (s, 3H, OCH$_3$), 3.38–3.22 (m, 4H, 2×CH$_2$); HRMS: 317.1509 (317.1528 calcd. for C$_{20}$H$_{19}$N$_3$O); Anal. Calcd. for C$_{20}$H$_{20}$N$_3$BrO (398.30): C, 60.44; H, 5.08; N, 10.58; Found: C, 60.28; H, 5.14; N, 10.41.

EXAMPLE 9

N-(5-acenaphthyl)-N'(2,3-dichlorophenyl)guanidine•HCl

Preparation: As per Method A of Example 1. White (yellow tint) solid; mp: 124°–30° C.; TLC (CHCl$_3$:CH$_3$OH; 10:1): R$_f$=0.18; $^1$H NMR (CDCl$_3$): δ 7.59 (d, 1H, J=8 Hz, Ar—H), 7.47 (t, 1H, J=8 Hz, Ar—H), 7.36–7.14 (m, 6H, Ar—H), 3.40–3.25 (m, 4H, 2×CH$_2$); HRMS: 355.0647 (355.0643 calcd. for C$_{19}$H$_{15}$C$_{12}$N$_3$).

EXAMPLE 10

N-(5-acenaphthyl)-N'-(4-methoxy-2-naphthyl)guanidine

Preparation: As per Method A of Example 1. Light yellow solid; mp: 191°–92° C.; TLC (CH$_2$Cl$_2$:CH$_3$OH; 9:1): R$_f$=0.51; $^1$H NMR (CD$_3$OD+CDCl$_3$): δ 8.17 (d, 1H, J=8 Hz, Ar—H), 7.73 (d, 1H, J=8 Hz, Ar—H), 7.66 (d, 1H, J=8 Hz, Ar—H), 7.57–7.26 (m, 7H, Ar—H), 7.09 (d, 1H, J=8Hz, Ar—H), 3.96 (s, 3H, OCH$_3$), 3.43–3.35 (m, 4H, 2×CH$_2$); HRMS: 367.1680 (367.1685 calcd. for C$_{24}$H$_{21}$ON$_3$).

EXAMPLE 11
N-(5-acenaphthyl)-N'-(3,4-dichlorophenyl)guanidine•HCl

Preparation: As per Method A of Example 1. White solid; mp: >300° C.; TLC (CHCl$_3$:CH$_3$OH; 10:1): R$_f$=0.27; $^1$H NMR (CDCl$_3$): δ 7.55 (d, 1H, J=8 Hz Ar—H), 7.48 (t, 1H, J=8 Hz, Ar—H), 7.37 (d, 2H, J=8 Hz, Ar—H), 7.30 (t, 2H, J=8 Hz, Ar—H), 7.19 (d, 1H, J=7 Hz, Ar—H), 7.13 (bd, 1H, Ar—H), 3.66–3.30 (m, 4H, 2×CH$_2$); HRMS: 355.0651 (355.0643 calcd. for C$_{19}$H$_{15}$Cl$_2$N$_3$).

EXAMPLE 12
N-(5-acenaphthyl)-N'-(4-chlorophenyl)guanidine•HBr

Preparation: As per Method A of Example 1, except N-4-chlorophenyl cyanamide was reacted with 5-acenaphthyl-1-amine hydrobromide. White solid; mp: 216°–17° C.; $^1$H NMR (CDCl$_3$): 67.65–7.23 (m, 9H, Ar—H), 3.42–3.35 (m, 4H, 2×CH$_2$); $^{13}$C NMR (CDCl$_3$): 147.81, 146.47, 140.09, 133.35, 132.11, 131.98, 129.90, 129.40, 127.48, 126.83, 126.70, 126.66 124.65, 124.51, 120.52, 118.95, 30.49, 29.94; HRMS: 321.1039 (321.1033 calcd. for C$_{19}$H$_{16}$N$_3$Cl).

EXAMPLE 13
N-(5-acenaphthyl)-N'-(2-naphthyl)guanidine•HCl

Preparation: As per Method A of Example 1. Light yellow solid; mp: 200° C.; TLC (CHCl$_3$:CH$_3$OH; 10:1): R$_f$=0.14; $^1$H NMR (CDCl$_3$+CD$_3$OD): δ 7.78–7.14 (m, 12H, Ar—H), 3.33–3.25 (m, 4H, 2×CH$_2$); HRMS: 337.1500 (337.1579 calcd. for C$_{23}$H$_{19}$N$_3$).

EXAMPLE 14
N-(5-acenaphthyl)-N'(6-quinolinyl)guanidine•HCl

Preparation: As per Method A of Example 1. White solid; mp: 242°–44° C.; TLC (CHCl$_3$:MeOH 10:1): R$_f$=0.2; $^1$H NMR (DMSO): δ 9.1–7.3 (m, 11H, Ar—H), 3.5–3.2 (m, 4H, 2×CH$_2$).

EXAMPLE 15
N-(5-acenaphthyl)-N'-(4-nitrophenyl)guanidine•HCl

Preparation: As per Method A of Example 1. Off white solid; mp: 85°–86° C.; $^1$H NMR (CD$_3$OD): δ 7.57–7.05 (m, 9H, Ar—H), 3.49–3.43 (m, 4H, 2×CH$_2$); MS(Cl): m/e 333 (M+1 for the free base).

EXAMPLE 16
N-(5-acenaphthyl-N'-(3-bi-phenyl)guanidine•HCl

Preparation: As per Method A of Example 1. White cream solid; mp: 128°–36° C.; TLC (CHCl$_3$:CH$_3$OH; 10:1): R$_f$=0.56; $^1$H NMR (CD$_3$OD): δ 7.68–7.35 (m, 14H, Ar—H), 3.45–3.31 (m, 4H, 2×CH$_2$); HRMS: 363.1726 (363.1735 calcd. for C$_{25}$H$_{21}$N$_3$).

EXAMPLE 17
N-(5-acenaphthyl)-N'-(2,3-dimethylphenyl)guanidine•HCl

Preparation: As per Method A of Example 1. Light yellow solid; mp: 199°–207° C.; TLC (CHCl$_3$:CH$_3$OH; 10:1): R$_f$=0.38; $^1$H NMR (CD$_3$OD): δ 7.68–7.58 (m, 2H, Ar—H), 7.48 (d, 1H, J=8 Hz, Ar—H), 7.41–7.36 (m, 2H, Ar—H), 7.23–7.16 (m, 3H, Ar—H), 3.45–3.39 (m, 4H, 2×CH$_2$), 2.34 (s, 3H, CH$_3$), 2.28 (s, 3H, CH$_3$); HRMS: 315.1717 (315.1735 calcd. for C$_{21}$H$_{21}$N$_3$).

EXAMPLE 18
N-(5-acenaphthyl)-N'-(2-bi-phenyl)guanidine•HBr

Preparation: As per Method A of Example 1. White solid; mp: 141°–43° C.; $^1$H NMR (CD$_3$OD): δ 7.56–7.05 (m, 14H, Ar—H), 3.43–3.31 (m, 4H, 2×CH$_2$); MS (El): m/e 364 (M+1 for the free base); HRMS: 363.1737 (363.1735 calcd. for C$_{25}$H$_{21}$N$_3$).

EXAMPLE 19
N-(5-acenaphthyl)-N'-(2,5-dibromophenyl)guanidine•HCl

Preparation: As per Method A of Example 1. Yellow tint solid; mp: 194°–96° C.; TLC (CHCl$_3$:CH$_3$OH; 9:1): R$_f$=0.33; $^1$H NMR (CD$_3$OD): δ 7.74–7.34 (m, 8H, Ar—H), 3.50–3.42 (m, 4H, 2×CH$_2$); HRMS: 442.9678 (442.9633 calcd. for C$_{19}$H$_{15}$Br$_2$N$_3$).

EXAMPLE 20
N-(5-acenaphthyl)-N'-(3,4-dimethoxyphenyl)guanidine•HCl

Preparation: As per Method A of Example 1. Brown solid; mp: 152°–55° C.; TLC (CHCl$_3$:CH$_3$OH; 10:1): R$_f$=0.27; 1H NMR (CD$_3$OD): δ 7.70–7.58 (m, 2H, Ar—H), 7.47 (d, 1H, J=Hz, Ar,H), 7.41–7.35 (m, 2H, Ar—H), 7.04–6.92 (m, 3H, Ar—H), 3.85 (s, 3H, CH$_3$), 3.84 (s, 3H, CH$_3$), 3.47–3.44 (m, 2H, 2×CH$_2$); HRMS: 347.1637 (347.1634 calcd. for C$_{21}$H$_{21}$O$_2$N$_3$).

EXAMPLE 21
N-(5-acenaphthyl)-N'-(4-methoxy-1-naphthyl)-N-methylguanidine•HCl Preparation: As per Method B of Example 2. Light yellow solid; mp: 158°–59° C.; TLC (CHCl$_3$:CH$_3$OH; 10:1): R$_f$=0.25; $^1$H NMR (CD$_3$OD): δ 8.30–6.90 (m, 11H, Ar—H), 4.03 (s, 3H, OCH$_3$), 3.64 (bs, 3H, N—CH$_3$), 3.50–3.41 (m, 4H, 2×CH$_2$); HRMS: 381.1850 (381.1841 calcd. for C$_{25}$H$_{23}$ON$_3$).

EXAMPLE 22
N-(5-acenaphthyl)-N'-(4-methoxy-1-naphthyl)-N'-methyl guanidine•HCl Preparation: As per Method B of Example 2, except that N-ethyl-N-(4-methoxy-1-naphthyl) cyanamide was reacted with 5-acenaphthyl-1-amine hydrochloride. White solid; mp: 195°–97° C.; TLC (CHCl$_3$:CH$_3$OH; 10:1): R$_f$=0.10; $^1$H NMR (CD$_3$OD): δ 8.37 (d, 1 H, J=8.4 Hz, Ar—H), 7.95–7.28 (m, 9H, Ar—H), 7.05 (d, 1H, J=8.3 Hz, Ar—H), 4.07 (s, 3H, OCH$_3$), 3.60 (bs, 3H, N—CH$_3$), 3.47–3.31 (m, 4H, 2×CH$_2$); HRMS: 381.1840 (381.1841 calcd. for C$_{25}$H$_{23}$ON$_3$).

EXAMPLE 23
N-(5-acenaphthyl)-N'-(4-methoxy-1-naphthyl)-N,N'-dimethyl guanidine•HCl Preparation: As per Method C of Example 3. White solid; mp: 210°–12° C.; TLC (CHCl$_3$:CH$_3$OH; 10:1): R$_f$=0.34; $^1$H NMR (CD$_3$OD): δ 7.95 (d, 1H, Ar—H), 7.38–6.65 (m, 10H, Ar—H), 3.82 (s, 3H, OCH$_3$), 3.48 (s, 3H, N—CH$_3$), 3.42 (s, 3H, N—CH$_3$), 3.25–3.18 (m, 2H, CH$_2$), 3.04–2.65 (m, 2H, CH$_2$); HRMS: 395.2005 (395.1998 calcd. for C$_{26}$H$_{25}$ON$_3$).

EXAMPLE 24
N-(5-acenaphthyl)-N'-(4-chloro-1-naphthyl)guanidine•HCl

Preparation: As per Method A of Example 1. White solid; mp: 258°–60° C.; $^1$H NMR (CD$_3$OD); δ 8.38–8.35 (m, 1H, Ar—H), 8.15–8.11 (m, 1H, Ar—H), 7.81–7.34 (m, 9H, Ar—H), 3.44–3.41 (m, 4H, 2×CH$_2$); MS (El): m/e 372 (M+1 for free base); Anal. Calcd. for C$_{23}$H$_{19}$ Cl$_2$N$_3$ (408.31): C, 57.65; H, 4.69; N, 10.29; Found: C, 67.58; H, 4.60; N, 10.28; HPLC (CH$_3$CN:H$_2$O 50:50 with 0.1% TFA): 99.9% pure.

EXAMPLE 25
N-(5-acenaphthyl)-N'-(3,4,5-trichlorophenyl)guanidine•HCl

Preparation: As per Method A of Example 1. White solid; mp: 234°–36° C.; TLC: R$_f$=0.28 (CH$_2$Cl$_2$/CH$_3$OH: 9:1); $^1$H NMR (CD$_3$OD): δ 7.68–7.35 (m, 7H, Ar—H), 3.53–3,40

(m, 4H, 2×CH$_2$); HRMS: 381.0251 (389.0253 calcd. for C$_{19}$H$_{14}$Cl$_3$N$_3$); HPLC (CH$_3$CN:H$_2$O 50:50 with 0.1% TFA): 95.5% pure.

EXAMPLE 26
N-(5-acenaphthyl)-N'-(4-bi-phenyl)guanidine•CH$_3$SO$_3$H

Preparation: As per Method A of Example 1. White solid; mp: 196°–98° C.; TLC (CHCl$_3$:CH$_3$OH; 10:1): R$_f$=0.29, $^1$H NMR (CD30D) δ 7.75–7.36 (m, 14H, Ar—H), 3.45 (bs, 4H, 2×CH$_2$), 2.69 (s, 3H, CH$_3$); HRMS: 363.1737 (363.1735 calcd. for C$_{25}$H$_{21}$N$_3$).

EXAMPLE 27
N-(5-acenaphthyl)-N'-(2,3,4,5-tetrachlorophenyl)guanidine•HCl

Preparation: As per Method A of Example 1. White solid; mp: 223°–25° C.; TLC (CH$_2$Cl$_2$/CH$_2$OH; 9:1): R$_f$=0.51; $_1$H NMR (CD$_3$OD): δ 7.74–7.33 (m, 6H, Ar—H), 3.47–3.40 (m, 4H, 2×CH$_2$); Anal Calcd. for C$_{19}$H$_{13}$Cl$_4$N$_3$ (461.59): C, 49.44; H, 3.06; N. 9.1; Found: C, 50.89; H, 3.15; N, 8.84; HRMS found: 422.9875 (422.9864 Calcd. for C$_{19}$H$_{13}$Cl$_4$N$_3$); HPLC (CH$_3$CN:H$_2$O 45:55 with 0.1% TFA): 95.5% pure.

EXAMPLE 28
N-(5-acenaphthyl)-N'-(3-isopropylphenyl)guanidine•HCl

Preparation: As per Method A of Example 1. White solid; mp: 149°–51° C.; TLC (CHCl$_3$:CH$_3$OH; 10:1): R$_f$=0.28; $_1$H NMR (CD$_3$OD): δ 7.66–7.19 (m, 9H, Ar—H), 3.44 (bs, 4H, 2×CH$_2$), 3.00–2.89 (m, 1H, —CH—), 1.26 (d, 6H, J=7 Hz, 2×CH$_3$); HRMS: 329.1873 (329.1892 calcd. for C$_{23}$H$_{25}$N$_3$).

EXAMPLE 29
N-(5-acenaphthyl)-N'-(3-tert-butylphenyl)guanidine•HCl

Preparation: As per Method A of Example 1. White solid; mp: 176°–78° C.; TLC (CHCl$_3$:CH$_3$OH; 10:1): R$_f$=0.26; $^1$H NMR (CD$_3$OD): δ 7.68–7.28 (m, 9H, Ar—H), 3.45–3.44 (m, 4H, 2×CH$_2$), 1.33 (s, 3H, CH$_3$); HRMS: 343.2055 (343.2048 calcd. for C$_{22}$H$_{23}$N$_3$).

EXAMPLE 30
N-(5-acenaphthyl)-N'-(2,3,5,6-tetrachlorophenyl)guanidine•CH$_3$SO$_3$H Preparation: As per Method A of Example 1. White solid; mp: 248°–50° C.; $_1$H NMR (CD$_3$OD): δ 8.12–7.33 (m, 6H, Ar—H), 3.44–3.40 (m, 4H, 2×CH$_2$), 2.69 (s, 3H, CH$_3$); MS (El): m/e 426 (M+1 for the free base).

EXAMPLE 31
N-(5-acenaphthyl)-N'-(3-iodophenyl)guanidine•HCl

Preparation: As per Method A of Example 1. White solid; mp: 203°–04° C.; TLC (CHCl$_3$:CH$_3$OH; 10:1): R$_f$=0.19; $^1$H NMR (CD$_3$OD): δ 7.76–7.58 (m, 4H, Ar—H), 7.47 (d, 1H, J=7.33 Hz, Ar—H), 7.42–7.34 (m, 3H, Ar—H), 7.22 (t, 1H, J=8 Hz, Ar—H), 3.45–3.44 (m, 4H, 2×CH$_2$); HRMS: 413.0395 (413.0389 calcd. for C$_{19}$H$_{16}$IN$_3$).

EXAMPLE 32
N-(5-acenaphthyl)-N'-(3-nitrophenyl)guanidine•HCl

Preparation: As per Method A of Example 1. Yellow solid; mp: 244°–48° C.; TLC (CHCl$_3$:CH$_3$OH; 10:1): R$_f$=0.16; $^1$H NMR (CD$_3$OD): δ 8.25–8.16 (m, 2H, Ar—H), 7.80–7.58 (m, 4H, Ar—H), 7.51 (d, 1H, J=7.24 Hz, Ar—H), 7.41 (d, 1H, J=6.9 Hz, Ar—H), 7.37 (d, 1H, J=7.4 Hz, Ar—H); HRMS: 332.1276 (332.1273 calcd. for C$_{19}$H$_{16}$N$_4$O$_2$).

EXAMPLE 33
N-(5-acenaphthyl)-N'-(5-indolinyl)guanidine•HCl

Preparation: As per Method A of Example 1. Yellow-white solid; mp: 147°–48° C.; TLC (CHCl$_3$:CH$_3$OH; 10:1): R$_f$=0.27; $^1$H NMR (CD$_3$OD): δ 7.65–7.57 (m, 2H, Ar—H), 7.46 (d, 1H, J=7.3 Hz, Ar—H), 7.41–7.29 (m, 3H, Ar—H), 7.22 (bs, 1H, Ar—H), 7.12 (dd, 1H, J=7.9 and 2.1 Hz, Ar—H), 3.47–3.43 (m, 4H, 2×CH$_2$), 2.92 (dd, 4H, J=14.8 and 7.4 Hz, 2×Ar—CH$_2$), 2.10 (m, 2H, CH$_2$); HRMS: 327.1742 (327.1735 calcd. for C$_{22}$H$_2$IN$_3$).

EXAMPLE 34
N-(5-acenaphthyl)-N'-(3-acenaphthyl)guanidines•CH$_3$SO$_3$H

Preparation: As per Method A of Example 1. White solid; mp: 245° C., $^1$H NMR (300 MHz, CD$_3$OD): δ 7.69–7.73 (m, 2H, Ar—H), 7.60–7.65 (m, 2H, Ar—H); 7.49–7.53 (m; 2H, Ar—H); 7.35–7.48 (m, 4H, Ar—H); 3.41–3.49 (m, 4H, 2×CH$_2$); 2.68 (s, 3H, CH$_3$); MS (El): m/e 363 (M+for free base); Elemental analysis for C$_{25}$H$_{21}$N$_3$.CH$_3$SO$_3$H.2H$_2$O: Calcd: C, 61.62; H, 5.76; N, 8.28; S, 6.32; Found: C, 61.77; H, 5.43; N, 8.22; S, 5.47; HPLC (AcCN: H$_2$O 1:1): 99.3% pure.

EXAMPLE 35
N-(5-acenaphthy)-N'-(2-fluorenyl)guanidine•HCl

Preparation: As per Method A of Example 1. Buff white solid: mp: 239°–240° C.; 7H NMR (300 MHz, CD$_3$OD): δ 7.90–7.92 (d, J=8 Hz, 1H, Ar—H), 7.82–7.84 (d, J=7 Hz, 1H, Ar—H) 7.69–7.72 (d, 1H, J=8 Hz, Ar—H); 7.62–7.64 (m, 3H, Ar—H); 7.48–7.51 (d, J=7.5 Hz, 1H, Ar—H); 7.29–7.41 (m, 5H, Ar—H); 3.95 (s, 2H, CH$_2$); 3.40–3.47 (m, 4H, 2-CH$_2$); MS (El): m/e 375 (M+for free base): Elemental analysis for C$_{26}$H$_{21}$N$_3$.HCl.0.25H$_2$O: Calcd: C, 74.99; H, 5.44; N, 10.08; Found: C, 75.25; H, 5.44; N, 10.14.

EXAMPLE 36
N-(5-acenaphthyl)-N'-(4-n-butoxyphenyl)guanidines•HCl

Preparation: As per Method A of Example 1. Brownish solid; mp: 90° C.; $^1$H NMR (300 MHz, CD$_3$OD): δ 7.57–7.67 (m, 2H, Ar—H), 7.45–7.47 (d, J=7.5 Hz, 1H, Ar—H); 7.34–7.40 (m, 2Hm Ar—H); 7.27–7.30 (m, 2H, Ar—H); 6.99–7.02 (m, 2H, Ar—H); 3.97–4.02 (t, 2H, 0-CH$_2$); 3.41–3.47 (m, 4H, 2-CH$_2$); 1.71–1.78 (dt, 2H, CH$_2$): 1.46–1.54 (m, 2H, CH$_2$); 0.95–1.00 (t, 3H, CH$_3$); MS (El): m/e 359 (M+for free base); Elemental analysis for C$_{23}$H$_{25}$N$_3$O.HCl.0.75H$_2$O: Calcd: C, 67,47; H, 6.77; N, 10.26; Found: C, 67.66; H, 6.67; N, 10.26.

EXAMPLE 37
N-(5-acenaphthyl)-N'-(3-(2-methoxy)dibenzofuranyl)guanidine•HCl

Preparation: As per Method A of Example 1. White solid; mp: 230° C.; $^1$H NMR (300 MHz, CD$_3$OD): δ 8.06–8.09 (dd, J1=7.5 Hz, J2=1.5 Hz, 1H, Ar—H), 7.80 (s, 1H, Ar—H), 7.73–7.76 (d, J=7.5 Hz, 1H, Ar—H), 7.60–7.65 (m, 3H, Ar—H), 7.46–7.56 (m, 2H, Ar—H), 7.34–7.40 (m, 3H, Ar—H), 4.10 (s, 3H, O-CH$_3$), 3.40–3.43 (m, 4H, 2-CH$_2$); MS (El): m/e 407 (M+for free base); Elemental analysis for C$_{26}$H$_{21}$N$_3$O$_2$.HCl.0.25H$_2$: Calcd: C, 69,64; H, 5.06; N, 9.36; Found: C, 69.68; H, 4.98; N, 9.40.

EXAMPLE 38
N-(5-acenaphthyl)-N'-(9-hydroxy-2-fluorenyl)guanidine•HCl

Preparation: As per Method A of Example 1. White solid; mp: 265° C.; $^1$H NMR (300 MHz, CD$_3$OD): δ 7.80–7.83 (d, J=8 Hz, 1H, Ar—H), 7.69–7.74 (t, 2H, Ar—H), 7.60–7.64

(m, 3H, Ar—H), 7.49–7.52 (d, J=7.5 Hz, 1H, Ar—H), 7.34–7.42 (m, 5H, Ar—H), 5.58 (s, 1H, —OH), 3.45 (brs, 4H, 2-CH$_2$); MS (El): m/e 391 (M+for free base); Elemental analysis for C$_{26}$H$_{21}$N$_3$O. HCl.0.25H$_2$O: Calcd: C, 72.22; H, 5.24; N, 9.7; Found: C, 72.35; H, 5.35; N, 9.58.

EXAMPLE 39
N-(5-acenaphthyl)-N'-(4-trifluoromethylphenyl) guanidine•HCl

Preparation: As per Method A of Example 1. White solid; mp: 234°–236° C.; TLC (CH$_2$Cl$_2$:CH$_3$OH 9:1): R$_f$=0.4; 1H NMR (CDCl$_3$): 7.70–7.25 (m, 9H, Ar—H), 3.46–3.38 (m, 4H, 2×—CH$_2$); MS(Cl): m/e 356 (M+1); Anal Calcd. for C$_2$OH$_{16}$N$_3$F$_3$.HCl (391.82): C, 61.31; H, 4.37; N, 10.72; Found: C, 62.14; H, 4.34; N, 10.80.

EXAMPLE 40
N-(5-acenaphthyl)-N'-(4-methylthiophenyl) guanidine•HCl

Preparation: As per Method A of Example 1. White solid; mp: 168°–170° C.; TLC (CH$_2$Cl$_2$:CH$_3$OH 9:1): R$_f$=0.38; 1H NMR (CD$_3$OD): 7.76–7.38 (m, 9H, Ar—H), 3.53–3.37 (m, 4H, 2×—CH$_2$), 2.57 (s, 3H, —SCH$_3$); MS(Cl): m/e 334 (M+1); Anal. Calcd. for C$_{20}$H$_{19}$N$_3$S.HCl (369.91): C, 64.94; H, 5.45; N, 11.36; Found: C, 64.38; H, 5.73; N, 11.05.

EXAMPLE 41
N-(5-Acenaphthyl)-N'-(4-benzyloxyphenyl) guanidine•HCl

Light green foam; mp: 117°–127° C.; TLC (CH$_2$Cl$_2$:CH$_3$OH; 15:1): R$_f$=0.50; $^1$H NMR (CD$_3$OD): 7.646–7.094 (m, Ar—H, 14H), 5.127 (s, CH$_2$, 2H), 3.454–3.449 (m, CH$_2$CH$_2$, 4H); Anal. Calcd. for C$_{26}$H$_{23}$N$_3$O.HCl (429.95): C, 72.63; H, 5.63; N, 9.77; Found: C, 72.20; H, 5.70; N, 9.65.

EXAMPLE 42
N-(5-Acenaphthyl)-N'-(3-benzyloxyphenyl)guanidine•HCl

Light green foam; mp: 94°–98° C.; TLC (CH$_2$Cl$_2$:CH$_3$OH; 15:1): R$_f$=0.50; $^1$H NMR (CD$_3$OD): 7.639–6.981 (m, Ar—H, 14H), 5.117 (s, CH$_{26}$,2H), 3.451–3.344 (m, CH$_2$CH$_2$, 4H); Anal. Calcd. for C$_{26}$H$_{23}$N$_3$O.HCl.0.5H$_2$O (438.95): C, 71.07; H, 5.70; N, 9.57; Found: C, 71.44; H, 5.60; N, 9.83.

EXAMPLE 43
N-(5-Acenaphthyl)-N'-(3-benzyloxyphenyl) guanidine•Mesylate

Light yellow foam; mp: 90°–98° C.; TLC (AcOEt:CH$_3$OH; 10:1): R$_f$=0.30; $^1$H NMR (CDCl$_3$): 7.647–7.268 (m, Ar—H, 11H), 6.956–6.923 (m, Ar—H, 3H), 5.086 (s, CH$_2$, 2H), 3.458–3.410 (m, CH$_2$CH$_2$, 4H), 2.857 (s, CH$_3$, 3H); Anal. Calcd. for C$_{27}$H$_{27}$N$_3$O4S (489.59): C, 66.24; H, 5.56; N, 8.58; Found: C, 66.99; H, 5.35; N, 8.74.

EXAMPLE 44
N-(5-Acenaphthyl)-N'-(3-sec-butylphenyl) guanidinee•Mesylate White solid; mp: 136°–138° C.; TLC (CH$_2$Cl$_2$: MeOH; 15:1): R$_f$=0.31; $^1$H NMR (CD$_3$OD): 7.668–7.164 (m, 9H, Ar—H), 3.483–3.411 (m, CH$_2$CH$_2$, 4H), 2.655–2.627 (m, CH, 1H), 1.656–1.589 (m, CH$_2$, 2H), 1.257–1.234 (d, J=6.87 Hz, CH$_2$,3H), 0.860–0.813 (m, CH$_3$, 3H); Anal. Calcd. for C$_{23}$H$_{26}$N$_3$Cl (379.93): C, 72.71; H, 6.90; N, 11.06; Found: C, 72.73; H, 6.75; N, 11.12.

EXAMPLE 45
N-(5-Acenaphthyl)-N'-(2-anthracenyl)guanidine•HCl

Green solid; mp: 260°–262° C.; TLC (CH$_2$Cl$_2$: MeOH; 15:1): R$_f$=0.31; $^1$H NMR (CD$_3$OD): 8.527–8.502 (d, Ar—H, J=7.63 Hz, 2H), 8.183–8.153 (d, Ar—H, J=9.28 Hz, 1H), 8.044 (s, br, Ar—H, 3H), 7.771–7.617 (m, Ar—H, 2H), 7.542–7.368 (m, 6H, Ar—H), 3.449–3.418 (m, CH$_2$CH$_2$, 4H); Anal. Calcd. for C$_{27}$H$_{22}$N$_3$Cl (423.50): C, 76.50; H, 5.23; N, 9.91; Found: C, 76.33; H, 5.46; N, 9.70.

EXAMPLE 46
N-(5-Acenaphthyl)-N'-(3-phenethylphenyl)guanidine•HCl

White solid; mp: 116°–118° C.; TLC (CH$_2$Cl$_2$:MeOH; 15:1): R$_f$=0.31; $^1$H NMR (CD$_3$OD): 7.645–7.156 (m, Ar—H, 14H), 4.233–4.161 (q, CH, J=7.14 Hz, 1H), 3.478–3.414 (m, CH$_2$CH$_2$, 4H), 1.650–1.626 (d, J=7.20 Hz, CH$_3$, 3H); Anal. Calcd. for C$_{27}$H$_{26}$N$_3$Cl (427.98): C, 75.77; H, 6.12; N, 9.82; Found: C, 75.63; H, 5.98; N, 9.69.

EXAMPLE 47
N-(5-Acenaphthyl)-N'-(4-adamantylphenyl)guanidine•HCl

White solid; mp: 240° C.; TLC (CH$_2$Cl$_2$:MeOH; 15:1): R$_f$=0.31; $^1$H NMR (CD$_3$OD): 7.639–7.289 (m, Ar—H, 9H), 3.443–3.403 (m, CH$_2$CH$_2$, 4H), 2.086–1.756 (m, CH's, 13H); Anal. Calcd. for C$_{29}$H$_{32}$N$_3$Cl (458.08): C, 76.04; H, 7.04; N, 9.17; Found: C, 75.97; H, 6.88; N, 9.06.

EXAMPLE 48
N-(5-Acenaphthyl)-N'-(3-benzyloxyphenyl)-N'-methylguanidine•HCl

White solid; mp: 102°–105° C.; TLC (CH$_2$Cl$_2$: MeOH; 15:1); R$_f$=0.30; $^1$H NMR (CD$_3$OD): 7.605–7.134 (m, 14H, Ar—H), 5.149 (s, CH$_2$, 2H), 3.636 (s, CH$_3$, 3H), 3.532–3.444 (m, CH$_2$CH$_2$, 4H); Anal. Calcd. for C$_{27}$H$_{26}$N$_3$ClO (443.98): C, 73.04; H, 5.98; N, 9.46; Found: C, 72.98; H, 5.95; N, 9.42.

EXAMPLE 49
N-(5-Acenaphthyl)-N'-(4-benzyloxyphenyl)-N'-methylguanidine•HCl

White solid; mp: 108°–110° C.; TLC (CH$_2$Cl$_2$:MeOH; 15:1); R$_f$=0.30; $^1$H NMR (CD$_3$OD): 7.605–7.134 (m, 14H, Ar—H), 5.149 (s, CH$_2$, 2H), 3.536 (s, CH$_3$, 3H), 3.532–3.444 (m, CH$_2$CH$_2$, 4H); Anal. Calcd. for C$_{27}$H$_{26}$N$_3$ClO (443.98): C, 73.04; H, 5.98; N, 9.46; Found: C, 72.93; H, 6.00; N, 9.919.

EXAMPLE 50
N-(5-Acenaphthyl)-N'-(3-biphenyl)-N'-methylguanidine•HCl

White solid; mp: 217° C.; TLC (CH$_2$Cl$_2$:MeOH; 10:1): R$_f$=0.30; $^1$H NMR (CDCl$_3$): 7.513–7.022 (m, 14H, Ar—H), 3.668 (s, CH$_3$, 3H), 3.322–3.203 (m, CH$_2$CH$_2$, 4H); Anal. Calcd. for C$_{26}$H$_{24}$N$_3$Cl.2H$_2$O (449.98): C, 69.40; H, 6.27; N, 9.34; Found: C, 69.25; H, 6.27; N, 9.48.

EXAMPLE 51
N-(5-Acenaphthyl)-N'-(3-(1'-methyl-2'-phenyl)ethyl) guanidine•HCl White solid; mp: 106°–108° C.; TLC (CH$_2$Cl$_2$:MeOH; 15:1) R$_f$=0.36; $^1$H NMR (CD$_3$OD): 7.698–7.070 (m, 14H, Ar—H), 3.467–3.312 (m, CH$_2$CH$_2$, 4H), 3.105–3.033 (m, CH, 1H), 2.928–2.810 (m, CH$_2$, 2H), 1.267–1.244 (d, J=6.87 Hz, CH$_3$, 3H); Anal. Calcd. for C$_{28}$H$_{28}$N$_3$Cl (442.00): C, 76.09; H, 6.39; N, 9.51; Found: C, 76.11; H. 6.55; N, 9.38.

EXAMPLE 52
N-(5-Acenaphthyl)-N'-(3,4-tetralinylphenyl) guanidine•HCl

White solid; mp: 158°–160° C.; TLC (CH$_2$Cl$_2$:MeOH; 15:1): R$_f$=0.36; $^1$H NMR (CDCl$_3$): 7.631–6.985 (m, 8H, Ar—H), 3.484–3.373 (m, CH$_2$'s, 4H), 2.747 (m, CH$_2$, 2H), 1.793–1.784 (m, CH$_2$, 2H); Anal. Calcd. for C$_{23}$H$_{24}$Cl (377.92): C, 73.10; H, 6.40; N, 11.12; Found: C, 72.88; H, 6.25; N, 11.03.

EXAMPLE 53
N-(5-Acenaphthyl)-N'-(7-benzyltetralinyl)guanidine•HCl

White solid; mp: 161°–162° C.; TLC (AcOEt:MeOH; 10:1) Rf=0.44; $^1$H NMR; 7.647–7.118 (m, Ar—H, 13H); Anal. Calcd. for C$_{30}$H$_{30}$N$_3$Cl.½H$_2$O (477.04): C, 75.47; H, 6.50; N, 8.81; Found: C, 75.23; H, 6.28; N, 8.82.

EXAMPLE 54
N-(5-Acenaphthyl)-N'-(3,4-dibenzyloxyphenyl) guanidine•Mesylate

White solid; mp: 185°–187° C.; TLC (AcOEt:MeOH; 10:1) Rf=0.44; $^1$H NMR; 7.647–7.118 (m, Ar—H, 13H); Anal. Calcd. for C$_{30}$H$_{30}$N$_3$O$_5$S.H$_2$O (613.73): C, 66.54; H, 5.75; N, 6.85; Found: C, 66.86; H, 5.36; N, 6.92.

EXAMPLE 55
N-(5-Acenaphthyl)-N'-(3-1-(4-ethoxy)phenyl)propanyl) phenyl)guanidine•Mesylate White solid; mp: 93°–95° C.; TLC (AcOet:MeOH; 10:1): R$_f$=0.0.49; $^1$H NMR; 7.636–7.575 (m, Ar—H, 2H), 7.416–7.128 (m, Ar—H, 11H), 6.922 (s, Ar—H, 1H), 6.871–6.842 (d, Ar—H, J=8.72 Hz, 2H), 6.639–6.610 (d, Ar—H, J=8.66 Hz, 2H), 3.782–3.748 (q, OCH$_2$, J=7.40 Hz, 2H), 3.498–3.417 (m, CH$_2$CH$_2$, 4H), 3.006–2.980 (m, CH, 1H), 2.848 (s, CH$_3$, 3H), 2.835–2.706 (m, CH$_2$, 2H), 1.317–1.193 (m, CH$_3$, CH$_3$, 6H); Anal. Calcd. for C$_{31}$H$_{35}$N$_3$O$_4$S (545.70): C, 68.23; H, 6.46; N, 7.70; Found: C, 68.30; H, 6.44; N, 7.85.

EXAMPLE 56
N-(5-Acenaphthyl)-N'-(3-(N'',N''-dibenzyl)aminophenyl) guanidinee•Mesylate White solid; mp: 150°–152° C.; TLC (AcOEt:MeOH; 10:1) Rf=0.44; 1H NMR; 7.568–7.174 (m, Ar—H, 17H), 6.745–6.530 (m, Ar—H, 2H), 4.697 (s, CH$_2$, 2H), 3.497–3.413 (m, CH$_2$CH$_2$, 4H), 2.825 (s, CH$_3$, 3H); HRMS: 482.2446 (482.628 calcd. for C$_{33}$H$_{30}$N$_4$).

EXAMPLE 57
N-(5-Acenaphthyl)-N'-(3-(1'-benzylbutyl)phenyl) guanidine•Mesylate White solid; mp: 90°–92° C.; TLC (AcOEt:MeOH; 10:1); Rf=0.48; $^1$H NMR (CDCl$_3$): 7.655–7.558 (m, Ar—H, 2H), 7.411–7.269 (m, Ar—H, 5H), 7.169–6.800 (m, Ar—H, 7H), 3.492–3.414 (m, CH$_2$CH$_2$, 4H), 3.022–2.662 (m, CH$_2$, CH, 3H), 2.842 (s, CH$_3$, 3H), 1.733–1.695 (m, CH$_2$, 2H), 1.252–1.176 (m, CH$_2$, 2H), 0.895–0.847 (t, CH$_3$, J=7.28 Hz); HRMS: 433.2516 (433.5962 calcd. for C$_{30}$H$_{31}$N$_3$).

EXAMPLE 58
N-(5-Acenaphthyl)-N'-3-(4-tert-butylbenzoxymethyl) phenylguanidine•Mesylate White solid; mp: 113°–115° C.; TLC (AcOEt:MeOH; 10:1): R$_f$=0.39; $^1$H NMR (CDCl$_3$): 7.681–7.267 (m, Ar—H, 11H), 6.904–6.875 (d, Ar—H, J=8.92 Hz, 2H), 5.067 (s, CH$_2$, 2H), 3.498–3.434 (m, CH$_2$CH$_2$, 4H), 2.856 (s, CH$_3$, 3H), 1.278 (s, tert-butyl, 9H); HRMS: 449.2452 (449.5956 calcd. for C$_{30}$H$_{31}$ON$_3$).

EXAMPLE 59
N-(5-Acenaphthyl)-N'-2(2-indolyl)phenylguanidine HCl mp: 174°–176° C.; TLC: R$_f$=0.32 (SiO$_2$, CHCl$_3$/MeOH= 10:1); $^1$H NMR (CD$_3$OD): δ ppm 6.86–7.83 (m, AR$\underline{H}$, 14H), 3.30–3.40 (m, CH$_2$, 4H); MS(El): m/e 402.2 (M+: C$_{27}$H$_{22}$N$_4$); Anal. (C,H,N; C$_{27}$H$_{22}$N$_4$.HCl): Calcd.(%): C, 70.33; H, 5.58; N, 12.16; Found (%): C, 70.01; H, 5.65; N, 11.56.

EXAMPLE 60
N-(5-Acenaphthyl)-N'-(phenyl-3-bromo)guanidine HCl mp: 204°–205° C.; TLC: R$_f$=0.20 (SiO$_2$, CHCl$_3$/MeOH= 10:1); $^1$H NMR (CD$_3$OD): δ ppm: 7.35–7.68 (m, Ar$\underline{H}$), 3.4–3.5 (m, CH$_2$, 4H); MS(El): m/e 365.0 (M+: C$_{19}$H$_{16}$N$_3$Br); Anal. (C,H,N; C$_{19}$H$_{16}$N$_3$BR.HCl): Calcd. (%): C, 56.67; H, 4.25; N, 10.43; Found (%): C, 56.49; H, 4.43; N, 10.18.

EXAMPLE 61
N-(5-Acenaphyl)-N'-(2,3,4-trichlorophenyl)-N,N'dimethyl guanidine HCl TLC: R$_f$=0.14 (SO$_2$, CHCl$_3$/MeOH=10:1); $^1$H NMR (CD$_3$OD): δ ppm: 6.72–7.44 (m, Ar$\underline{H}$, 7H), 3.5–3.6 (s, CH$_3$, 6H), 3.4–3.5 (m, CH$_2$, 4H); MS(El): m/e 418.0 (M$^+$: C$_{21}$H$_{18}$N$_3$Cl$_3$); Anal. (C,H,N; C$_{21}$H$_{18}$N$_3$Cl$_3$.HCl): Calcd. (%): C, 55.41; H, 4.21; N, 9.23; Found (%): C, 55.26; H, 4.11; N, 9.03.

EXAMPLE 62
N-(5-Acenaphyl)-N'-(2,3,4-trichlorophenyl)-N'-methylguanidine HCl mp: 229°–231° C.; TLC: R$_f$=0.19 (SiO$_2$CHCl$_3$/MeOH= 10:1); $^1$H NMR (CD$_3$OD): δ ppm: 7.54–7.70 (m, Ar$\underline{H}$, 4H), 7.33–7.40(m, Ar$\underline{H}$, 3H); MS (El): m/e 403.1 (M+: C$_{20}$H$_{16}$N$_3$Cl$_3$); Anal. (C,H,N; C$_{20}$H$_{16}$N$_3$Cl$_3$HCl): Calcd. (%): C, 54.45; H, 3.88; N, 9.52; Found (%): C, 54.23; H, 4.01; N, 9.36.

EXAMPLE 63
N-(5-Acenaphyl)-N'-(4-(2'-benzothiazole-6'-methyl) phenyl)guanidine•HCl mp: 244.5°–246° C.; TLC: R$_f$=0.23 (SiO$_2$, CHCl$_3$/MeOH=10:1); $^1$H NMR (CD$_3$OD): δ ppm 8.15–8.17 (m, Ar$\underline{H}$, 2H), 7.36–7.91 (m, Ar$\underline{H}$, 10H), 3.40–3.50 (m, C$\underline{H}_2$, 4H), 2.50 (s, C$\underline{H}_3$, 1H); MS(El): m/e 434.1 (M$^+$: C$_{27}$H$_{22}$N$_4$S); Anal. (C,H,N; C$_{27}$H$_{22}$N$_4$S.HCl): Calcd. (%): C, 68.85; H, 4.92; N, 11.89; Found (%): C, 68.66; H, 4.91; N, 11.86.

EXAMPLE 64

Inhibition of Glutamate Release

Compounds were tested for inhibition of glutamate release. As shown by the data below, compounds of the invention blockers of glutamate release. The assay protocol was as described in PCT/US92/01050, specifically Examples 8–9 of that document.

Briefly, the test compound is first dissolved in methanol to make a stock of 20 mM. This solution is diluted into the basal buffer as well as high-K$^+$ buffer to give the required concentration of the compound as specified in Table I below, i.e., 10 μM or 3 μm. All solutions including the controls are made to have the same concentration of methanol. Methanol concentration never exceeded 0.3% (v/v) of buffers. Synaptosomes were first exposed to the compound during the wash before superfusion and also during the entire superfusion protocol. The total time synaptosomes were exposed to the test organic compounds before the glutamate release was <25 sec.

The relative levels of glutamate release in the presence of the specified compounds of the invention are shown in Table I and Table 1A below. In those Tables, the tested compounds are identified by reference to corresponding Example No.

and the following formula where the substituent groups R, $R^1$ and $R^2$ are specified in the Tables. The designation "NT" in the Tables indicates the compound was not tested in the specified assay.

A number of compounds identified in Table I and Table 1A were also tested in a veratridine induced glutamate release assay and similar results of glutamate release inhibition were observed. The protocol of the veratridine induced glutamate release assay is described in Epilepsia, 27: 490–497 (1986).

TABLE I

INHIBITION OF GLUTAMATE RELEASE

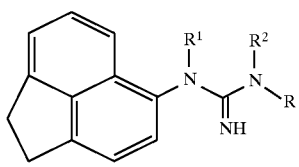

| Cmpd. of Ex. No. | R | $R^1$ | $R^2$ | % Block of Glu Rel @ 10 μM | @ 3 μM |
|---|---|---|---|---|---|
| 1 | 2,3,4-trichlorophenyl | H | H | NT | 97 |
| 2 | 5-acenaphthyl | H | $CH_3$ | 62 | NT |
| 3 | 5-acenaphthyl | $CH_3$ | $CH_3$ | NT | 53 |
| 4 | 1-anthracenyl | H | H | 95 | 85 |
| 5 | 4-tertbutylphenyl | H | H | 100 | 49 |
| 6 | 4-cyclohexylphenyl | H | H | NT | 90 |
| 7 | 4-secbutylphenyl | H | H | NT | 84 |
| 8 | 4-methoxyphenyl | H | H | 50 | 3 |
| 9 | 2,3-dichlorophenyl | H | H | 86 | 47 |
| 10 | 4-$OCH_3$-2-naphthyl | H | H | 84 | 80 |
| 11 | 3,4-dichlorophenyl | H | H | 82 | NT |
| 12 | 4-chlorophenyl | H | H | 69 | NT |
| 13 | 2-naphthyl | H | H | 81 | NT |
| 15 | 4-nitrophenyl | H | H | 35 | 78 |
| 16 | 3-bi-phenyl | H | H | NT | 98 |
| 17 | 2,3-dimethylphenyl | H | H | NT | 46 |
| 18 | 2-bi-phenyl | H | H | NT | 54 |
| 19 | 2,5-dibromophenyl | H | H | NT | 46 |
| 20 | 3,4-dimethoxyphenyl | H | H | NT | 46 |
| 21 | 4-methoxy-1-naphthyl | $CH_3$ | H | NT | 54 |
| 22 | 4-methoxy-1-naphthyl | H | $CH_3$ | NT | 43 |
| 23 | 4-methoxy-1-naphthyl | $CH_3$ | $CH_3$ | NT | 40 |
| 24 | 4-chloro-1-naphthyl | H | H | NT | 75 |
| 25 | 3,4,5-trichlorophenyl | H | H | NT | 49 |
| 26 | 4-bi-phenyl | H | H | NT | 38 |
| 27 | 2,3,4,5-tetrachlorophenyl | H | H | NT | 37 |
| 28 | 3-isopropylphenyl | H | H | NT | 64 |
| 29 | 3-tertbutylphenyl | H | H | NT | 71 |
| 34 | 3-acenaphthyl | H | H | NT | 77 |
| 35 | 2-fluorenyl | H | H | NT | 81 |
| 39 | 4-trifluoromethyl | H | H | NT | 52 |
| 40 | 4-methylthio | H | H | NT | 46 |

TABLE 1A

INHIBITION OF GLUTAMATE RELEASE

| Cmpd. of Ex. No. | R | $R^1$ | $R^2$ | % Block of Glu Rel @ 1 μm | @ 0.3 μm |
|---|---|---|---|---|---|
| 41 | 4-benzyloxyphenyl | H | H | — | 38 |
| 42 | 3-benzyloxyphenyl | H | H | — | 24 |
| 45 | 2-anthracenyl | H | H | 44 | — |
| 46 | 3-phenethylphenyl | H | H | 79 | 31 |
| 47 | 4-adamantylphenyl | H | H | 20 | — |

TABLE 1A-continued

INHIBITION OF GLUTAMATE RELEASE

| Cmpd. of Ex. No. | R | $R^1$ | $R^2$ | % Block of Glu Rel @ 1 μm | @ 0.3 μm |
|---|---|---|---|---|---|
| 48 | 3-benzyloxyphenyl | H | $CH_3$ | 83 | 46 |
| 49 | 4-benzyloxyphenyl | H | $CH_3$ | 44 | 11 |
| 50 | 3-(l-methyl-2'-phenylethyl)phenyl) | H | H | 72 | — |
| 51 | 3-biphenyl | H | $CH_3$ | 47 | — |
| 53 | 7-benzyltetralinyl | H | H | 100 | — |
| 56 | 3-(N",N"-dibenzyl)aminophenyl | H | H | — | 7 |
| 57 | 3-(1'-benzylbutyl)phenyl | H | H | — | 23 |
| 58 | 3-(4-t-butylbenzoxy-methylene)phenyl | H | H | — | 19 |
| 62 | 2,3,4-trichlorophenyl | H | $CH_3$ | — | 15 |

EXAMPLE 65

Ca-Flux Assay

Compounds were also tested to determine where the $Ca^{2+}$ dependent and independent components of glutamate release are related to the blockage of $^{45}Ca$ uptake. Calcium uptake is one step in the cascade of events which occur in neuronal cell death from ischemia. See Bassaclough and Leach, *Current Patents Ltd.*, 2–27. The protocol of the Ca-flux assay is as follows and the results of the assay are shown in Table II below. Rat brain synaptosomes were prepared according to Hajos, *Brain Res.*, 93:485 (1975). Synaptosomes were suspended in low potassium "LK" buffer (containing 3 mM KCl) at 2 mg/ml. Test compounds in LK were added to synaptosomes to a final concentration of 10 μM and incubated for 5 minutes at room temperature. $^{45}Ca$ uptake was then measured by adding isotope in either LK or high potassium (150 mM KCl) containing buffer. After 5 seconds, the $^{45}Ca$ flux was stopped with 0.9 mL quench solution (LK+10 mM EGTA). The solution was filtered under vacuum and the filters washed with 15 mL of quench buffer. The effect of drug is expressed as % inhibition (or block) of control potassium-stimulated $^{45}Ca$ influx. This method is an adaptation of the method disclosed by Nachsen and Blaustein, *J. Physiol.*, 361:251–268 (1985). Results of the assay are shown in Table II below. In Table II, the tested compounds are identified by reference to corresponding Example No. and the depicted structural formula where the substituent groups R, $R^1$ and $R^2$ are specified in Table II.

TABLE II

ACTIVITY IN THE Ca FLUX ASSAY

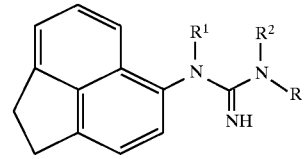

| Cmpd. Ex. No. | R | $R^1$ | $R^2$ | Block of $^{45}$Ca @ 10 μM % Block | $IC_{50}$ μM |
|---|---|---|---|---|---|
| 5 | 4-tertbutylphenyl | H | H | 50 | |
| 6 | 4-cyclohexylphenyl | H | H | 63 | |
| 7 | 4-sec-butylphenyl | H | H | 53 | |
| 10 | 4-methoxy-2-naphthyl | H | H | 43 | 6.35 |
| 16 | 3-bi-phenyl | H | H | | 7.18 |
| 39 | 4-trifluoromethyl | H | H | 52 | |
| 40 | 4-methylthio | H | H | 46 | |

EXAMPLE 66

Sodium Channel Blockade Assay

The ability of compounds of the invention to block sodium channels of mammalian cells is exemplified by the data summarized in Table III below. The data demonstrates that at least some compounds of the invention block the saxitoxin binding site on voltage-activated Na channels which are believed to control glutamate release in vivo. The assay protocol was as described by F. Gusvosky, et al., *Brain Research*, 518: 101–106 (1990). The following solutions were prepared:

1) Stock Solution of the following composition (amounts of components expressed as grams/liter):

| Component | Amount |
|---|---|
| 30 mM KCl | 2.23 |
| 8 mM MgSO$_4$ | 0.96 |
| 250 mM Hepes/Tris | 59.57 (pH to 7.4 with Tris Base) |
| 1 M Choline Chloride | 139.60 |
| 18 mM CaCl2 | 1.99 |

The Stock Solution is made in ddH$_2$O, filtered and stored at room temperature for 4–6 weeks. The Hepes stock is kept refrigerated.

2) Toxin: 1 mg of 1 mM Tetrodotoxin dissolved in 3.1 mls ddH$_2$O (stored at 4° C.).

3) Incubation Buffer of the following composition (amounts of components expressed as mls):

| Component | Amount |
|---|---|
| 5.4 mM KCl | 9.0 |
| 0.8 mM MgSO$_4$ | 5.0 |
| 50 mM Hepes | 10.0 |
| 130 mM Choline Chloride | 6.5 |

19.5 mls of ddH$_2$O and are added to the admixture followed by the addition of 0.049 grams of 5.5 mM glucose to provide the Incubation Buffer. The Incubation Buffer is made on the day of the assay. 4) Wash Buffer of the following composition (amounts of components expressed as mls).

| Component | Amount |
|---|---|
| 163 mM Choline Chloride | 163 |
| 0.8 mM MgSO$_4$ | 100 |
| 1.8 mM CaCl$_2$ | 100 |
| 5.0 mM Hepes | 20 |

617 mls of ddH$_2$O and are added to the admixture to provide the Wash Buffer.

Synaotosome preparation

Synaptosomes were prepared as described in Example 8 of PCT/US92/01050. The prepared synaptosomes are frozen in 1 ml aliquots (5% DMSO) at −80° C. Preparation is thawed on ice immediately before assay and diluted to get approximately 1000 cpm for totals per filter (10–15 μg protein/filter to avoid any potential problems testing relatively lipophilic compounds that could be absorbed out of solution by the membranes).

Assay

A test Assay is prepared of the following composition and having 200 λ final volume:

50 λ.[$^3$H]Saxitoxin: 5.9 nM (Amersham TRK.877) approximately a 1:300 dilution of stock (the [$^3$H] Saxitoxin is stored according to Amersham recommendations)

20 λ Compound of interest (diluted [10×] in ddH$_2$O due to low solubility)

80 λ Incubation buffer

50 λ protein: 10–15 μg rat synaptosomes

This mixture is incubated for 30 minutes at 37° C., then filtered over Whatmann GF/C glass fiber filters, and washed 3× with 4 mls of Wash Buffer, and the filters punched filters to vials immediately upon completion of assay. [$^3$H]STX is very unstable and can lose $^3$H when H$_2$O evaporates while filters dry. 5 mls scintillation fluid (CytoScint ICN #882465) are added and the samples counted for 5 minutes each. Nonspecific binding is determined by 10 μM TTX and is about 5% of total binding at the above [protein].

In Table IIII, the tested compounds are identified by reference to the formula depicted below with the substituent groups of the tested compounds R, $R^1$ and $R^2$ specified in Table ll. The tested compounds were in salt form, as indicated in the Table.

TABLE III

| Cmpd. No. | R | $R^1$ | $R^2$ | Sodium Channel Block vs. $^3$HSTX $IC_{50}$ μm | Salt |
|---|---|---|---|---|---|
| 1 | 1-anthracene | H | H | 1.4 | HCl |
| 2 | 4-methoxy-1-naphthyl | H. | H | 4 | mesylate |
| 3 | 6-benzodioxolyl | H | H | >100 | HCl |
| 4 | 4-tertbutylphenyl | H | H | 25.2 | HCl |
| 5 | 4-sec-butylphenyl | H | H | 34 | HCl |

TABLE III-continued

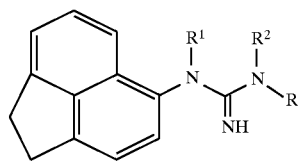

| Cmpd. No. | R | R$^1$ | R$^2$ | Sodium Channel Block vs. $^3$HSTX IC$_{50}$ μm | Salt |
|---|---|---|---|---|---|
| 6 | 5-acenaphthyl | CH$_3$ | H | >100 | HCl |
| 7 | 4-methoxyphenyl | H | H | >100 | HBr |
| 8 | 2,3-dichlorophenyl | H | H | 57.5 | HCl |
| 9 | 4-methoxy-2-naphthyl | H | H | >30 | HCl |
| 10 | 3,4-dichlorophenyl | H | H | 19.9 | HCl |
| 11 | 4-chlorophenyl | H | H | >30 | HBr |
| 13 | 2-naphthyl | H | H | 57.8 | HCl |
| 14 | 4-nitrophenyl | H | H | >100 | HCl |
| 15 | 3-biphenyl | H | H | 7.8 | HCl |
| 16 | 4-fluorophenyl | H | H | >100 | HCl |
| 17 | 2,3-dimethylphenyl | H | H | 21 | HCl |
| 18 | 2,3,4-trichlorophenyl | H | H | >10 | HCl |
| 19 | 3,4,5-trimethoxyphenyl | H | H | >100 | HCl |
| 20 | 2-biphenyl | H | H | 71.1 | HBr |
| 21 | 2,3-difluorophenyl | H | H | >100 | HCl |
| 22 | 2,5-dibromophenyl | H | H | 40.5 | HCl |
| 23 | 2,3,4-trifluorophenyl | H | H | >100 | HCl |
| 24 | 4-methoxy-1-naphthyl | H | H | 23.3 | HCl |
| 25 | 4-methoxy-1-naphthyl | H | CH$_3$ | 63 | HCl |
| 26 | 5-acenaphthyl | H | H | 8.4 | mesylate |
| 27 | 4-methoxy-1-naphthyl | CH$_3$ | CH$_3$ | >100 | HCl |
| 28 | 5-acenaphthyl | CH$_3$ | CH$_3$ | >100 | HCl |
| 29 | 2,4-dichlorophenyl | H | H | 66 | HCl |
| 30 | 2,3,4,5-tetrachlorophenyl | H | H | >3 | HCl |

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A compound having the formula:

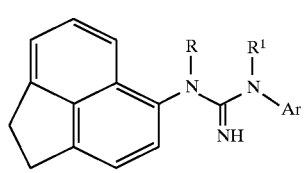

wherein:

R and R$^1$ are each independently hydrogen, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted alkylthio having from 1 to about 20 carbon atoms, substituted or unsubstituted aminoalkyl having from 1 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted alkylsulfonyl having from 1 to about 20 carbon atoms, substituted or unsubstituted carbocyclic aryl having at least about 5 ring atoms, substituted or unsubstituted aralkyl having at least about 5 ring atoms, or a substituted or unsubstituted heteroaromatic or heteroalicyclic group having from 1 to 3 rings, 3 to 8 ring members in each ring and from 1 to 3 hetero atoms, Ar is selected from the group consisting of substituted or unsubstituted carbocyclic aryl having at least 5 carbon atoms, and substituted or unsubstituted heteroaromatic group having 1 to 3 rings, 3 to 8 ring members in each ring and from 1 to 3 hetero atoms; and pharmaceutically acceptable salts thereof.

2. A compound of claim 1 wherein Ar is phenyl independently substituted at one or more positions by halo, haloalkyl, substituted or unsubstituted alkylthio, substituted or unsubstituted alkylsulfinyl, substituted or unsubstituted alkylsulfonyl, substituted or unsubstituted alkoxy, nitro, substituted or unsubstituted carbocyclic aryl, substituted or unsubstituted aralkyl, substituted or unsubstituted aralkylamino, substituted or unsubstituted aryloxy, substituted or unsubstituted alkyleneoxyaryl, or a substituted or unsubstituted heterocyclic group.

3. A compound of claim 1 wherein Ar is substituted or unsubstituted anthracenyl, substituted or unsubstituted indolinyl, substituted or unsubstituted fluorenyl, substituted or unsubstituted bi-phenyl, substituted or unsubstituted dibenzofuranyl or substituted or unsubstituted tetralinyl.

4. A compound of claim 1 wherein the compound is selected from the group of:

N-(5-acenaphthyl)-N'-(2,3,4-trichlorophenyl)guanidine;

N-(5-acenaphthyl)-N'-(2,3,4-trichlorophenyl)-N-methylguanidine;

N-(5-acenaphthyl)-N'-(2,3,4-trichlorophenyl)-N'-methylguanidine;

N-(5-acenaphthyl)-N'-(2,3,4-trichlorophenyl)-N,N'-bis-methylguanidine;

N,N'-bis(5-acenaphthyl)-N-methylguanidine;

N,N'-bis(5-acenaphthyl)-N,N'-bis-methylguanidine;

N-(5-acenaphthyl)-N'-(1-anthracenyl)guanidine;

N-(5-acenaphthyl)-N'-(1-anthracenyl)-N-methylguanidine;

N-(5-acenaphthyl)-N'-(1-anthracenyl)-N'-methylguanidine;

N-(5-acenaphthyl)-N'-(1-anthracenyl)-N,N'-bis-methylguanidine;

N-(5-acenaphthyl)-N'-(4-tert-butylphenyl)guanidine;

N-(5-acenaphthyl)-N'-(4-tert-butylphenyl)-N-methylguanidine;

N-(5-acenaphthyl)-N'-(4-tert-butylphenyl)-N'-methylguanidine;

N-(5-acenaphthyl)-N'-(4-tert-butylphenyl)-N,N'-bis-methylguanidine;

N-(5-acenaphthyl)-N'-(4-cyclohexylphenyl)guanidine;

N-(5-acenaphthyl)-N'-(4-cyclohexylphenyl)-N-methylguanidine;

N-(5-acenaphthyl)-N'-(4-cyclohexylphenyl)-N'-methylguanidine;

N-(5-acenaphthyl)-N'-(4-cyclohexylphenyl)-N,N'-bis-methylguanidine;

N-(5-acenaphthyl)-N'-(4-secbutylphenyl)guanidine;

N-(5-acenaphthyl)-N'-(4-secbutylphenyl)-N-methylguanidine;

N-(5-acenaphthyl)-N'-(4-secbutylphenyl)-N'-methylguanidine;

N-(5-acenaphthyl)-N'-(4-sec-butylphenyl)-N,N'-bis-methylguanidine;
N-(5-acenaphthyl)-N'-(4-methoxyphenyl)-N-methylguanidine;
N-(5-acenaphthyl)-N'-(4-methoxyphenyl)-N'-methylguanidine;
N-(5-acenaphthyl)-N'-(4-methoxyphenyl)-N,N'-bis-methylguanidine;
N-(5-acenaphthyl)-N'-(2,3-dichlorophenyl)guanidine;
N-(5-acenaphthyl)-N'-(2,3-dichlorophenyl)-N-methylguanidine;
N-(5-acenaphthyl)-N'-(2,3-dichlorophenyl)-N'-methylguanidine;
N-(5-acenaphthyl)-N'-(2,3-dichlorophenyl)-N,N'-bis-methylguanidine;
N-(5-acenaphthyl)-N'-(4-methoxy-2-naphthyl)-N-methylguanidine;
N-(5-acenaphthyl)-N'-(4-methoxy-2-naphthyl)-N'-methylguanidine;
N-(5-acenaphthyl)-N'-(4-methoxy-2-naphthyl)-N,N'-bis-methylguanidine;
N-(5-acenaphthyl)-N'-(3,4-dichlorophenyl)guanidine;
N-(5-acenaphthyl)-N'-(3,4-dichlorophenyl)-N-methylguanidine;
N-(5-acenaphthyl)-N'-(3,4-dichlorophenyl)-N'-methylguanidine;
N-(5-acenaphthyl)-N'-(3,4-dichlorophenyl)-N,N'-bis-methylguanidine;
N-(5-acenaphthyl)-N'-(4-chlorophenyl)guanidine;
N-(5-acenaphthyl)-N'-(4-chlorophenyl)-N-methylguanidine;
N-(5-acenaphthyl)-N'-(4-chlorophenyl)-N'-methylguanidine;
N-(5-acenaphthyl)-N'-(4-chlorophenyl)-N,N'-bis-methylguanidine;
N-(5-acenaphthyl)-N'-(2-naphthyl)guanidine;
N-(5-acenaphthyl)-N'-(2-naphthyl)-N-methylguanidine;
N-(5-acenaphthyl)-N'-(2-naphthyl)-N'-methylguanidine;
N-(5-acenaphthyl)-N'-(2-naphthyl)-N,N'-bis-methylguanidine;
N-(5-acenaphthyl)-N'-(6-quinolinyl)-N-methylguanidine;
N-(5-acenaphthyl)-N'-(6-quinolinyl)-N'-methylguanidine;
N-(5-acenaphthyl)-N'-(6-quinolinyl)-N,N'-bis-methylguanidine;
N-(5-acenaphthyl)-N'-(4-nitrophenyl)guanidine;
N-(5-acenaphthyl)-N'-(4-nitrophenyl)-N-methylguanidine;
N-(5-acenaphthyl)-N'-(4-nitrophenyl)-N'-methylguanidine;
N-(5-acenaphthyl)-N'-(4-nitrophenyl)-N,N'-bis-methylguanidine;
N-(5-acenaphthyl-N'-(3-bi-phenyl)guanidine;
N-(5-acenaphthyl-N'-(3-bi-phenyl)-N-methylguanidine;
N-(5-acenaphthyl-N'-(3-bi-phenyl)-N'-methylguanidine;
N-(5-acenaphthyl-N'-(3-bi-phenyl)-N,N'-bis-methylguanidine;
N-(5-acenaphthyl)-N'-(2,3-dimethylphenyl)guanidine;
N-(5-acenaphthyl)-N'-(2,3-dimethylphenyl)-N-methylguanidine;
N-(5-acenaphthyl)-N'-(2,3-dimethylphenyl)-N'-methylguanidine;
N-(5-acenaphthyl)-N'-(2,3-dimethylphenyl)-N,N'-bis-methylguanidine;
N-(5-acenaphthyl)-N'-(2-bi-phenyl)guanidine;
N-(5-acenaphthyl)-N'-(2-bi-phenyl)-N-methylguanidine;
N-(5-acenaphthyl)-N'-(2-bi-phenyl)-N'-methylguanidine;
N-(5-acenaphthyl)-N'-(2-bi-phenyl)-N,N'-bis-methylguanidine;
N-(5-acenaphthyl)-N'-(2,5-dibromophenyl)guanidine;
N-(5-acenaphthyl)-N'-(2,5-dibromophenyl)-N-methylguanidine;
N-(5-acenaphthyl)-N'-(2,5-dibromophenyl)-N'-methylguanidine;
N-(5-acenaphthyl)-N'-(2,5-dibromophenyl)-N,N'-bis-methylguanidine;
N-(5-acenaphthyl)-N'-(3,4-dimethoxyphenyl)guanidine;
N-(5-acenaphthyl)-N'-(3,4-dimethoxyphenyl)-N-methylguanidine;
N-(5-acenaphthyl)-N'-(3,4-dimethoxyphenyl)-N'-methylguanidine;
N-(5-acenaphthyl)-N'-(3,4-dimethoxyphenyl)-N,N'-bis-methylguanidine;
N-(5-acenaphthyl)-N'-(4-methoxy-1-naphthyl)-N-methylguanidine;
N-(5-acenaphthyl)-N'-(4-methoxy-1-naphthyl)-N'-methylguanidine;
N-(5-acenaphthyl)-N'-(4-methoxy-1-naphthyl)-N,N'-dimethylguanidine;
N-(5-acenaphthyl)-N'-(4-chloro-1-naphthyl)guanidine;
N-(5-acenaphthyl)-N'-(4-chloro-1-naphthyl)-N-methylguanidine;
N-(5-acenaphthyl)-N'-(4-chloro-1-naphthyl)-N'-methylguanidine;
N-(5-acenaphthyl)-N'-(4-chloro-1-naphthyl)-N,N'-bis-methylguanidine;
N-(5-acenaphthyl)-N'-(3,4,5-trichlorophenyl)guanidine;
N-(5-acenaphthyl)-N'-(3,4,5-trichlorophenyl)-N-methylguanidine;
N-(5-acenaphthyl)-N'-(3,4,5-trichlorophenyl)-N'-methylguanidine;
N-(5-acenaphthyl)-N'-(3,4,5-trichlorophenyl)-N,N'-bis-methylguanidine;
N-(5-acenaphthyl)-N'-(4-bi-phenyl)guanidine;
N-(5-acenaphthyl)-N'-(4-bi-phenyl)-N-methylguanidine;
N-(5-acenaphthyl)-N'-(4-bi-phenyl)-N'-methylguanidine;
N-(5-acenaphthyl)-N'-(4-bi-phenyl)-N,N'-bis-methylguanidine;
N-(5-acenaphthyl)-N'-(2,3,4,5-tetrachlorophenyl)guanidine;
N-(5-acenaphthyl)-N'-(2,3,4,5-tetrachlorophenyl)-N-methylguanidine;
N-(5-acenaphthyl)-N'-(2,3,4,5-tetrachlorophenyl)-N'-methylguanidine;
N-(5-acenaphthyl)-N'-(2,3,4,5-tetrachlorophenyl)-N,N'-bis-methylguanidine;
N-(5-acenaphthyl)-N'-(3-isopropylphenyl)guanidine;
N-(5-acenaphthyl)-N'-(3-isopropylphenyl)-N-methylguanidine;
N-(5-acenaphthyl)-N'-(3-isopropylphenyl)-N'-methylguanidine;

N-(5-acenaphthyl)-N'-(3-isopropylphenyl)-N,N'-bis-methylguanidine;
N-(5-acenaphthyl)-N'-(3-tert-butylphenyl)guanidine;
N-(5-acenaphthyl)-N'-(3-tert-butylphenyl)-N-methylguanidine;
N-(5-acenaphthyl)-N'-(3-tert-butylphenyl)-N'-methylguanidine;
N-(5-acenaphthyl)-N'-(3-tert-butylphenyl)-N,N'-bis-methylguanidine;
N-(5-acenaphthyl)-N'-(2,3,5,6-tetrachlorophenyl)guanidine;
N-(5-acenaphthyl)-N'-(2,3,5,6-tetrachlorophenyl)-N-methylguanidine;
N-(5-acenaphthyl)-N'-(2,3,5,6-tetrachlorophenyl)-N'-methylguanidine;
N-(5-acenaphthyl)-N'-(2,3,5,6-tetrachlorophenyl)-N,N'-bis-methylguanidine;
N-(5-acenaphthyl)-N'-(3-iodophenyl)guanidine;
N-(5-acenaphthyl)-N'-(3-iodophenyl)-N-methylguanidine;
N-(5-acenaphthyl)-N'-(3-iodophenyl)-N'-methylguanidine;
N-(5-acenaphthyl)-N'-(3-iodophenyl)-N,N'-bis-methylguanidine;
N-(5-acenaphthyl)-N'-(3-nitrophenyl)guanidine;
N-(5-acenaphthyl)-N'-(3-nitrophenyl)-N-methylguanidine;
N-(5-acenaphthyl)-N'-(3-nitrophenyl)-N'-methylguanidine;
N-(5-acenaphthyl)-N'-(3-nitrophenyl)-N,N'-bis-methylguanidine;
N-(5-acenaphthyl)-N'-(5-indolinyl)guanidine;
N-(5-acenaphthyl)-N'-(5-indolinyl)-N-methylguanidine;
N-(5-acenaphthyl)-N'-(5-indolinyl)-N'-methylguanidine;
N-(5-acenaphthyl)-N'-(5-indolinyl)-N,N'-bis-methylguanidine;
N-(5-acenaphthyl)-N'-(3-acenaphthyl)guanidine;
N-(5-acenaphthyl)-N'-(3-acenaphthyl)-N-methylguanidine;
N-(5-acenaphthyl)-N'-(3-acenaphthyl)-N'-methylguanidine;
N-(5-acenaphthyl)-N'-(3-acenaphthyl)-N,N'-bis-methylguanidine;
N-(5-acenaphthyl)-N'-(2-fluorenyl)guanidine;
N-(5-acenaphthyl)-N'-(2-fluorenyl)-N-methylguanidine;
N-(5-acenaphthyl)-N'-(2-fluorenyl)-N'-methylguanidine;
N-(5-acenaphthyl)-N'-(2-fluorenyl)-N,N'-bis-methylguanidine;
N-(5-acenaphthyl)-N'-(4-n-butoxyphenyl)guanidine;
N-(5-acenaphthyl)-N'-(4-n-butoxyphenyl)-N-methylguanidine;
N-(5-acenaphthyl)-N'-(4-n-butoxyphenyl)-N'-methylguanidine;
N-(5-acenaphthyl)-N'-(4-n-butoxyphenyl)-N,N'-bis-methylguanidine;
N-(5-acenaphthyl)-N'-(3-(2-methoxy) dibenzofuranyl)guanidine;
N-(5-acenaphthyl)-N'-(3-(2-methoxy)dibenzofuranyl)-N-methylguanidine;
N-(5-acenaphthyl)-N'-(3-(2-methoxy)dibenzofuranyl)-N'-methylguanidine;
N-(5-acenaphthyl)-N'-(3-(2-methoxy)dibenzofuranyl)-N,N'-bis-methylguanidine;
N-(5-acenaphthyl)-N'-(9-hydroxy-2-fluorenyl)guanidine;
N-(5-acenaphthyl)-N'-(9-hydroxy-2-fluorenyl)-N-methylguanidine;
N-(5-acenaphthyl)-N'-(9-hydroxy-2-fluorenyl)-N'-methylguanidine;
N-(5-acenaphthyl)-N'-(9-hydroxy-2-fluorenyl)-N,N'-bis-methylguanidine;
N-(5-acenaphthyl)-N'-(4-trifluoromethylphenyl)guanidine;
N-(5-acenaphthyl)-N'-(4-trifluoromethylphenyl)-N-methylguanidine;
N-(5-acenaphthyl)-N'-(4-trifluoromethylphenyl)-N'-methylguanidine;
N-(5-acenaphthyl)-N'-(4-trifluoromethylphenyl)-N,N'-bis-methylguanidine;
N-(5-acenaphthyl)-N'-(4-methylthiophenyl)guanidine;
N-(5-acenaphthyl)-N'-(4-methylthiophenyl)-N-methylguanidine;
N-(5-acenaphthyl)-N'-(4-methylthiophenyl)-N'-methylguanidine;
N-(5-acenaphthyl)-N'-(4-methylthiophenyl)-N,N'-bis-methylguanidine;
N-(5-acenaphthyl)-N'-(3-sec-butylphenyl)guanidine;
N-(5-acenaphthyl)-N'-(3-sec-butylphenyl)-N-methylguanidine;
N-(5-acenaphthyl)-N'-(3-sec-butylphenyl)-N'-methylguanidine; and
N-(5-acenaphthyl)-N'-(3-sec-butylphenyl)-N,N'-bis-methylguanidine;
N-(5-acenaphthyl)-N'-(4-benzyloxyphenyl)guanidine;
N-(5-acenaphthyl)-N'-(3-benzyloxyphenyl)guanidine;
N-(5-acenaphthyl)-N'-(3-seabutylphenyl)guanidine;
N-(5-acenaphthyl)-N'-(2-anthracenyl)guanidine;
N-(5-acenaphthyl)-N'-(3-phenethylphenyl)guanidine;
N-(5-acenaphthyl)-N'-(4-adamantylphenyl)guanidine;
N-(5-acenaphthyl)-N'-(3-benzyloxyphenyl)-N'-methylguanidine;
N-(5-acenaphthyl)-N'-(4-benzyloxyphenyl)-N'-methylguanidine;
N-(5-acenaphthyl)-N'-(3-biphenyl)-N'-methylguanidine;
N-(5-acenaphthyl)-N'-(3-(1'-methyl-2'-phenylethyl)phenyl)guanidine;
N-(5-acenaphthyl)-N'-(3,4-tetralinylphenyl)guanidine;
N-(5-acenaphthyl)-N'-(7-benzyltetralinylphenyl)guanidine;
N-(5-acenaphthyl)-N'-(3-1-(4-ethoxyphenyl)propanylphenylguanidine;
N-(5-acenaphthyl)-N'-(3-(N",N"-dibenzyl)aminophenyl)guanidine;
N-(5-acenaphthyl)-N'-(3-(1'-benzylbutyl)phenyl)guanidine;
N-(5-acenaphthyl)-N'-3-(4-tert-butylbenzoxymethyl)phenylguanidine;
N-(5-acenaphthyl)-N'-(2-(2-indolyl)phenyl)guanidine;
N-(5-acenaphthyl-N'-(3-bromophenyl)guanidine;
N-(5-acenaphthyl)-N'-(2,3,4-trichlorophenyl)-N,N'-dimethylguanidine;
N-(5-acenaphthyl)-N'-(2,3,4-trichlorophenyl)-N'-methylguanidine;

N-(5-acenaphthyl)-N'-(3,4-dibenzyloxyphenyl) guanidine; and

N-(5-acenaphthyl)-N'-(4-(2'-benzothiazole-6'-methyl) phenyl)guanidine;

and pharmaceutically acceptable salts of said compounds.

5. A compound having the formula:

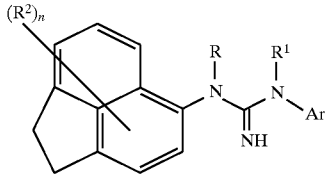

wherein:
R and $R^1$ are each independently hydrogen, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted alkylthio having from 1 to about 20 carbon atoms, substituted or unsubstituted aminoalkyl having from 1 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted alkylsulfonyl having from 1 to about 20 carbon atoms, substituted or unsubstituted carbocyclic aryl having at least about 5 ring atoms, substituted or unsubstituted aralkyl having at least about 5 ring atoms, or a substituted or unsubstituted heteroaromatic or heteroalicyclic group having from 1 to 3 rings, 3 to 8 ring members in each ring and from 1 to 3 hetero atoms;

each $R^2$ substituent is independently halogen, hydroxyl, cyano, isocyanato, nitro, amino, azido, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having 1 to about 20 carbon atoms, substituted or unsubstituted alkylthio having 1 to about 20 carbon atoms, substituted or unsubstituted alkylsulfinyl having 1 to about 20 carbon atoms, substituted or unsubstituted alkylsulfonyl having from 1 to about 20 carbon atoms, substituted or unsubstituted aminoalkyl having from 1 to about 20 carbon atoms, or substituted or unsubstituted aralkyl having at least about 5 ring atoms;

n is an integer equal to 1, 2, 3, 4, 5, 7, 8 or 9;

Ar is selected from the group consisting of substituted or unsubstituted carbocyclic aryl having at least 5 carbon atoms, and substituted or unsubstituted heteroaromatic group having 1 to 3 rings, 3 to 8 ring members in each ring and from 1 to 3 hetero atoms; and pharmaceutically acceptable salts thereof.

6. A method for treating a disorder of the nervous system in which the pathophysiology of the disorder involves excessive release of endogenous glutamate from neuronal cells comprising administering to a mammal exhibiting symptoms of said disorder or susceptible to said disorder an effective amount of a compound of claim 1 through 5.

7. The method of claim 6 wherein the disorder is 1) nausea resulting from chemotherapy, 2) epilepsy, 3) convulsions, 4) carbon monoxide poisoning, 5) cyanide poisoning, 6) toxic brain damage caused by tetrodotoxin or shell fish toxins, 7) amnesia, 8) migraine or river blindness, or 8) nerve cell death resulting from hypoxia, hypoglycemia, brain or spinal cord ischemia, brain or spinal cord trauma, stroke, heart attack, or drowning.

8. A method for treating nerve cell death comprising administering to a subject exhibiting symptoms of nerve cell death or susceptible to nerve cell death an effective amount of a compound of claim 1 through 5.

9. A method of treating brain or spinal cord trauma, stroke or heart attack comprising administering to a mammal exhibiting symptoms of or susceptible to brain or spinal cord trauma, stroke or heart attack an effective amount of a compounds of any one of claims 1 through 5.

10. A method of treating a disease selected from the group consisting of Huntington's disease, Amyotrophic Lateral Sclerosis, Alzheimer's disease, Down's Syndrome, Korsakoff's disease, olivopontocerebellar atrophy, HIV-induced dementia, HIV-induced blindness, multi-infarct dementia, or epilepsy, the method comprising administering to a mammal exhibiting symptoms of the disease or susceptible to said disease an effective amount of a compound of any one of claims 1 through 5.

11. A method for modulating the release of excess endogenous glutamate from a subject comprising administering to the subject an effective amount of a compound of any one of claims 1 through 5.

12. A method of blocking voltage sensitive calcium channels or voltage sensitive sodium channels of mammalian neuronal cells comprising administering to the cells an effective amount of a compound of claim 1 through 5.

13. A pharmaceutical composition comprising a therapeutically effective amount of one or more compounds of claim 1 or 5 and a pharmaceutically acceptable carrier.

14. A compound having the formula:

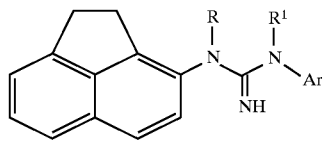

wherein:
R and $R^1$ are each independently hydrogen, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted alkylthio having from 1 to about 20 carbon atoms, substituted or unsubstituted aminoalkyl having from 1 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted alkylsulfonyl having from 1 to about 20 carbon atoms, substituted or unsubstituted carbocyclic aryl having at least about 5 ring atoms, substituted or unsubstituted aralkyl having at least about 5 ring atoms, or a substituted or unsubstituted heteroaromatic or heteroalicyclic group having from 1 to 3 rings, 3 to 8 ring members in each ring and from 1 to 3 hetero atoms;

Ar is selected from the group consisting of substituted or unsubstituted carbocyclic aryl having at least 5 carbon atoms, and substituted or unsubstituted heteroaromatic group having 1 to 3 rings, 3 to 8 ring members in each ring and from 1 to 3 hetero atoms; and pharmaceutically acceptable salts thereof.

15. A compound of claim 14 wherein Ar is phenyl independently substituted at one or more positions by halo, haloalkyl, substituted or unsubstituted alkylthio, substituted or unsubstituted alkylsulfinyl, substituted or unsubstituted alkylsulfonyl, substituted or unsubstituted alkoxy, nitro, substituted or unsubstituted carbocyclic aryl, substituted or unsubstituted aralkyl, substituted or unsubstituted aralkylamino, substituted or unsubstituted aryloxy, substituted or unsubstituted alkyleneoxyaryl, or a substituted or unsubstituted heterocyclic group.

16. A compound of claim 14 wherein Ar is substituted or unsubstituted anthracenyl, substituted or unsubstituted indolinyl, substituted or unsubstituted fluorenyl, substituted or unsubstituted bi-phenyl, substituted or unsubstituted dibenzofuranyl or substituted or unsubstituted tetralinyl.

17. A compound of claim 14 wherein the compound is selected from the group of:

N-(3-acenaphthyl)-N'-(2,3,4-trichlorophenyl)guanidine;
N-(3-acenaphthyl)-N'-(2,3,4-trichlorophenyl)-N-methylguanidine;
N-(3-acenaphthyl)-N'-(2,3,4-trichlorophenyl)-N'-methylguanidine;
N-(3-acenaphthyl)-N'-(2,3,4-trichlorophenyl)-N,N'-bis-methylguanidine;
N,N'-bis(3-acenaphthyl)-N-methylguanidine;
N,N'-bis(3-acenaphthyl)-N,N'-bis-methylguanidine;
N-(3-acenaphthyl)-N'-(1-anthracenyl)guanidine;
N-(3-acenaphthyl)-N'-(1-anthracenyl)-N-methylguanidine;
N-(3-acenaphthyl)-N'-(1-anthracenyl)-N'-methylguanidine;
N-(3-acenaphthyl)-N'-(1-anthracenyl)-N,N'-bis-methylguanidine;
N-(3-acenaphthyl)-N'-(4-tert-butylphenyl)guanidine;
N-(3-acenaphthyl)-N'-(4-tert-butylphenyl)-N-methylguanidine;
N-(3-acenaphthyl)-N'-(4-tert-butylphenyl)-N'-methylguanidine;
N-(3-acenaphthyl)-N'-(4-tert-butylphenyl)-N,N'-bis-methylguanidine;
N-(3-acenaphthyl)-N'-(4-cyclohexylphenyl)guanidine;
N-(3-acenaphthyl)-N'-(4-cyclohexylphenyl)-N-methylguanidine;
N-(3-acenaphthyl)-N'-(4-cyclohexylphenyl)-N'-methylguanidine;
N-(3-acenaphthyl)-N'-(4-cyclohexylphenyl)-N,N'-bis-methylguanidine;
N-(3-acenaphthyl)-N'-(4-sec-butylphenyl)guanidine;
N-(3-acenaphthyl)-N'-(4-sec-butylphenyl)-N-methylguanidine;
N-(3-acenaphthyl)-N'-(4-sec-butylphenyl)-N'-methylguanidine;
N-(3-acenaphthyl)-N'-(4-sec-butylphenyl)-N,N'-bis-methylguanidine;
N-(3-acenaphthyl)-N'-(4-methoxyphenyl)guanidine;
N-(3-acenaphthyl)-N'-(4-methoxyphenyl)-N-methylguanidine;
N-(3-acenaphthyl)-N'-(4-methoxyphenyl)-N'-methylguanidine;
N-(3-acenaphthyl)-N'-(4-methoxyphenyl)-N,N'-bis-methylguanidine;
N-(3-acenaphthyl)-N'-(2,3-dichlorophenyl)guanidine;
N-(3-acenaphthyl)-N'-(2,3-dichlorophenyl)-N-methylguanidine;
N-(3-acenaphthyl)-N'-(2,3-dichlorophenyl)-N'-methylguanidine;
N-(3-acenaphthyl)-N'-(2,3-dichlorophenyl)-N,N'-bis-methylguanidine;
N-(3-acenaphthyl)-N'-(4-methoxy-2-naphthyl)-N-methylguanidine;
N-(3-acenaphthyl)-N'-(4-methoxy-2-naphthyl)-N'-methylguanidine;
N-(3-acenaphthyl)-N'-(4-methoxy-2-naphthyl)-N,N'-bis-methylguanidine;
N-(3-acenaphthyl)-N'-(3,4-dichlorophenyl)guanidine;
N-(3-acenaphthyl)-N'-(3,4-dichlorophenyl)-N-methylguanidine;
N-(3-acenaphthyl)-N'-(3,4-dichlorophenyl)-N'-methylguanidine;
N-(3-acenaphthyl)-N'-(3,4-dichlorophenyl)-N,N'-bis-methylguanidine;
N-(3-acenaphthyl)-N'-(4-chlorophenyl)guanidine;
N-(3-acenaphthyl)-N'-(4-chlorophenyl)-N-methylguanidine;
N-(3-acenaphthyl)-N'-(4-chlorophenyl)-N'-methylguanidine;
N-(3-acenaphthyl)-N'-(4-chlorophenyl)-N,N'-bis-methylguanidine;
N-(3-acenaphthyl)-N'-(2-naphthyl)guanidine;
N-(3-acenaphthyl)-N'-(2-naphthyl)-N-methylguanidine;
N-(3-acenaphthyl)-N'-(2-naphthyl)-N'-methylguanidine;
N-(3-acenaphthyl)-N'-(2-naphthyl)-N,N'-bis-methylguanidine;
N-(3-acenaphthyl)-N'-(6-quinolinyl)-N-methylguanidine;
N-(3-acenaphthyl)-N'-(6-quinolinyl)-N'-methylguanidine;
N-(3-acenaphthyl)-N'-(6-quinolinyl)-N,N'-bis-methylguanidine;
N-(3-acenaphthyl)-N'-(4-nitrophenyl)guanidine;
N-(3-acenaphthyl)-N'-(4-nitrophenyl)-N-methylguanidine;
N-(3-acenaphthyl)-N'-(4-nitrophenyl)-N'-methylguanidine;
N-(3-acenaphthyl)-N'-(4-nitrophenyl)-N,N'-bis-methylguanidine;
N-(3-acenaphthyl-N'-(3-bi-phenyl)guanidine;
N-(3-acenaphthyl-N'-(3-bi-phenyl)-N-methylguanidine;
N-(3-acenaphthyl-N'-(3-bi-phenyl)-N'-methylguanidine;
N-(3-acenaphthyl-N'-(3-bi-phenyl)-N,N'-bis-methylguanidine;
N-(3-acenaphthyl)-N'-(2,3-dimethylphenyl)guanidine;
N-(3-acenaphthyl)-N'-(2,3-dimethylphenyl)-N-methylguanidine;
N-(3-acenaphthyl)-N'-(2,3-dimethylphenyl)-N'-methylguanidine;
N-(3-acenaphthyl)-N'-(2,3-dimethylphenyl)-N,N'-bis-methylguanidine;
N-(3-acenaphthyl)-N'-(2-bdi-phenyl)guanidine;
N-(3-acenaphthyl)-N'-(2-bi-phenyl)-N-methylguanidine;

N-(3-acenaphthyl)-N'-(2-bi-phenyl)-N'-methylguanidine;
N-(3-acenaphthyl)-N'-(2-bi-phenyl)-N,N'-bis-methylguanidine;
N-(3-acenaphthyl)-N'-(2,5-dibromophenyl)guanidine;
N-(3-acenaphthyl)-N'-(2,5-dibromophenyl)-N-methylguanidine;
N-(3-acenaphthyl)-N'-(2,5-dibromophenyl)-N'-methylguanidine;
N-(3-acenaphthyl)-N'-(2,5-dibromophenyl)-N,N'-bis-methylguanidine;
N-(3-acenaphthyl)-N'-(3,4-dimethoxyphenyl)guanidine;
N-(3-acenaphthyl)-N'-(3,4-dimethoxyphenyl)-N-methylguanidine;
N-(3-acenaphthyl)-N'-(3,4-dimethoxyphenyl)-N'-methylguanidine;
N-(3-acenaphthyl)-N'-(3,4-dimethoxyphenyl)-N,N'-bis-methylguanidine;
N-(3-acenaphthyl)-N'-(4-methoxy-1-naphthyl)-N-methylguanidine;
N-(3-acenaphthyl)-N'-(4-methoxy-1-naphthyl)-N'-methylguanidine;
N-(3-acenaphthyl)-N'-(4-methoxy-1-naphthyl)-N,N'-dimethylguanidine;
N-(3-acenaphthyl)-N'-(4-chloro-1-naphthyl)guanidine;
N-(3-acenaphthyl)-N'-(4-chloro-1-naphthyl)-N-methylguanidine;
N-(3-acenaphthyl)-N'-(4-chloro-1-naphthyl)-N'-methylguanidine;
N-(3-acenaphthyl)-N'-(4-chloro-1-naphthyl)-N,N'-bis-methylguanidine;
N-(3-acenaphthyl)-N'-(3,4,5-trichlorophenyl)guanidine;
N-(3-acenaphthyl)-N'-(3,4,5-trichlorophenyl)-N-methylguanidine;
N-(3-acenaphthyl)-N'-(3,4,5-trichlorophenyl)-N'-methylguanidine;
N-(3-acenaphthyl)-N'-(3,4,5-trichlorophenyl)-N,N'-bis-methylguanidine;
N-(3-acenaphthyl)-N'-(4-bi-phenyl)guanidine;
N-(3-acenaphthyl)-N'-(4-bi-phenyl)-N-methylguanidine;
N-(3-acenaphthyl)-N'-(4-bi-phenyl)-N'-methylguanidine;
N-(3-acenaphthyl)-N'-(4-bi-phenyl)-N,N'-bis-methylguanidine;
N-(3-acenaphthyl)-N'-(2,3,4,5-tetrachlorophenyl)guanidine;
N-(3-acenaphthyl)-N'-(2,3,4,5-tetrachlorophenyl)-N-methylguanidine;
N-(3-acenaphthyl)-N'-(2,3,4,5-tetrachlorophenyl)-N'-methylguanidine;
N-(3-acenaphthyl)-N'-(2,3,4,5-tetrachlorophenyl)-N,N'-bis-methylguanidine;
N-(3-acenaphthyl)-N'-(3-isopropylphenyl)guanidine;
N-(3-acenaphthyl)-N'-(3-isopropylphenyl)-N-methylguanidine;
N-(3-acenaphthyl)-N'-(3-isopropylphenyl)-N'-methylguanidine;
N-(3-acenaphthyl)-N'-(3-isopropylphenyl)-N,N'-bis-methylguanidine;
N-(3-acenaphthyl)-N'-(3-tert-butylphenyl)guanidine;
N-(3-acenaphthyl)-N'-(3-tert-butylphenyl)-N-methylguanidine;
N-(3-acenaphthyl)-N'-(3-teri-butylphenyl)-N'-methylguanidine;
N-(3-acenaphthyl)-N'-(3-tert-butylphenyl)-N,N'-bis-methylguanidine;
N-(3-acenaphthyl)-N'-(2,3,5,6-tetrachlorophenyl)guanidine;
N-(3-acenaphthyl)-N'-(2,3,5,6-tetrachlorophenyl)-N-methylguanidine;
N-(3-acenaphthyl)-N'-(2,3,5,6-tetrachlorophenyl)-N'-methylguanidine;
N-(3-acenaphthyl)-N'-(2,3,5,6-tetrachlorophenyl)-N,N'-bis-methylguanidine;
N-(3-acenaphthyl)-N'-(3-iodophenyl)guanidine;
N-(3-acenaphthyl)-N'-(3-iodophenyl)-N-methylguanidine;
N-(3-acenaphthyl)-N'-(3-iodophenyl)-N'-methylguanidine;
N-(3-acenaphthyl)-N'-(3-iodophenyl)-N,N'-bis-methylguanidine;
N-(3-acenaphthyl)-N'-(3-nitrophenyl)guanidine;
N-(3-acenaphthyl)-N'-(3-nitrophenyl)-N-methylguanidine;
N-(3-acenaphthyl)-N'-(3-nitrophenyl)-N'-methylguanidine;
N-(3-acenaphthyl)-N'-(3-nitrophenyl)-N,N'-bis-methylguanidine;
N-(3-acenaphthyl)-N'-(5-indolinyl)guanidine;
N-(3-acenaphthyl)-N'-(5-indolinyl)-N-methylguanidine;
N-(3-acenaphthyl)-N'-(5-indolinyl)-N'-methylguanidine;
N-(3-acenaphthyl)-N'-(5-indolinyl)-N,N'-bis-methylguanidine;
N-(3-acenaphthyl)-N'-(2-fluorenyl)guanidine;
N-(3-acenaphthyl)-N'-(2-fluorenyl)-N-methylguanidine;
N-(3-acenaphthyl)-N'-(2-fluorenyl)-N'-methylguanidine;
N-(3-acenaphthyl)-N'-(2-fluorenyl)-N,N'-bis-methylguanidine;
N-(3-acenaphthyl)-N'-(4-n-butoxyphenyl)guanidine;
N-(3-acenaphthyl)-N'-(4-n-butoxyphenyl)-N-methylguanidine;
N-(3-acenaphthyl)-N'-(4-n-butoxyphenyl)-N'-methylguanidine;
N-(3-acenaphthyl)-N'-(4-n-butoxyphenyl)-N,N'-bis-methylguanidine;
N-(3-acenaphthyl)-N'-(3-(2-methoxy)dibenzofuranyl)guanidine;
N-(3-acenaphthyl)-N'-(3-(2-methoxy)dibenzofuranyl)-N-methylguanidine;
N-(3-acenaphthyl)-N'-(3-(2-methoxy)dibenzofuranyl)-N'-methylguanidine;
N-(3-acenaphthyl)-N'-(3-(2-methoxy)dibenzofuranyl)-N,N'-bis-methylguanidine;
N-(3-acenaphthyl)-N'-(9-hydroxy-2-fluorenyl)guanidine;
N-(3-acenaphthyl)-N'-(9-hydroxy-2-fluorenyl)-N-methylguanidine;
N-(3-acenaphthyl)-N'-(9-hydroxy-2-fluorenyl)-N'-methylguanidine;
N-(3-acenaphthyl)-N'-(9-hydroxy-2-fluorenyl)-N,N'-bis-methylguanidine;
N-(3-acenaphthyl)-N'-(4-trifluoromethylphenyl)guanidine;
N-(3-acenaphthyl)-N'-(4-trifluoromethylphenyl)-N-methylguanidine;
N-(3-acenaphthyl)-N'-(4-trifluoromethylphenyl)-N'-methylguanidine;

N-(3-acenaphthyl)-N'-(4-trifluoromethylphenyl)-N,N'-bis-methylguanidine;
N-(3-acenaphthyl)-N'-(4-methylthiophenyl)guanidine;
N-(3-acenaphthyl)-N'-(4-methylthiophenyl)-N-methylguanidine;
N-(3-acenaphthyl)-N'-(4-methylthiophenyl)-N'-methylguanidine;
N-(3-acenaphthyl)-N'-(4-methylthiophenyl)-N,N'-bis-methylguanidine;
N-(3-acenaphthyl)-N'-(3-sec-butylphenyl)guanidine;
N-(3-acenaphthyl)-N'-(3-sec-butylphenyl)-N-methylguanidine;
N-(3-acenaphthyl)-N'-(3-sec-butylphenyl)-N'-methylguanidine; and
N-(3-acenaphthyl)-N'-(3-sec-butylphenyl)-N,N'-bis-methylguanidine;
N-(3-acenaphthyl)-N'-(4-benzoyloxyphenyl)guanidine;
N-(3-acenaphthyl)-N'-(3-benzoyloxyphenyl)guanidine;
N-(3-acenaphthyl)-N'-(3-sec-butylphenyl)guanidine;
N-(3-acenaphthyl)-N'-(2-anthracenyl)guanidine;
N-(3-acenaphthyl)-N'-(3-phenethylphenyl)guanidine;
N-(3-acenaphthyl)-N'-(4-adamantylphenyl)guanidine;
N-(3-acenaphthyl)-N'-(3-benzyloxyphenyl)-N'-methylguanidine;
N-(3-acenaphthyl)-N'-(4-benzyloxyphenyl)-N'-methylguanidine;
N-(3-acenaphthyl)-N'-(3-biphenyl)-N'-methylguanidine;
N-(3-acenaphthyl)-N'-(3-(1'-methyl-2'-phenylethyl)phenyl)guanidine;
N-(3-acenaphthyl)-N'-(3,4-tetralinylphenyl)guanidine;
N-(3-acenaphthyl)-N'-(7-benzyltetralinylphenyl)guanidine;
N-(3-acenaphthyl)-N'-(3-1-(4-ethoxy)phenyl)propanyl)phenylguanidine;
N-(3-acenaphthyl)-N'-(3-(N'',N''-dibenzyl)aminophenyl)guanidine;
N-(3-acenaphthyl)-N'-(3-(1'-benzylbutyl)phenyl)guanidine;
N-(3-acenaphthyl)-N'-3-(4-tert-butylbenzoxymethyl)phenylguanidine;
N-(3-acenaphthyl)-N'-(2-(2-indolyl)phenyl)guanidine;
N-(3-acenaphthyl-N'-(3-bromophenyl)guanidine;
N-(3-acenaphthyl)-N'-(3,4-dibenzyloxyphenyl)guanidine;
N-(3-acenapthyl)-N'-(2,3,4-trichlorophenyl)-N,N'-dimethyl guanidine;
N-(3-acenaphthyl)-N'-(2,3,4-trichlorophenyl)-N'-methylguanidine; and
N-(3-acenaphthyl)-N'-(4-(2'-benzothiazole-6'-methyl)phenyl)guanidine;
and pharmaceutically acceptable salts of said compounds.
18. A compound having the formula:

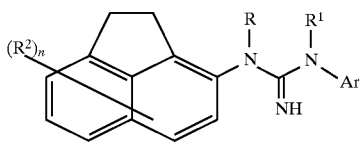

wherein:
R and R¹ are each independently hydrogen, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted alkylthio having from 1 to about 20 carbon atoms, substituted or unsubstituted aminoalkyl having from 1 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted alkylsulfonyl having from 1 to about 20 carbon atoms, substituted or unsubstituted carbocyclic aryl having at least about 5 ring atoms, substituted or unsubstituted aralkyl having at least about 5 ring atoms, or a substituted or unsubstituted heteroaromatic or heteroalicyclic group having from 1 to 3 rings, 3 to 8 ring members in each ring and from 1 to 3 hetero atoms;

each R² substituent is independently halogen, hydroxyl, cyano, isocyanato, nitro, amino, azido, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having 1 to about 20 carbon atoms, substituted or unsubstituted alkylthio having 1 to about 20 carbon atoms, substituted or unsubstituted alkylsulfinyl having 1 to about 20 carbon atoms, substituted or unsubstituted alkylsulfonyl having from 1 to about 20 carbon atoms, substituted or unsubstituted aminoalkyl having from 1 to about 20 carbon atoms, or substituted or unsubstituted aralkyl having at least about 5 ring atoms;

n is an integer equal to 1, 2, 3, 4, 5, 6, 7, 8 or 9;

Ar is selected from the group consisting of substituted or unsubstituted carbocyclic aryl having at least 5 carbon atoms, and substituted or unsubstituted heteroaromatic group having 1 to 3 rings, 3 to 8 ring members in each ring and from 1 to 3 hetero atoms; and pharmaceutically acceptable salts thereof.

19. A method for treating a disorder of the nervous system in which the pathophysiology of the disorder involves excessive release of a neurotransmitter from neuronal cells comprising administering to a mammal exhibiting symptoms of said disordcer or susceptible to said disorder an effective amount of a compound of claim 14 through 18.

20. The method of claim 19 wherein the disorder is 1) nausea resulting from chemotherapy, 2) epilepsy, 3) convulsions, 4) carbon monoxide poisoning, 5) cyanide poisoning, 6) toxic brain damage caused by tetrodotoxin or shell fish toxins, 7) amnesia, 8) migraine or river blindness, or 8) nerve cell death resulting from hypoxia, hypoglycemia, brain or spinal cord ischemia, brain or spinal cord trauma, stroke, heart attack, or drowning.

21. A method for treating nerve cell death comprising administering to a subject exhibiting symptoms of nerve cell death or susceptible to nerve cell death an effective amount of a compound of claim 14 through 18.

22. The method of claim 21 wherein the nerve cell death results from hypoxia, hypoglycemia, brain or spinal cord trauma, stroke, heart attack, or drowning.

23. A method of treating brain or spinal cord trauma, stroke or heart attack comprising administering to a mammal exhibiting symptoms of or susceptible to brain or spinal cord trauma, stroke or heart attack an effective amount of a compounds of any one of claims 14 through 18.

24. A method of treating a disease selected from the group consisting of Huntington's disease, Amyotrophic Lateral Sclerosis, Alzheimer's disease, Down's Syndrome, Korsakoff's disease, olivopontocerebellar atrophy, HIV-induced dementia, HIV-induced blindness, multi-infarct dementia, or epilepsy, the method comprising administering to a mammal exhibiting symptoms of the disease or susceptible to said disease an effective amount of a compound of any one of claims 14 through 18.

25. A method for modulating the release of excess endogenous glutamate from a subject comprising administering to the subject an effective amount of a compound of any one of claims 14 through 18.

26. A method of blocking voltage sensitive calcium channels or voltage sensitive sodium channels of mammalian neuronal cells comprising administering to the cells an effective amount of a compound of claim 14 through 18.

27. A pharmaceutical composition comprising a therapeutically effective amount of one or more compounds of claim 14 or 18 and a pharmaceutically acceptable carrier.

\* \* \* \* \*

UNITED STATES PATENT AND TRADEMARK OFFICE
CERTIFICATE OF CORRECTION

PATENT NO. : 5,847,006
DATED : December 8. 1998
INVENTOR(S) : Sharad Magar, et al.

It is certified that error appears in the above-identified patent and that said Letters Patent is hereby corrected as shown below:

Column 44, lines 11-18, delete "N-(5-acenaphthyl)-N'-(2,5-dibromophenyl)guanidine; N-(5-acenaphthyl)-N'-(2,5-dibromophenyl)-N-methylguanidine; N-(5-acenaphthyl)-N'-(2,5-dibromophenyl)-N'-methylguanidine; N-(5-acenaphthyl)-N'-(2,5-dibromophenyl)-N,N'-bis-methylguanidine;"

Column 44, lines 41-47, delete "N-(5-acenaphthyl)-N'-(3,4,5-trichlorophenyl)guanidine; N-(5-acenaphthyl)-N'-(3,4,5-trichlorophenyl)-N-methylguanidine; N-(5-acenaphthyl)-N'-(3,4,5-trichlorophenyl)-N'-methylguanidine; N-(5-acenaphthyl)-N'-(3,4,5-trichlorophenyl)-N,N'-bis-methylguanidine;"

Column 44, lines 54-62, delete "N-(5-acenaphthyl)-N'-(2,3,4,5-tetrachlorophenyl)guanidine; N-(5-acenaphthyl)-N'-(2,3,4,5-tetrachlorophenyl)-N-methylguanidine; N-(5-acenaphthyl)-N'-(2,3,4,5-tetrachlorophenyl)-N'-methylguanidine; N-(5-acenaphthyl)-N'-(2,3,4,5-tetrachlorophenyl)-N,N'-bis-methylguanidine;"

Column 45, lines 11-18, delete "N-(5-acenaphthyl)-N'-(2,3,5,6-tetrachlorophenyl)guanidine; N-(5-acenaphthyl)-N'-(2,3,5,6-tetrachlorophenyl)-N-methylguanidine; N-(5-acenaphthyl)-N'-(2,3,5,6-tetrachlorophenyl)-N'-methylguanidine; N-(5-acenaphthyl)-N'-(2,3,5,6-tetrachlorophenyl)-N,N'-bis-methylguanidine;"

Column 50, line 66, delete "bdi-phenyl" and insert therefor --bi-phenyl--.

UNITED STATES PATENT AND TRADEMARK OFFICE
CERTIFICATE OF CORRECTION

PATENT NO. : 5,847,006
DATED : December 8, 1998
INVENTOR(S) : Sharad Magar, et al.

It is certified that error appears in the above-identified patent and that said Letters Patent is hereby corrected as shown below:

Column 51, lines 4-11, delete "N-(3-acenaphthyl)-N'-(2,5-dibromophenyl)guanidine; N-(3-acenaphthyl)-N'-(2,5-dibromophenyl)-N-methylguanidine; N-(3-acenaphthyl)-N'-(2,5-dibromophenyl)-N'-methylguanidine; N-(3-acenaphthyl)-N'-(2,5-dibromophenyl)-N,N'-bis-methylguanidine;"

Column 51, lines 33-40, delete "N-(3-acenaphthyl)-N'-(3,4,5-trichlorophenyl)guanidine; N-(3-acenaphthyl)-N'-(3,4,5-trichlorophenyl)-N-methylguanidine; N-(3-acenaphthyl)-N'-(3,4,5-trichlorophenyl)-N'-methylguanidine; N-(3-acenaphthyl)-N'-(3,4,5-trichlorophenyl)-N,N'-bis-methylguanidine;"

Column 51, lines 47-54, delete "N-(3-acenaphthyl)-N'-(2,3,4,5-tetrachlorophenyl)guanidine; N-(3-acenaphthyl)-N'-(2,3,4,5-tetrachlorophenyl)-N-methylguanidine; N-(3-acenaphthyl)-N'-(2,3,4,5-tetrachlorophenyl)-N'-methylguanidine; N-(3-acenaphthyl)-N'-(2,3,4,5-tetrachlorophenyl)-N,N'-bis-methylguanidine;"

UNITED STATES PATENT AND TRADEMARK OFFICE
CERTIFICATE OF CORRECTION

PATENT NO.   : 5,847,006
DATED        : December 8, 1998
INVENTOR(S)  : Sharad Magar, et al.

It is certified that error appears in the above-identified patent and that said Letters Patent is hereby corrected as shown below:

Column 52, lines 3-11, delete "N-(3-acenaphthyl)-N'-(2,3,5,6-tetrachlorophenyl)guanidine; N-(3-acenaphthyl)-N'-(2,3,5,6-tetrachlorophenyl)-N-methylguanidine; N-(3-acenaphthyl)-N'-(2,3,5,6-tetrachlorophenyl)-N'-methylguanidine; N-(3-acenaphthyl)-N'-(2,3,5,6-tetrachlorophenyl)-N,N'-bis-methylguanidine;"

Signed and Sealed this

Tenth Day of August, 1999

Attest:

Q. TODD DICKINSON

*Attesting Officer*    Acting Commissioner of Patents and Trademarks